US006841684B2

(12) United States Patent
Chow et al.

(10) Patent No.: US 6,841,684 B2
(45) Date of Patent: Jan. 11, 2005

(54) IMIDIAZOLES HAVING REDUCED SIDE EFFECTS

(75) Inventors: Ken Chow, Newport Coast, CA (US); Daniel W. Gil, Corona Del Mar, CA (US); James A. Burke, Santa Ana, CA (US); Dale A. Harcourt, Irvine, CA (US); Michael E. Garst, Newport Beach, CA (US); Larry A. Wheeler, Irvine, CA (US); Stephen A. Munk, Northville, MI (US); Dario G. Gomez, Irvine, CA (US); Todd M. Heidelbaugh, Fountain Valley, CA (US)

(73) Assignee: Allergan, Inc., Irvine, CA (US)

( * ) Notice: Subject to any disclaimer, the term of this patent is extended or adjusted under 35 U.S.C. 154(b) by 19 days.

(21) Appl. No.: 09/815,362

(22) Filed: Mar. 21, 2001

(65) Prior Publication Data
US 2003/0023098 A1 Jan. 30, 2003

Related U.S. Application Data

(63) Continuation-in-part of application No. 09/329,752, filed on Jun. 10, 1999, now abandoned, which is a continuation-in-part of application No. 09/205,597, filed on Dec. 4, 1998, now abandoned, which is a continuation-in-part of application No. 08/985,347, filed on Dec. 4, 1997, now abandoned.

(51) Int. Cl.[7] ............................................ C07D 233/64
(52) U.S. Cl. ................................................... 548/335.1
(58) Field of Search ........................... 548/335.1, 311.1, 548/315.1, 315.4, 325.1, 346.1; 514/249, 377, 397, 213, 401, 413, 415, 913, 370, 392, 254, 186

(56) References Cited

U.S. PATENT DOCUMENTS

| 4,443,466 A | 4/1984 | Karjalainen et al. ........ 424/274 |
| 4,496,572 A | 1/1985 | Cross et al. ................. 519/337 |
| 4,540,705 A | 9/1985 | Bailey ......................... 514/401 |
| RE32,400 E | 4/1987 | Karjalainen et al. ........ 514/397 |
| 5,021,416 A | 6/1991 | Gluchowski |
| 5,034,406 A | 7/1991 | Gluchowski |
| 5,066,664 A | 11/1991 | Gluchowski |
| 5,077,292 A | 12/1991 | Gluchowski |
| 5,091,528 A | 2/1992 | Gluchowski |
| 5,112,822 A | 5/1992 | Gluchowski |
| 5,130,441 A | 7/1992 | Gluchowski |
| 5,151,440 A | 9/1992 | Gluchowski |
| 5,151,526 A | 9/1992 | Hsu et al. ............ 548/315.1 X |
| 5,180,721 A | 1/1993 | Burke et al. |
| 5,198,442 A | 3/1993 | Gluchowski |
| 5,215,991 A | 6/1993 | Burke et al. |
| 5,231,096 A | 7/1993 | Gluchowski |
| 5,552,403 A | 9/1996 | Burke et al. |
| 5,561,132 A | 10/1996 | Burke et al. |
| 5,580,892 A | 12/1996 | Garst et al. |
| 5,621,113 A | 4/1997 | Boyd et al. |
| 5,663,189 A | 9/1997 | Maurer et al. |
| 5,750,720 A | 5/1998 | Boyd et al. ............... 548/315.1 |

FOREIGN PATENT DOCUMENTS

| EP | 0 194 984 | 9/1986 |
| EP | 0 304 910 | 3/1989 |
| JP | 1/242571 | 9/1989 |
| JP | 4/267130 | 9/1992 |
| WO | WO 94/07866 | 4/1994 |
| WO | WO 95/16449 | 6/1995 |
| WO | WO 95/19968 | 7/1995 |
| WO | WO 96/01813 | 1/1996 |
| WO | WO 97/03079 | 1/1997 |
| WO | WO 97/12874 | 4/1997 |
| WO | WO 97/15302 | 5/1997 |
| WO | WO 97/31636 | 9/1997 |
| WO | WO 97/35858 | 10/1997 |

OTHER PUBLICATIONS

Bylund et al, 1994, Pharmacol. Rev. 46, pp. 121–136, "International Union of Pharmacology Nomenclature of Adrenoceptors".
Shimizu et al, 1969, J. Neurochem. 16, pp. 1609–1619, "A Radioisotopic Method For Measuring The Formation of Adenosine 3', 5'–Cyclic Monophosphate in Incubated Slices of Brain".
Messier et al, 1995, Pharmacol. Toxicol. 76, pp. 308–311, "High Throughput Assays of Cloned Adrenergic, Muscarinic, Neurokinin, and Neurotrophin Receptors in Living Mammalian Cells".
Neve et al, 1992, J. Biol. Chem. 267, pp. 25748–25753, "Dopamine D2 Receptor Stimulation of Na+/H+Exchange Assessed by Quantification of Extracellular Acidification".
Williams et al, 1990, J. Auton. Pharmacol, 10, 247, pp. 109–118, "$\alpha_2$–adrenceptor antisecretory responses in the rat jejunum".
Fondacaro et al, 1988, vol. 247, No. 2, pp. 481–486, "The Journal of Pharmacology and Experimental Therapeutics".
White et al, 1975, Communications/Synthesis, pp. 602–603, "A Convenient Procedure for the Preparation of 2–endo–Hydroxy–cis–bicyclo [3.3.0]octane".
Conklin et al, Nature, 1993, vol. 363, pp. 274–276, "Substitution of three amino acids switches receptor specifity of $G_q\alpha$ to that of $G_1\alpha$".
Schaaf et al, J. Med. Chem. 1983, vol. 26, pp. 328–334, "Structure–Activity Studies of Configurationally Rigid Arylprostaglandins".
Kihara et al, "Preparation of imidazole derivatives as drugs", 6001 Chemical Abstracts, Columbus, Ohio, U.S. vol. 112 (Apr. 9, 1996), No. 16, XP–002098179.
Zhang et al, "Medetomidine Analogs as $\alpha_2$–Adrenergic Ligands. 3. Synthesis annd Biological Evaluation of a New Series of Medetomidine Analogs and Their Potential Binding Interactions with $\alpha_2$–Adrenoceptors Involving a 'Methyl Pocket'", J. Med. Chemc. 1997, 40. pp. 3014–3024.

Primary Examiner—Joseph K. McKane
Assistant Examiner—Rebecca Anderson
(74) Attorney, Agent, or Firm—Carlos A. Fisher; Martin A. Voet; Robert J. Baran

(57) ABSTRACT

Methods and compounds for the treatment of conditions including pain, particularly chronic pain, glaucoma or elevated intraocular pressure with reduced cardiovascular or sedative side effects. Also included are methods of making and using such compounds.

18 Claims, No Drawings

IMIDIAZOLES HAVING REDUCED SIDE EFFECTS

This application is a continuation in part of application Ser. No. 09/329,752, filed (Jun. 10, 1999, now abandoned, which was a continuation in part of application Ser. No. 09/205,597, filed Dec. 4, 1998, now abandoned, which was a continuation in part of application Ser. No. 08/985,347, filed Dec. 4, 1997, now abandoned.

FIELD OF THE INVENTION

The present invention is directed to a method of treating pain, particularly chronic pain, glaucoma or elevated intraocular pressure and other diseases with substantially reduced cardiovascular or sedative side effects by administering to mammals including humans, compounds which are selective agonists of the α2B alone or α2B and α2C adrenergic receptor subtypes and which lack substantial activity at the α2A receptor subtype. The present invention is also directed to novel compounds and pharmaceutical compositions adapted for administering said compounds to mammals, including humans.

BRIEF DESCRIPTION OF THE PRIOR ART

Compounds which have adrenergic activity are well known in the art, and are described in numerous United States and foreign patents and in scientific publications. It is generally known and accepted in the art that adrenergic activity is useful for treating animals of the mammalian species, including humans, for curing or alleviating the symptoms and conditions of numerous diseases and conditions. In other words, it is generally accepted in the art that pharmaceutical compositions having an adrenergic compound or compounds as the active ingredient are useful for treating glaucoma, chronic pain, nasal congestion, high blood pressure, congestive heart failure and inducing anesthesia.

The two main families of adrenergic receptor are termed alpha adrenergic receptors and beta adrenergic receptors in the art, and each of these two families is known to have subtypes, which are designated by letters of the alphabet, such as α2A, α2B. See the article by Bylund et al, *Pharmacol Rev.* 46, pp. 121–136(1994). All these and other references cited herein are hereby incorporated within this specification.

SUMMARY OF THE INVENTION

It has been discovered in accordance with the present invention that adrenergic compounds which act selectively, and preferably even specifically as agonists of the α2B or α2B/α2C (hereinafter referred to as α2B or α2B/2C) receptor subtypes in preference over the α2A receptor subtype, possess desirable therapeutic properties associated with adrenergics but without having one or more undesirable side effects such as changes in blood pressure or sedation. For the purposes of the present invention, a compound is defined to be a specific or at least selective agonist of the α2B or α2B/2C receptor subtype(s) if the compound is at least approximately ten times more potent as an agonist at either the α2B and α2C or both receptor subtypes than at the α2A receptor subtype, or if the difference in the compound's efficacy at the α2B and α2B/2C receptor relative to the α2A receptor is greater than 0.3 and its efficacy at the α2A receptor is ≦0.4.

Accordingly, the present invention relates to methods of treating animals of the mammalian species, including humans, with a pharmaceutical composition comprising one or more specific or selective α2B or α2B/2C adrenergic agonist compounds as the active ingredient, for treatment of the many diseases or conditions against which alpha adrenergic compounds are useful, including without limitation glaucoma, reducing elevated intraocular pressure, chronic pain, diarrhea, and nasal congestion. In addition, the compounds of this invention are useful for treating muscle spasticity including hyperactive micturition, diarrhea, diuresis, withdrawal syndromes, pain including neuropathic pain, neurodegenerative diseases including optic neuropathy, spinal ischemia and stroke, memory and cognition deficits, attention deficit disorder, psychoses including manic disorders, anxiety, depression, hypertension, congestive heart failure, cardiac ischemia and nasal congestion.

It is an object of this invention to provide novel compounds having substantial analgesic activity in the treatment of chronic pain, regardless of origin. Chronic pain may be, without limitation, visceral, inflammatory, referred or neuropathic in origin. Such chronic pain may arise as a result of, or be attendant to, conditions including without limitation: arthritis, (including rheumatoid arthritis), spondylitis, gouty arthritis, osteoarthritis, juvenile arthritis, and autoimmune diseases including, without limitation, lupus erythematosus.

By "chronic pain" is meant pain other than acute pain, such as, without limitation, neuropathic pain, visceral pain (including that brought about by Cron's disease and irritable bowel syndrome (IBS)), and referred pain.

By "acute pain" is meant immediate, usually high threshold, pain brought about by injury such as a cut, crush, burn, or by chemical stimulation such as that experienced upon exposure to capsaicin, the active ingredient in chili peppers.

The present compositions can also be used within the context of the treatment of chronic gastrointestinal inflammations, Crohn's disease, gastritis, irritable bowel disease (IBD) and ulcerative colitis; and in treatment of visceral pain, including pain caused by cancer or attendant to the treatment of cancer as, for example, by chemotherapy or radiation therapy.

These compositions can be used within the context of the treatment of other chronic pain symptoms, and especially in the treatment of chronic forms of neuropathic pain, in particular, without limitation, neuralgia, herpes, deafferentation pain, and diabetic neuropathies. In a preferred embodiment these compositions are specifically analgesic in chronic pain models and do not have significant activity in acute pain models.

It is also an object of this invention to provide novel compounds for treating ocular disorders, such as ocular hypertension, glaucoma, hyperemia, conjunctivitis and uveitis.

It is also an object of this invention to provide novel compounds for treating the pain associated with substance abuse and/or withdrawal.

It is a still further object of this invention to provide such compounds which have good activity when delivered by peroral, parenteral, intranasal, ophthalmic, and/or topical dosing, or injection.

It is also an object of this invention to provide methods of treating pain through the therapeutic administration of the compounds disclosed herein.

It is further an object of the present invention to provide methods of treating conditions known to be susceptible to treatment through alpha 2 adrenergic receptors.

The present invention is also directed to the pharmaceutical compositions used in the above-noted methods of treatment.

The present invention particularly covers methods for treating diseases and conditions where adrenergic compounds are effective for treatment, but their use is limited because of their generally known side effects.

Thus is a major embodiment, the present invention is drawn to compounds of the following structure:

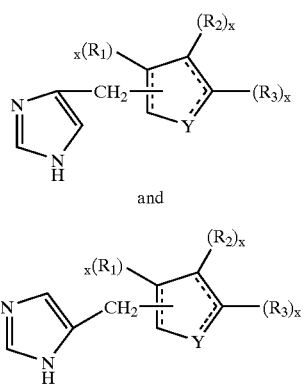

in which each x is independently 1 or 2;
each $R_1$ is independently selected from the group consisting of H; halogen; $C_{1-4}$ alkyl; $C_{1-4}$ alkenyl; $C_{1-4}$ alkynyl; —$COR_4$ where $R_4$ is H, $C_{1-4}$ alkyl or $C_{1-4}$ alkoxy; $C_{3-6}$ cycloalkyl; aryl; heteroaryl; cyano; nitro; trihalomethyl; oxo; or —$(CH_2)_n$—X—$(CH_2)_m$—$(R_5)_o$ where X is O, S or N, n is 0–3, m is 0–3, o is 0–1, and $R_5$ is methyl or $H_{1-2}$;
each $R_2$ and each $R_3$ are independently selected from the group consisting of H; halogen; $C_{1-4}$ alkyl; $C_{1-4}$ alkenyl; $C_{1-4}$ alkynyl; —$COR_4$ where $R_4$ is H; $C_{1-4}$ alkyl or $C_{1-4}$ alkoxy; $C_{3-6}$ cycloalkyl; aryl; heteroaryl; cyano; nitro; trihalomethyl; oxo; or —$(CH_2)_n$—X—$(CH_2)_m$—$(R_5)_o$ where X is O, S or N, n is 0–3, m is 0–3, o is 0–1, and $R_5$ is methyl or $H_{1-2}$; or an $R_2$ and an $R_3$ together condense to form a saturated, partly saturated, or unsaturated ring structure having the formula —$C(R_6)_p)_q$—$X_s$—$(C(R_6)_p)_r$—$X_t$—$(C(R_6)_p)_u$ where each $R_6$ is independently selected from the group consisting of H; halogen; $C_{1-4}$ alkyl; $C_{1-4}$ alkenyl; $C_{1-4}$ alkynyl; —$COR_4$ where $R_4$ is H, $C_{1-4}$ alkyl or $C_{1-4}$ alkoxy; $C_{3-6}$ cycloalkyl; aryl; heteroaryl; cyano; nitro; trihalomethyl and oxo where each p is independently 1 or 2, q is 0–5, r is 0–5, u is 0–5; each X is independently O, S, or N and s is 0 or 1; provided that q+r+u+s+t is less than 6;
Y is selected from the group consisting of O; S; N; —(C$(R_7)_z)_s$-where each $R_7$ is independently as previously defined for R1, each z is independently 1–2, and s is 1–3; —CH=; —CH=CH—; or $Y_1CH_2$— where $Y_1$ is O, N, or S; and the dotted lines are optional double bonds, with the proviso that if the ring including Y is a cyclohexane ring or a heterocyclic 5 member ring said ring is not fully unsaturated, and that if Y is O, N or S, the ring including Y contains at least one said double bond, said compound further having selective agonist activity at the α2B or α2B/α2C adrenergic receptor subtype(s) over the α2A adrenergic receptor subtype, and all pharmacologically acceptable salts, esters, stereoisomers and racemic mixtures thereof.

DETAILED DESCRIPTION OF THE INVENTION

Compounds which are used in the pharmaceutical compositions and methods of treatment of the present invention are selective or specific agonists of the α2B or α2B/2C adrenergic receptor subtypes, in preference over the 2A receptor subtype. In accordance with the present invention, a compound is considered a selective α2B or α2B/2C agonist if that compound's difference in efficacy as an agonist of the α2B or α2B/2C receptor subtype(s) compared to the α2A receptor subtype is greater than 0.3 and its efficacy at the α2A receptor subtype is ≦0.4 and/or it is at least approximately 10 times more potent. Preferably, the compounds utilized in accordance with the present invention are specific agonists of the α2B or α2B/2C receptor subtypes. Specifically, in this regard, a specific agonist is defined in the sense that a specific α adrenergic agonist does not act as an agonist of the α2A receptor subtype to any measurable or biologically significant extent.

A set of agents has been discovered that are functionally selective for the α2B or α2B/2C—subtypes of said adrenergic receptors. This preferential activity can be determined in a variety of functional assays such as Cyclic AMP Production, Shimizu et al, *J. Neurochem.* 16, pp. 1609–1619 (1969); R-SAT (Receptor Selection and Amplification Technology), Messier et al, *Pharmacol. Toxicol.* 76, pp. 308–311(1995) and the Cytosensor microphysiometer, Neve et al, *J. Biol. Chem.* 267, pp. 25748–25753, (1992) using cells that naturally express individual subtypes or have had one of the subtypes introduced. The cells or recombinant receptors used should be human or from a species that has been shown to have a similar pharmacology. In the study below, the RSAT assay on cells that have been transiently transfected with the human α2A (c10 gene), rat α2B (RNG gene) and human α2C (c4 gene) receptors was used. The rat α2B receptor has been shown to have a pharmacology that corresponds to the human α2B receptor (see, for example, Bylund et al., *Pharmocol, Rev.* 46, pp. 127–129(1994)).

In the treatment of glaucoma, particularly, topical administration may be used. Any common topical formulation such as a solution, suspension, gel, ointment, or salve and the like may be applied to the eye in glaucoma and dermally to treat other indications. Preparation of such topical formulations are well described in the art of pharmaceutical formulations as exemplified, for example, by Remington's Pharmaceutical Science, Edition 17, Mack Publishing Company, Easton, Pa.

Applicants have discovered that the compounds of this invention activate $α_2$ receptors, particularly $α_{2B}$ receptors. In a particular use, these compounds act as a highly effective analgesic, particularly in chronic pain models, with minimal undesirable side effects, such as sedation and cardiovascular depression, commonly seen with agonists of the $α_2$ receptors.

In the treatment of pain such compounds may be administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. Generally, such doses will be in the range 1–1000 mg/day; more preferably in the range 10 to 500 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The compounds are useful in the treatment of pain in a mammal; particularly a human being. Preferably, the patient will be given the compound orally in any acceptable form, such as a tablet, liquid, capsule, powder and the like. However, other routes may be desirable or necessary, particularly if the patient suffers from nausea. Such other routes may include, without exception, transdermal, parenteral, subcutaneous, intranasal, intrathecal, intramuscular, intravenous, and intrarectal modes of delivery. Additionally, the formulations may be designed to delay release of the active compound over a given period of time, or to carefully control the amount of drug released at a given time during the course of therapy.

If the drug is to be administered systemically, it may be confected as a powder, pill, tablet or the like or as a syrup or elixir for oral administration. For intravenous, intraperitoneal, intrathecal or epidural administration, the compound will be prepared as a solution or suspension capable of being administered by injection. In certain cases, it may be useful to formulate these compounds in suppository or as an extended release formulation, including the dermal patch form, for deposit on or under the skin or for intramuscular injection.

Treatment of glaucoma or any other indications known or discovered to be susceptible to treatment by adrenergic compounds will be effected by administration of therapeutically effective dose of one or more compounds in accordance with the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that in the treatment of, for example, glaucoma, that a formulation containing between 0.001 and 5 percent by weight, preferably about 0.01 to 3% will usually constitute a therapeutically effective concentration. If administered systemically, an amount between 0.001 and 50 mg per kg, preferably between 0.001 and 10 mg per kg body weight per day, but most preferably about 0.01 to 1.0 mg/kg, will effect a therapeutic result in most instances.

Because the α2B and α2B/2C specific selective agonist compounds lack substantial 2A side effects, treatments of diseases or conditions with such compounds in accordance with the present invention is advantageous, particularly when the treatment is directed to a human having cardiovascular problems.

The general structures of exemplary specific α2B and α2C agonist or selective α2B and α2B/2C agonist adrenergic compounds which are used in the pharmaceutical compositions and methods of treatment of the present invention are provided by general Formulas, below.

In one aspect of the invention, a compound having selective agonist activity at the α2B or α2B/2C adrenergic receptor subtype(s) as compared to the 2A adrenergic receptor subtype is represented by the general formula:

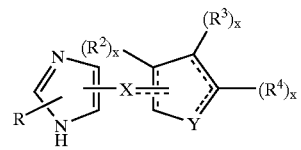

I wherein the dotted lines represent optional bonds provided that two double bonds may not share a common carbon atom; R is H or lower alkyl; X is S or C(H)R$^1$, wherein R$^1$ is H or lower alkyl, but R$^1$ is absent when the bond between X and the ring represented by:

is a double bond; Y is O, N, S, (CR$^1$$_2$)$_y$, wherein y is an integer of from 1 to 3, —CH=CH— or —Y$^1$CH$_2$—, wherein Y$^1$ is O, N or S; x is an integer of 1 or 2, wherein x is 1 when R$^2$, R$^3$ or R$^4$ is bound to an unsaturated carbon atom and x is 2 when R$^2$, R$^3$ or R$^4$ is bonded to a saturated carbon atom; R$^2$ is H, halogen, hydroxy, lower alkyl, alkoxy, alkenyl, acyl, alkynyl, or, when attached to a saturated carbon atom, R$_2$ may be oxo; R$_3$ and R$_4$ are, each, H, halogen, lower alkyl, alkenyl, acyl, alkynyl, aryl, e.g. phenyl or naphthyl, heteroaryl, e.g. furyl, thienyl, or pyridyl, and substituted aryl or heteroaryl, wherein said substituent may be halogen, lower alkyl, alkoxy, alkenyl, acyl, alkynyl, nitro, cyano, trifluoromethyl, hydroxy, etc. or, together, are —(C(R$^2$)x)z-; —Y$^1$(C(R$^2$)x)z'-; —Y$^1$ (C(R$^2$)x)y Y$^1$—; —(C(R$^2$)x)- Y$^1$—(C(R$^2$)x)-; —(C(R$^2$)x)- Y$^1$—(C(R$^2$)x)-(C(R$^2$)x)- and —Y$^1$—(C(R$^2$)x)- Y$^1$—(C(R$^2$)x)- wherein z is an integer of from 3 to 5, z' is an integer of from 2 to 4 and x and y are as defined above, and further either end of each of these divalent moieties may attach at either R3 or R4 to form a condensed ring structure shown generally as:

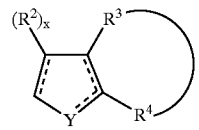

and the rings formed may be totally unsaturated, partially unsaturated, or totally saturated provided that a ring carbon has no more than 4 valences, nitrogen no more than three and O and S have no more than two.

In another aspect of the invention in the above compound is represented by the formula:

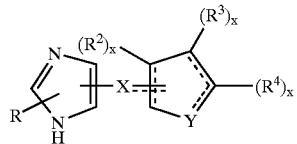

II wherein X may be C(H)R$^1$ and R$^1$ is H.

In said compound of formula II, $R_2$ may be H and

may represent a furanyl radical.

In such furanyl derivatives of Formula II, $R^3$ and $R^4$ together may be $(CH)_4$, or $R^3$ may be H and $R^4$ may be t-butyl, or $R^3$ and $R^4$ may be H, or $R^3$ may be H and $R^4$ may be methyl or ethyl.

Alternatively, in the compound of Formula I, $R^1$ may be methyl and

may represent a furanyl radical.

Alternatively, in said compounds of Formula II, $R^2$ may be H and

may represent a thienyl radical.

In such thienyl derivatives of Formula II, $R^3$ and $R^4$, together, may represent $(CH_2)_4$, or $R^3$ may be phenyl and $R^4$ may be H, or $R^3$ and $R^4$ together, may represent $(CH_2)_3S$, or $R^3$ and $R^4$ may be H, or $R^3$ and $R^4$, together, may represent $(CH)_4$, or may be $R^3$ may be H and $R^4$ may be methyl, or $R^3$ may be bromo and $R^4$ may be H, or $R^3$ may be hydrogen and $R^4$ may be chloro, or $R^3$ may be methyl and $R^4$ may be hydrogen.

Alternatively, in the compounds of Formula II:

may represent a cyclohexyl radical.

In such cyclohexyl derivatives of Formula II, $R^2$ may be hydrogen and $R^3$ and $R^4$ may, together, represent $(CH)_4$, or $R^2$ may be oxo and $R^3$ and $R^4$, together, may be $(CH)_4$, or $R^2$ may be hydrogen or oxo and $R^3$ and $R^4$, together, may represent $(CH)_2S$, or $R^2$ may be hydrogen and $R^3$ and $R^4$ may, together, represent $(CH_2)_4$, forming an octahydronaphthalene, or $R^2$ may be oxo and $R^3$ and $R^4$ may, together, represent $(CH_2)_4$, or $R^2$ may be oxo and $R^3$ and $R^4$, together, may represent $(CH)_2C(CH_3)(CH)$, or $R^2$ may be hydrogen and $R^3$ and $R^4$, together, may represent $S(CH_2)_2$, or $R^2$, $R^3$ and may be H, or $R^2$ may be oxo and $R^3$ and $R^4$, together, may represent $(CH)_2C(OCH_3)CH$, or $R^3$ and $R^4$ together may represent $—Y^1—C(R_2)_x—C(R_2)_x-Y^1-$ wherein $Y^1$ is N, forming a tetrahydroquinoxaline wherein $R^2$ may be hydrogen or oxo.

Alternatively, in the compounds of Formula II:

may represent a tetrahydroquinoline radical wherein $R^3$ and $R^4$ together are $—Y^1—C(R_2)_x—C(R_2)_x—C(R_2)_x—$ wherein $Y^1$ is N. In such tetrahydroquinoline derivatives $(R^2)_x$ may be hydrogen or oxo; or may represent a tetrahydroisoquinoline radical wherein $R^3$ and $R^4$ together are $—C(R_2)_x—Y^1—C(R_2)_x—C(R_2)_x—$ wherein $Y^1$ is N and $(R^2)_x$ may be hydrogen or oxo.

Alternatively, in the compounds of Formula II:

may represent a cyclopentyl radical.

In such cyclopentyl derivatives of Formula II, $R^2$ may be H and $R^3$ and $R^4$, together, may represent $(CH)_4$, or $R^2$ may be oxo and $R^3$ and $R^4$, together, may represent $(CH)_4$, or $R^2$ may be hydrogen and $R^3$ and $R^4$, together, may represent $(CH_2)_3$.

In another aspect of the invention, Y is $(CH_2)_3$ and X may be CH and $R^2$ may be oxo or X may be $CH_2$ and $R^2$ may be H and $R^3$ and $R^4$, together, may represent $(CH)_4$. Alternatively, $R^3$ and $R^4$, together, may represent $(CH)_4$, Y may be $CH_2C(CR^1_2)_2$ wherein $R^1$ is hydrogen, or Y may be $—CH2C(Me)—$ and $R^2$ may be hydrogen or oxo.

Finally, in the compounds of Formula II:

may represent a phenyl radical.

In such phenyl derivatives of Formula I, X may be $CH_2$, R maybe H or $CH_3$, $R^2$, $R^3$ and $R^4$ may be H, or $R^3$ and $R^4$, together, represent $O(CR^2)_2O$ to provide a 1,4-benzodioxan derivative, or alternatively, X may be S and $R^2$, $R^3$ and $R^4$ may be H.

In another aspect of the invention, said compound has the formula:

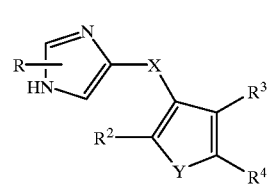

III wherein Y is S or O.

In such compound of Formula III, X may be $C(H)R^1$, R, $R^1$, $R^2$, $R^3$ and $R^4$ may be H and Y may be O or S.

In another aspect of the invention, said compound has the formula:

IV and $R^3$ and $R^4$, together, represent $(CH)_4$.

In such compounds of Formula IV, $Y^1$ may be O, $R^2$ may be oxo and X is CH or $CH_2$, or one of $R^2$ is hydroxy and the other may be H, or $R^2$ may be H.

In such compounds of Formula IV, $Y^1$ may be S, X may be $CH_2$ and $R^2$ may be oxo, or $R^2$ may be H and X may be CH and $R^2$ may be oxo.

In another aspect of the invention, the compound having selective activity at the 2B or 2B and 2C adrenergic receptor subtype(s) as compared to the 2A adrenergic receptor subtype is represented by the formula:

V alternatively W is a bicyclic radical selected from the group consisting of:

wherein $R^5$, $R^6$, $R^7$ and $R^8$ are selected from the group consisting of H and lower alkyl provided that at least one of $R^5$ and $R^6$ or $R^6$ and $R^7$ are $OC(R^9)C(R^9)N(R)$ to form a condensed ring with:

wherein $R^9$ is H, lower alkyl or oxo; and wherein $R^{10}$ is H, lower alkyl, phenyl or lower alkyl substituted phenyl, and Z is O or NH. Compounds wherein W is norbornyl are disclosed and claimed in commonly assigned co-pending application 09/003902, filed on 7 Jan. 1998, which is hereby incorporated by reference in its entirety.

In one aspect of the invention Z may be O and W may be:

and $R^{10}$ may be selected from the group consisting of H, phenyl and o-methylphenyl, e.g. $R^{10}$ may be o-methylphenyl.

In another aspect of the invention W may be:

wherein Z may be NR, R may be methyl or hydrogen, one of $(R^9)_x$ may be H and $R^5$ may be H.

Alternatively, W may be:

wherein R may be H and $R^8$ may be methyl.

It is understood that wherein a reference to lower alkyl, alkoxy, alkenyl or alkynyl is made above, it is intended to mean radicals having from one to eight carbons, preferably from one to four carbon atoms. Where reference to aryl is made above, it is intended to mean radicals of from six to fourteen carbon atoms, preferably from six to ten carbon atoms. Where reference is made to halogen, fluoro and chloro are preferred.

The invention is further illustrated by the following examples (including general synthetic schemes therefore) which are illustrative of various aspects of the invention and are not intended as limiting the scope of the invention as defined by the appended claims.

EXAMPLE A

Synthesis of 1-dimethylsulfamoyl-2-t-butyldimethylsilyl-5-imidazolecarboxaldehyde:

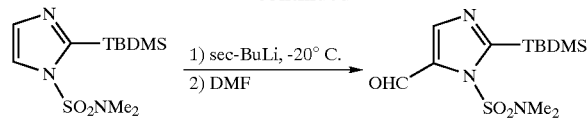

Procedure-

Imidazole (1) (20.0 g, 0.29 mol), triethylamine (41.0 mL, 0.29 mol) and N,N-dimethylsulfamoyl chloride (31.6 mL, 0.29 mol) were added to 320 mL of benzene. The reaction was stirred for 48 h at room temperature (rt) and then filtered. The filtrate was collected and concentrated under reduced pressure. Vacuum distillation of the crude product (~0.5 mmHg, 115°–118° C.) afforded 38.7 g (76%) of a clear and colorless oil. Upon cooling the product solidifies to give white crystals (2). 1-(Dimethylsulfamoyl) imidazole (2) (18.8 g, 0.11 mol) was added to 430 mL of tetrahydrofuran (THF). The solution was cooled to −78° C. A solution of n-butyl lithium (n-BuLi) in hexane (1.6M, 70.9 mL, 0.11 mol) was added dropwise to the reaction flask. Upon completion, the reaction was stirred for 1 h at −78° C. t-Butyldimethylsilylchloride (17.8 g, 0.12 mol) in 50 mL of THF was added via cannula to the reaction. After the addition was completed the reaction mixture was warmed slowly to rt and then stirred for 24 h. The reaction was diluted with water and the organic layer separated. The organic phase was washed with brine and then dried over sodium sulfate. The mixture was filtered and the filtrate concentrated under reduced pressure. Column chromatography (20% ethyl acetate/hexane as eluant) afforded a light yellow solid. Recrystallization from pentane gave 30 g (94%) of white crystals (3). 1-Dimethylsulfamoyl-2-t-butyldimethylsilyl imidazole (3) (5.0 g, 17.3 mmol) was added to 100 mL of THF. The solution was cooled to −20° C. A solution of secondary butyl lithium (s-BuLi) in hexane (1.3M, 14.6 mL, 19 mmol) was added dropwise to the reaction flask. Upon completion the reaction was stirred for 1 h at −20° C. 8 mL of dimethylformamide (DMF) was added to the reaction and then stirred at rt for 3.5 h. The reaction was diluted with water and the organic layer separated. The organic phase was washed with brine and then dried over sodium sulfate. The mixture was filtered and the filtrate concentrated under reduced pressure. Column chromatography (20% ethyl acetate/hexane) afforded a light yellow oil. Upon cooling the product solidifies to give yellow crystals of 1-dimethylsulfamoyl-2-t-butyldimethylsilyl -5-imidazolecarboxaldehyde (4).

EXAMPLE B-1

Procedure for Preparation of 4(5)-(7-methoxy-1,2,3,4-tetrahydronaphthalen-2-ylmethyl)-1H-imidazole, hydrogen chloride salt:

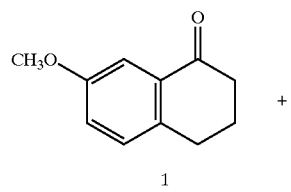

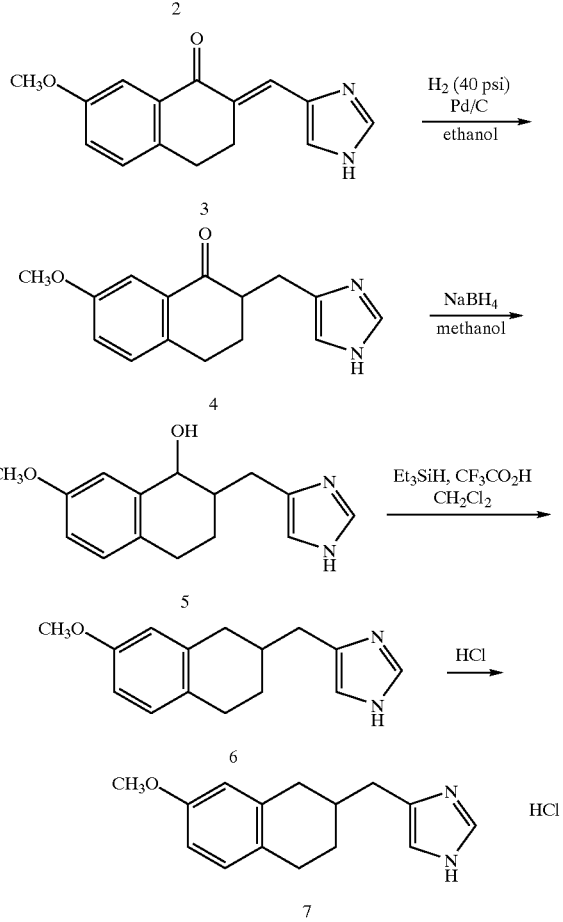

Procedure-

7-Methoxy-1-tetralone (1) (1.5 g, 8.5 mmol) and 1-dimethylsulfamoyl-2-t-butyldimethylsilyl-5-imidazolecarboxaldehyde (2) (2.7 g, 8.5 mmol) were added to 8.5 mL of a 40% solution of sulfuric acid. The reaction was heated for 24 h at 90° C. After cooling to rt, the reaction was made basic with excess concentrated ammonium hydroxide. The mixture was extracted twice with THF. The organic layers were combined and washed with brine. The organic layer was separated and dried over sodium sulfate. The mixture was filtered and the filtrate concentrated under reduced pressure to afford 2.7 g of a yellow solid (3) comprising 3-(3H-imidazole-4(5)ylmethylene)-7-methoxy chroman-4-one. The crude product was suspended in 100 mL of ethanol and a palladium on carbon catalyst (10%, 0.27 g) added. The mixture was shaken in a Parr hydrogenator apparatus while under 40 psi of hydrogen. After 19 h the reaction mixture was filtered through Celite and the filtrate concentrated under reduced pressure. Column chromatography with 7% methanol in chloroform afforded 1.05 g (46%) of a tan color solid comprising 2-[3H-Imidazole-4 (5)-ylmethyl]-7-methoxy-3,4-dihydro-2H-naphthalen-1-one (4)(B-1a). (4) (0.5 g, 1.95 mmol) was added to 20 mL of methanol. Sodium borohydride (74 mg, 1.95 mmol) was added to the solution. After stirring for 2.5 h at rt the reaction mixture was quenched with water. The reaction mixture was then extracted twice with ethyl acetate. The organic layers were combined and washed with brine. The organic layer was separated and dried over sodium sulfate. The mixture was filtered and the filtrate concentrated under reduced pressure to afford 0.5 g of a white solid (5) comprising 2-[3H-Imidazole-4(5)-ylmethyl]-7-methoxy-3,4-dihydro-2H-naphthalen-1-ol. The crude product was dissolved in 26 mL of dichloromethane. Triethylsilane (2.5 mL, 15.6 mmol) and trifluoroacetic acid (4.8 mL, 62.3 mmol) were added and the reaction stirred at rt for 22 h. The reaction was made basic with 2N NaOH and the organic layer separated and washed with brine. The solution was dried over sodium sulfate. The mixture was filtered and the filtrate concentrated under reduced pressure. Column chromatography with 7% methanol in chloroform afforded 0.39 g (83%) of a tan color oil (6). The product was dissolved in methanol and an excess of hydrogen chloride (HCl) in ether was added. The solution was concentrated under reduced pressure to yield 0.3 g of a tan color solid. Column chromatography with 7% methanol in chloroform afforded 0.25 g (46%) of 4(5)-(7-methoxy-1,2,3,4-tetrahydronaphthalen-2-ylmethyl)-1H-imidazole, hydrogen chloride salt (B-1) as white crystals (7) after recrystallization from a mixture of acetone and methanol.

$^1$H NMR (300 MHz, CD$_3$OD) 8.83 (s, 1H), 7.38 (s, 1H), 6.95 (d, 1H, J=8.5 Hz), 6.66 (d, 1H, J=8.4 Hz), 6.57 (s, 1H), 3.73 (s, 3H), 2.71–2.81 (m, 5H), 2.43–2.52 (m, 1H), 1.90–2.14 (m, 2H), 1.40–1.51 (m, 1H).

Following the procedure of Example B-1 various fused ring compounds are reacted to yield the imidazole derivatives listed below.

EXAMPLE B-2(a–d)

4-chromanone (2a) 3-(3H-imidazol-4(5)-ylmethylene)chroman-4-one
 (2b) 3-(3H-imidazol-4(5)-ylmethyl)chroman-4-one
 (2c) 3-(3H-imidazol-4(5)-ylmethyl)chroman-4-ol
 (2d) 4(5)-chroman-3-ylmethyl-1H-imidazole

EXAMPLE B-3(a–b)

1-tetralone (3a) 2-(3H-imidazol-4(5)-ylmethyl)-3,4-dihydro-2H-naphthalen-1-one
 (3b) 4(5)-(1,2,3,4-tetrahydronaphthalen-2-ylmethyl)-1H-imidazole

EXAMPLE B-4(a–b)

4-methyl-1-tetralone (4a) 4(5)-(4-methyl-1,2,3,4-tetrahydronaphthalen-2-ylmethyl)-1H-imidazole
 (4b) 2-(3H-imidazol-4(5)-ylmethyl)-4-methyl-3,4-dihydro-2H-naphthalen-1-one

EXAMPLE B-5(a–b)

Thiochroman (5a) 3-(3H-imidazol-4(5)-ylmethylene)thiochroman-4-one
 (5b) 3-(3H-imidazol-4(5)-ylmethyl)thiochroman-4-one

EXAMPLE B-6

The hydrogen chloride salt of the previous compound is prepared by step 5 of the method of Example B-1, above.
Thiochroman 4(5)-thiochroman-3-ylmethyl-1H-imidazole

EXAMPLE B-7(a–c)

1-indanone (7a) 2-(3H-imidazol-4(5)-ylmethylene)indan-1-one
 (7b) 2-(3H-imidazole-4(5)-ylmethyl)indan-1-one
 (7c) 4(5)-indan-2-ylmethyl-1H-imidazole

EXAMPLE B-8(a–b)

7-methyl-1-tetralone (8a) 2-(3H-imidazol-4(5)-ylmethyl)-7-methyl-3,4-dihydro-2H-naphthalen-1-one
 (8b) 4(5)-(7-methyl-1,2,3,4-tetrahydronaphthalen-2-ylmethyl)-1H-imidazole The hydrogen chloride salt of this compound is prepared by the method of Example B-6.

EXAMPLE B-9(a–c)

4-keto-4,5,6,7-tetra-hydrothianaphthene (9a) 4(5)-(4,5,6,7-tetrahydro-benzo[b]thiophen-5-ylmethyl)-1H-imidazole The hydrogen chloride salt of this compound is prepared by the method of Example B-6.

(9b) 5-(3H-imidazol-4(5-ylmethyl)-6,7-dihydro-5H-benzo[b]thiophen-4-one

The hydrogen chloride salt of this compound is prepared by the method of Example B-6.

(9c) 5-(octahydrobenzo[b]thiophen-5-ylmethyl)-1H-imidazole

EXAMPLE B-10

4,4-Dimethyl-1-tetralone 4(5)-(4,4-dimethyl-1,2,3,4-tetrahydronaphthalen-2-ylmethyl)-1H-imidazole

EXAMPLE B-11(a–b)

1-Benzosuberone (11a) 4(5)-(6,7,8,9-tetrahydro-5H-benzocyclohepten-6-ylmethyl)-1H-imidazole
 (11b) 6-(1H-imidazol-4(5)-ylmethylene)-6,7,8,9-tetrahydrobenzocyclohepten-5-one

EXAMPLE C-1

Procedure for Preparation of 4(5)-thiophen-3-ylmethyl-1H-imidazole:

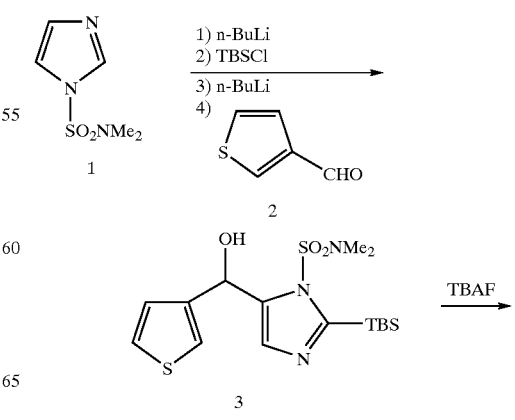

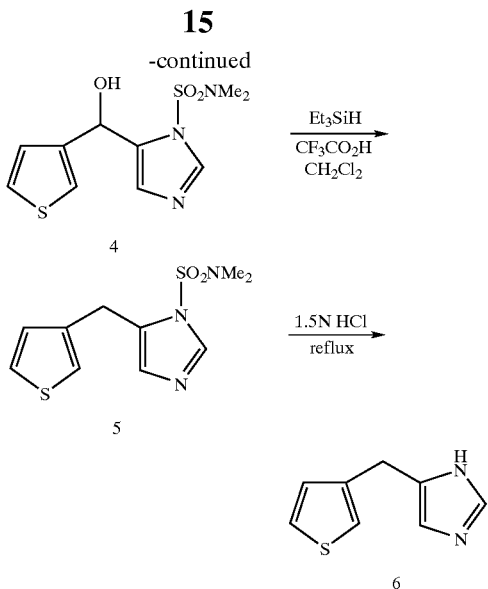

Procedure- 1-(Dimethylsulfamoyl)imidazole (1) (2.0 g, 11.4 mmol) is taken up in 42 mL of anhydrous THF and cooled to −78° C. n-BuLi (6.6mL, 10.6 mmol) is added dropwise to the solution of (1). The resultant solution is stirred at −78° C. for 30 min. Tert-butyldimethylsilylchloride (TBSCl) (1.6 g, 10.6 mmol) in 8 mL of THF is added to the reaction. The reaction is warmed to rt and stirred overnight. The next day the reaction is cooled to −20° C. and 7.3 mL (11.6 mmol) of n-BuLi added. After stirring at −20° C. for 45 min, 3-thiophene carboxaldehyde (2) (1.0 mL, 11.6 mmol) is added to the reaction mixture. Then reaction is warmed to rt and stirred overnight. The next day the reaction is quenched with water and diluted with ethyl acetate. The organic layer is washed with water followed by brine. The organic phase is dried over sodium sulfate and the solvent removed under reduced pressure. Flash chromatography (2:5 ethyl acetate/hexane) affords 3.0 g (7.5 mmol) of 2-(t-butyldimethylsilyl)-5-(hydroxythiophen-2-ylmethyl)imidazole-1-sulfonic acid dimethylamide (3). (3) (1.5 g, 3.74 mmol) is taken up in 37 mL of THF. A 1M solution of tetra-n-butylammonium fluoride (TBAF) in THF (4.1 mL, 4.1 mmol) is added dropwise to the solution of (3). The reaction is stirred overnight at rt. The next day the reaction is quenched with water and then extracted with ethyl acetate. The organic layer is washed with water followed by brine. The organic phase is dried over sodium sulfate and the solvent removed under reduced pressure. 0.94 g (3.3 mmol) of 5-(hydroxythiophen-2-ylmethyl)imidazole-1-sulfonic acid dimethylamide (4) is recovered. (4) (0.5 g, 1.74 mmol) is taken up in 23 mL of dichloromethane, to the solution is added 2.2 mL (13.9 mmol) of triethylsilane and 4.3 mL (55.7 mmol) of trifluoroacetic acid. The reaction is stirred at rt overnight and then quenched with water and neutralized with solid sodium bicarbonate. The organic layer is washed with water followed by brine. The organic phase is dried over sodium sulfate and the solvent removed under reduced pressure. Flash chromatography using a 1:1 mixture of ethyl acetate and hexane affords 0.42 g (1.55 mmol) of 5-(thiophen-2-ylmethyl)imidazole-1-sulfonic acid dimethylamide (5). (5) (0.42 g, 1.55 mmol) is taken up in 10 mL of a 1.5N HCl solution and heated at reflux for 3 h and then stirred at rt overnight. The reaction is diluted with ethyl acetate, neutralized with solid sodium bicarbonate and then made basic with 2N NaOH. The organic layer is washed with water followed by brine. The organic phase is dried over sodium sulfate and the solvent removed under reduced pressure. Flash chromatography using a 10:1 mixture of chloroform and methanol affords 0.17 g (1.0 mmol) of 4(5)-thiophen-3-ylmethyl-1H-imidazole (6) (C-1).

$^1$H NMR (300 MHz, CD$_3$OD) 7.52 (s, 1H), 7.25–7.27 (m, 1H), 6.96–7.01 (m, 2H), 6.77 (s, 1H), 3.98 (s, 2H).

EXAMPLE C-2

The 2-carboxaldehyde isomer of 3-thiophene carboxaldehyde is substituted into the method of Example C-1 to yield 4(5)-thiophen-2-ylmethyl-1H-imidazole

EXAMPLE C-3

5-Methyl-2-thiophene carboxaldehyde of 3-thiophene carboxaldehyde is substituted into the method of Example C-1 to yield 4(5)-(5-methylthiophen-2-ylmethyl)-1H-imidazole

EXAMPLE C-4

5-Chloro-2-thiophene carboxaldehyde of 3-thiophene carboxaldehyde is substituted into the method of Example C-1 to yield 4(5)-(5-chlorothiophen-2-ylmethyl)-1H-imidazole

EXAMPLE C-5

2-Furan carboxaldehyde is substituted into the method of Example C-1 to yield 4 (5)-furan-2-ylmethyl-1H-imidazole

EXAMPLE C-6

3-Furan carboxaldehyde is substituted into the method of Example C-1 to yield 4(5)-furan-3-ylmethyl-1H-imidazole

EXAMPLE C-7

5-Methyl-2-furan carboxaldehyde is substituted into the method of Example C-1 to yield 4(5)-(5-methylfuran-2-ylmethyl)-1H-imidazole

EXAMPLE C-8

Benzaldehyde is substituted into the method of Example C-1 to yield 4(5)-benzyl-1H-imidazole

EXAMPLE C-9

2-Thianaphthene carboxaldehyde is substituted into the method of Example C-1 to yield 4(5)-benzo[b]thiophen-2-ylmethyl-1H-imidazole

EXAMPLE C-10

2-Benzofuran carboxaldehyde is substituted into the method of Example C-1 to yield 4(5)-benzofuran-2-ylmethyl-1H-imidazole

EXAMPLE C-11

5-Ethyl-2-furan carboxaldehyde is substituted into the method of Example C-1 to yield 4(5)-(5-ethylfuran-2-ylmethyl)-1H-imidazole

EXAMPLE C-12

4-Bromo-2-thiophene carboxaldehyde is substituted into the method of Example C-1 to yield 4(5)-(4-bromothiophen-2-ylmethyl)-1H-imidazole

EXAMPLE C-13

4-Phenyl-2-thiophene carboxaldehyde is substituted into the method of Example C-1 to yield 4(5)-(4-phenylthiophen-2-ylmethyl)-1H-imidazole

EXAMPLE C-14

4-Methyl-2-thiophene carboxaldehyde is substituted into the method of Example C-1 to yield 4(5)-(4-methylthiophen-2-ylmethyl)-1H-imidazole, hydrochloride salt

EXAMPLE D-1
Procedure for Preparation of oxazolidin-2-ylidene-(3-phenyl bicyclo[2.2.1]hept-2-yl) amine:

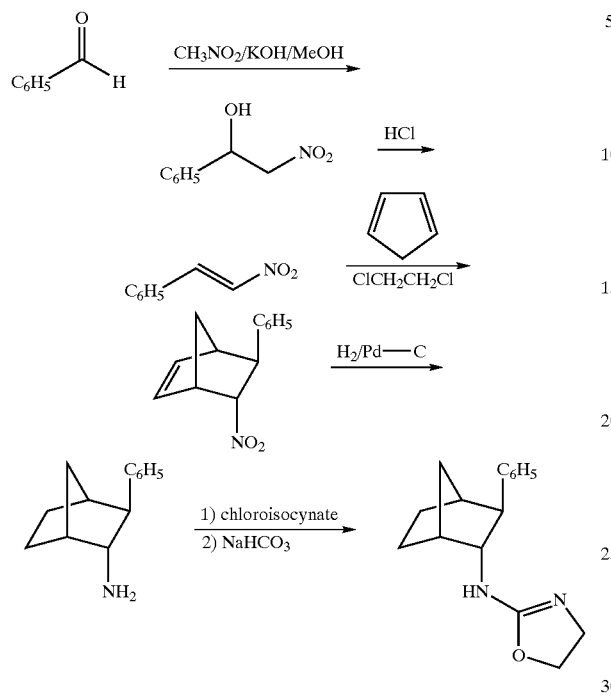

Procedure-

The endo exo relative stereochemistry of the compound was prepared, by making the β-nitrostyrene as shown above. Treatment of a methanol solution of benzaldehyde (10 g, 94.3 mmole) with nitromethane (51 ml, 943 mmol) in the presence of sodium hydroxide (3N in methanol to pH=8) afforded the nitro alcohol in 60% yield. Dehydration of the alcohol was effected by treatment with methanesulfonyl chloride (3.56 g, 31.1 mmole) followed by triethylamine (6.3 g, 62.2 mmol) in dichloromethane (35 ml) to give 97% yield of product. Kugelrohr distillation was done to purify compound. Construction of the bicyclo[2.2.1]heptane skeleton was carried out in one step. The Diels-Alder reaction was conducted by warming the nitrostyrene (4.5 g, 30.2 mmole) with cyclopentadiene (3.98 g, 60.4 mmole) in 1,2-dichloroethane (10 ml). The Diels-Alder reaction proceeds in approximately a 3:1 endo:exo nitro ratio. Both the ratio and relative stereochemistry was demonstrated through x-ray analysis. Reduction of both the nitro group and the olefin was carried out under an atmosphere of hydrogen in the presence of 10% by weight palladium on charcoal. Separation of isomers was conveniently carried out at this stage using flash chromatography with 5% ammonia-saturated methanol in dichloromethane. The amine (0.7 g, 3.74 mmole) was treated first with chloroethylisocyanate (0.38 ml, 4.49 mmole) to afford the chloroethylurea, which was then warmed in the presence of aqueous NaHCO₃ solution to afford oxazolidin-2-ylidene-(3-phenyl bicyclo [2.2.1]hept-2-yl) amine (D-1) in 51% yield.

¹H NMR (300 MHz, CDCl₃) d 1.36–1.80 (m, 6H), 2.14 (d, 1H, J=4.40 Hz), 2.37 (s, 1H), 2.65 (s, 1H), 3.71–3.78 (m, 2H), 3.95–3.98 (m, 1H), 4.19–4.25 (t, 2H, J=17.15 Hz, J=8.36 Hz), 7.17–7.29 (m, 5H).

EXAMPLE D-2
Oxazolidin-2-ylidene-(3-o-tolyl bicyclo[2.2.1]hept-2-yl) amine is prepared by substituting o-methyl β-nitrostyrene in the method of D-1

EXAMPLE D-3
Bicyclo[2.2.1]hept-2-yl oxazolidin-2-ylidene amine is prepared by substituting nitroethene in the method of D-1

EXAMPLE E-1
Procedure for Preparation of imidazolidin-2-ylidene-(4-methyl-3,4-dihydro-2H-benzo [1,4]oxazin-6-yl)amine:

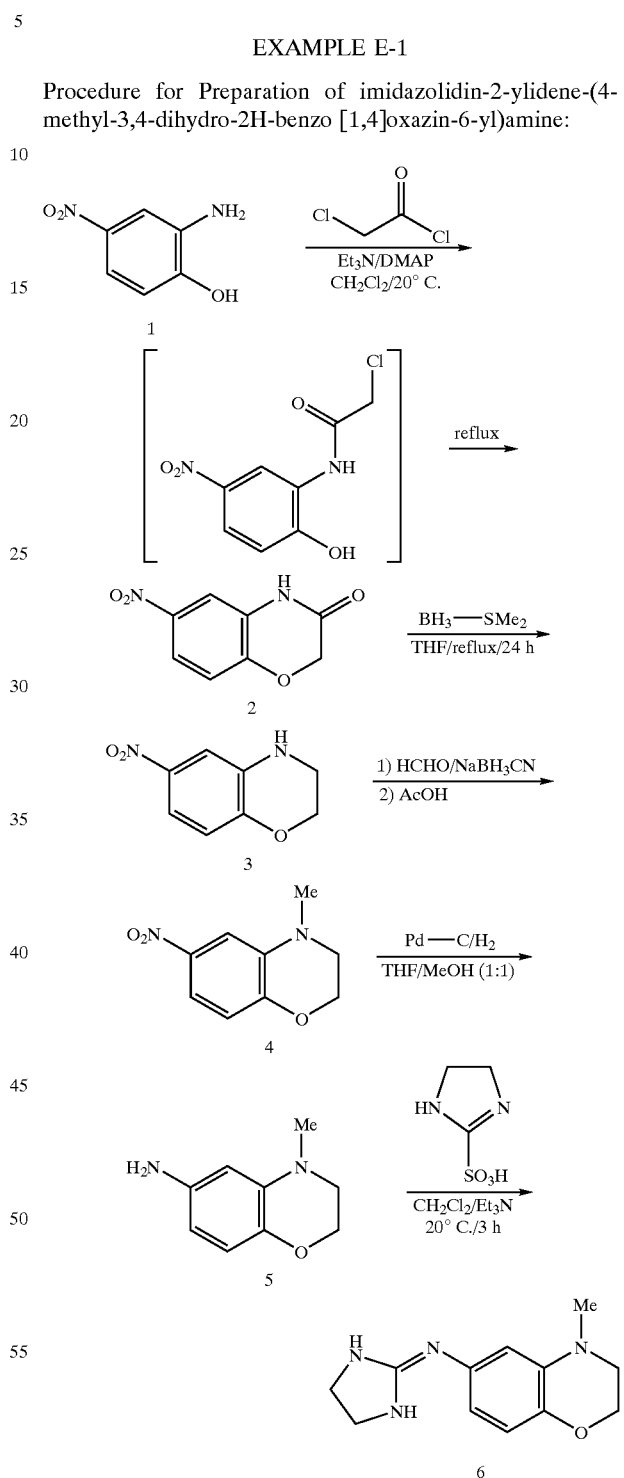

Procedure-

To 2-amino-4-nitrophenol (1) (4.00 g, 25.95 mmol), triethylamine (15.20 mL, 109.0 mmol) and 4-dimethylaminopyridine (0.063 g, 0.52 mmol) slurried in anhydrous CH₂Cl₂ (250 mL) at 0° C. under argon added chloroacetyl chloride (2.27 mL, 28.55 mmol) via syringe. After refluxing for 72 h pure product was filtered off and washed with water. The mother liquor was washed successively with phosphoric acid (0.5M), saturated sodium bicarbonate, water and brine and then dried over MgSO$_4$. This solution was adhered to silica and purified by flash chromatography on silica with hexane/ethyl acetate (4:6) to give additional product. The combined solids were dried in vacuo to give pure 6-nitro4H-benzo[1,4]oxazin-3-one (2) (4.12 g) in 82% yield. To a slurry of (2) (1.49 g, 7.65 mmol) in anhydrous THF (40 mL) under argon in a 2-neck round-bottom flask equipped with a reflux condenser was added borane-dimethyl sulfide complex (15.3 mL, 30.62 mmol). The mixture was heated at reflux until starting material was no longer observed via thin layer chromatography (2 h). The reaction mixture was cooled to rt and carefully quenched by the dropwise addition of methanol. The resulting mixture was then refluxed an additional 10 minutes. The crude reaction mixture was concentrated in vacuo and purified by flash chromatography on silica with hexane/ethyl acetate (8:2) to give pure 6-nitro-3,4-dihydro-2H-benzo[1,4] oxazine (3) (1.36 g) as an orange solid in 99% yield. To (3) (0.032 g, 0.178 mmol) and formalin (37% in H$_2$O, 0.20 mL, 2.67 mmol) in anhydrous acetonitrile (1.5 mL) at ambient temperature was added sodium cyanoborohydride (0.034 g, 0.534 mmol). This solution was stirred for 30 min before adding glacial acetic acid (0.032 mL, 0.534 mmol). The resulting mixture was stirred an additional 16 h. The organics were taken up in diethyl ether and washed successively with NaOH (2N) and brine, dried over MgSO$_4$ and concentrated in vacuo. The resulting solids were purified by flash chromatography on silica with hexane/ethyl acetate (7:3) to give pure 4-methyl-6-nitro-3,4-dihydro-2H-benzo[1,4] oxazine (4) (0.031 g) in 93% yield. To (4) (2.16 g, 11.12 mmol) and 10% palladium on carbon (0.216 g, 10 wt. %) under argon was added methanol (MeOH) (30 mL) followed by THF (30 mL). Hydrogen was bubbled thru the resulting slurry until no (4) remained visible by thin layer chromatography (2 h). Celite was added and the mixture was filtered through a bed of celite followed by a MeOH wash. The resulting solution was concentrated in vacuo to give pure 4-methyl-3,4-dihydro-2H-benzo[1,4]oxazin-6-ylamine (5) (1.86 g) as a pale purple oil in 100% yield which was carried on without further purification. To (5) (1.86 g, 11.34 mmol) and imnidazoline-2-sulfonic acid (1.84 g, 12.24 mmol) in anhydrous acetonitrile (50 mL) under argon at 0° C. was added triethylamine (3.26 mL, 23.36 mmol). This solution was gradually warmed to ambient temperature and stirred for 16 h. At that time an additional amount of imidazoline-2-sulfonic acid (0.86 g, 5.55 mmol) was added and the resulting mixture was stirred an additional 5 h. This solution was concentrated in vacuo and the residues were taken up in H$_2$O. The organics were extracted into CH$_2$Cl$_2$ and washed twice with NaOH and then brine, dried over MgSO$_4$ and concentrated in vacuo. The resulting foam was purified by flash chromatography on silica with 20% methanol (saturated with ammonia) in chloroform to give pure imidazolidin-2-ylidene-(4-methyl-3,4-dihydro-2H-benzo[1, 4]oxazin-6-yl)amine (6) (E-1) (0.905 g) in 34% yield.

$^1$H NMR (CDCl$_3$): 2.81 (s, 3H); 3.26 (t, J=8.9 Hz, 2H); 3.60 (s, 4H); 4.26 (m, 2H); 4.60 (vbrs, 2H); 6.34 (dd, J=8.2 Hz, J=2.4 Hz, 1H); 6.39 (d, J=2.4 Hz, 1H); 6.68 (d, J=8.2 Hz, 1H).

EXAMPLE F & G

Procedure for Preparation of 6-(imidazolidin-2-ylidene amino)-5-methyl-4H-benzo[1,4]oxazin-3-one (F) and Imidazolidin-2-ylidene-(5-methyl-3,4-dihydro-2H-benzo[1, 4]oxazin-8-yl)amine (G):

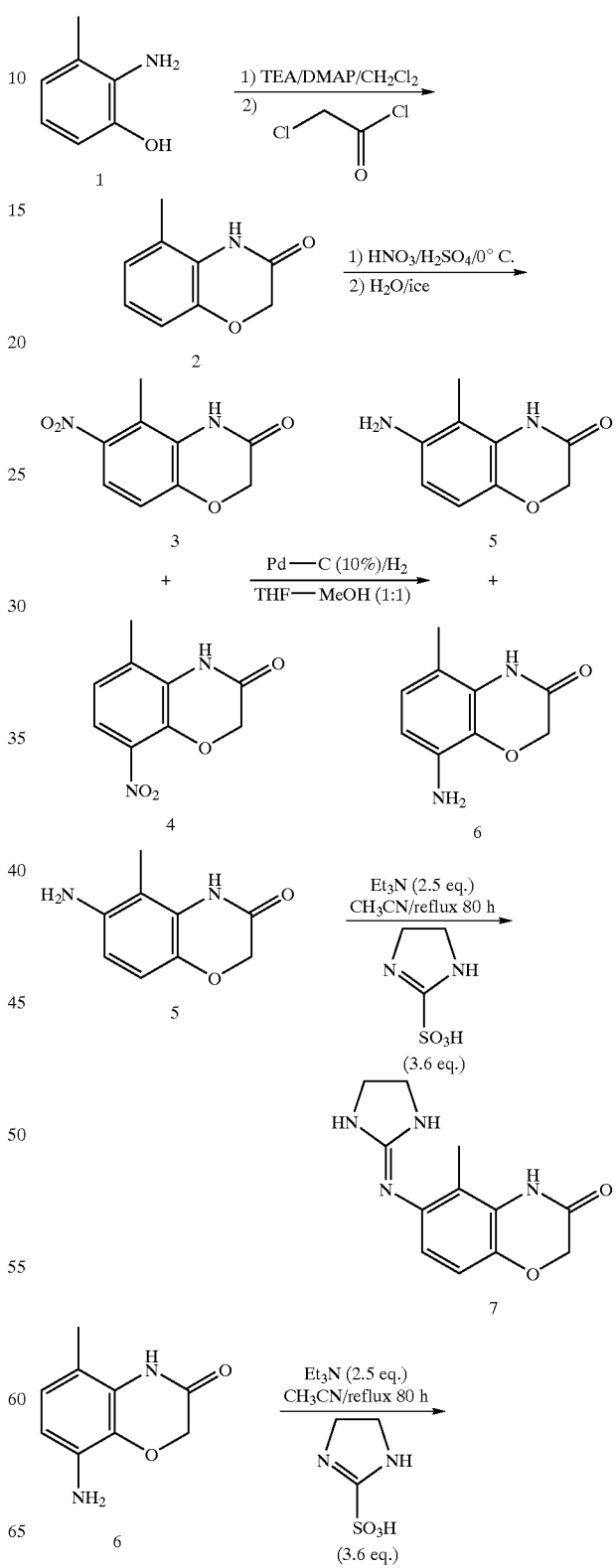

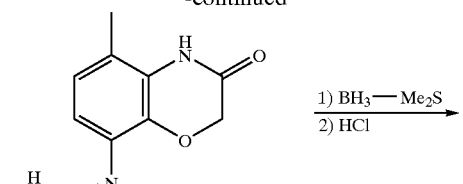

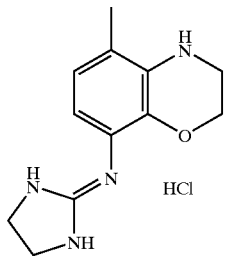

Procedure-

To 2-amino-3-methylphenol (1) (14.72 g, 0.120 mol), triethylamine (35.0 mL, 0.251 mol) and 4-dimethylaminopyridine (0.29 g, 2.39 mmol) in anhydrous $CH_2Cl_2$ (100 mL) at 0° C. under argon was added chloroacetyl chloride (10.0 mL, 0.126 mol) dropwise via syringe. After the addition was complete the resulting solution was refluxed for 24 h. The organics were washed successively with phosphoric acid (0.5M), saturated sodium bicarbonate, water and brine and then dried over $MgSO_4$. The resulting solution was concentrated and taken up in THF to which ether was added. The resulting crystals were filtered off to give pure 5-methyl-4H-benzo[1,4]oxazin-3-one (2) (12.30 g) in 63% yield. To (2) (14.64 g, 89.72 mmol) dissolved in concentrated $H_2SO_4$ (65 mL) at −10° C. was added 70% concentrated $HNO_3$ (8.08 g, 89.72 mmol) in concentrated $H_2SO_4$ (25 mL) with rapid mechanical stirring at a rate whereby the internal temperature was maintained below −5° C. As soon as the addition was complete the mixture was poured onto crushed ice (500 mL) and the resultant solids were filtered off and slurried in cold water (300 mL) while sufficient NaOH was added to adjust the pH to 7. The recovered yellow powder was dissolved in THF, adhered to silica and purified by flash chromatography with 60% hexane and ethyl acetate to give the nitrated product as a mixture of two regioisomers, i.e. the desired 6-substituted aromatic comprising 6-nitro-5-methyl-4H-benzo[1,4] oxazin-3-one (3) (55%) and the 8-substituted by-product comprising 8-nitro-5-methyl-4H-benzo[1,4]oxazin-3-one (4) (22%). These isomers are separated with difficulty at this point and were carried on to the next step as a mixture. To a mixture of (3) (1.93 g, 9.27 mmol) and (4) (0.48 g, 2.32 mmol) dissolved in a solution of MeOH (300 mL) and THF (300 mL) under argon was added 10% palladium on carbon (1.20 g). The resulting solution was subjected to $H_2$ at one atmosphere pressure. After 16 h the catalyst was filtered off and the resulting solution was concentrated in vacuo and purified by flash chromatography on silica with 50% hexane and ethyl acetate to give 6-amino-5-methyl-4H-benzo[1,4] oxazin-3-one (5) (0.96 g) in 46% yield and 8-amino-5-methyl-4H-benzo[1,4]oxazin-3-one (6) (0.17 g) in 8% yield. (5) (1.20 g, 6.74 mmol), imidazoline-2-sulfonic acid (2.02 g, 13.48 mmol) and triethylamine (2.35 mL, 16.85 mmol) were heated at reflux in anhydrous acetonitrile (50 mL) under argon for 48 h. At that time an additional amount of imidazoline-2-sulfonic acid (1.01 g, 6.74 mmol) and triethylamine (1.41 mL, 10.12 mmol) were added and the resulting mixture was stirred an additional 24 h. This solution was concentrated in vacuo and the residues were taken up in a solution of $CHCl_3$/isopropyl alcohol (3:1) and washed successively with NaOH (1N) and brine, dried over $MgSO_4$ and concentrated in vacuo. The resulting foam was purified by flash chromatography on silica with 20% methanol saturated with ammonia in chloroform to give 6-(imidazolidin-2-ylideneamino)-5-methyl-4H-benzo[1,4]oxazin-3-one (7) (0.42 g) as a foam in 27% yield along with 55% recovered starting material. The HCl salt was recrystallized from a mixture of ethanol and diethyl ether ($EtOH/Et_2O$) to give fine white needles.

$^1$H NMR (DMSO): 2.10 (s, 3H); 3.59 (s, 4H); 4.53 (s, 2H); 6.83 (d, J=8.6 Hz, 1H); 6.90 (d, J=8.6 Hz, 1H); 8.07 (brs, 2H); 10.15 (vbrs, 1H); 10.42 (s, 1H). (6) (0.222 g, 1.35 mmol), imidazoline-2-sulfonic acid (0.223 g, 1.49 mmol) and triethylamine (0.415 mL, 2.98 mmol) were heated at 95° C. in anhydrous acetonitrile (10 mL) in a sealed tube for 2 h. At that time an additional amount of imidazoline-2-sulfonic acid (0.112 g, 0.75 mmol) was added and the reaction was continued for an additional 16 h. This solution was concentrated in vacuo and the residues were taken up in a solution of $CHCl_3$/isopropyl alcohol (3:1) and washed successively with NaOH (2N) and brine, dried ($MgSO_4$) and concentrated in vacuo. The resulting oil was recrystalizied from $CHCl_3$ to give pure 6-(imidazolidin-2-ylideneamino)-5-methyl-4H-benzo[1,4]oxazin-3-one (8) (F) (0.048 g) as a white powder in 15% yield along with 35% recovered starting material. To a slurry of (8), (0.08 g, 0.321 mmol) in anhydrous THF (50 mL) under argon in a 3-neck round-bottom flask equipped with reflux condenser was added borane-dimethyl sulfide complex (0.48 mL, 0.936 mmol). The mixture was heated at reflux until starting material was no longer observed via thin layer chromatography (3 h). The reaction mixture was cooled to room temp-erature and carefully quenched by the dropwise addition of methanol. The crude reaction mixture was concentrated in vacuo and purified by flash chromatography on silica using 20% methanol saturated with ammonia/chloroform to give imidazolidin-2-ylidene-(5-methyl-3,4-dihydro-2H-benzo[1, 4]oxazin-8-yl)amine (9) (G) (0.03 g) as the HCl salt in 37% yield.

$^1$H NMR ($CDCl_3$): 2.07 (s, 3H); 3.46 (t, J=4.3 Hz, 2H); 3.55 (s, 4H); 4.24 (t, J=4.3 Hz, 2H); 5.60 to 5.95 (vbrs, 2H); 6.44 (d, J=8.0 Hz, 1H); 6.57 (d, J=8.0 Hz, 1H).

EXAMPLE H

Procedure for Preparation of 4(5)-phenylsulfanyl-1H-imidazole:

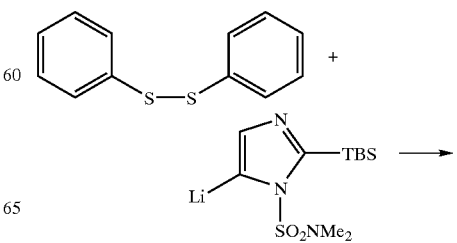

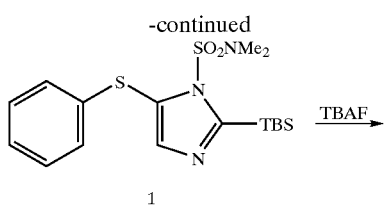

EXAMPLE I

Procedure for Preparation of 4(5)-(1,2,3,4-tetrahydronaphthalen-2-ylmethyl)-4,5-dihydro-1H-imidazole, methane sulfonic acid salt:

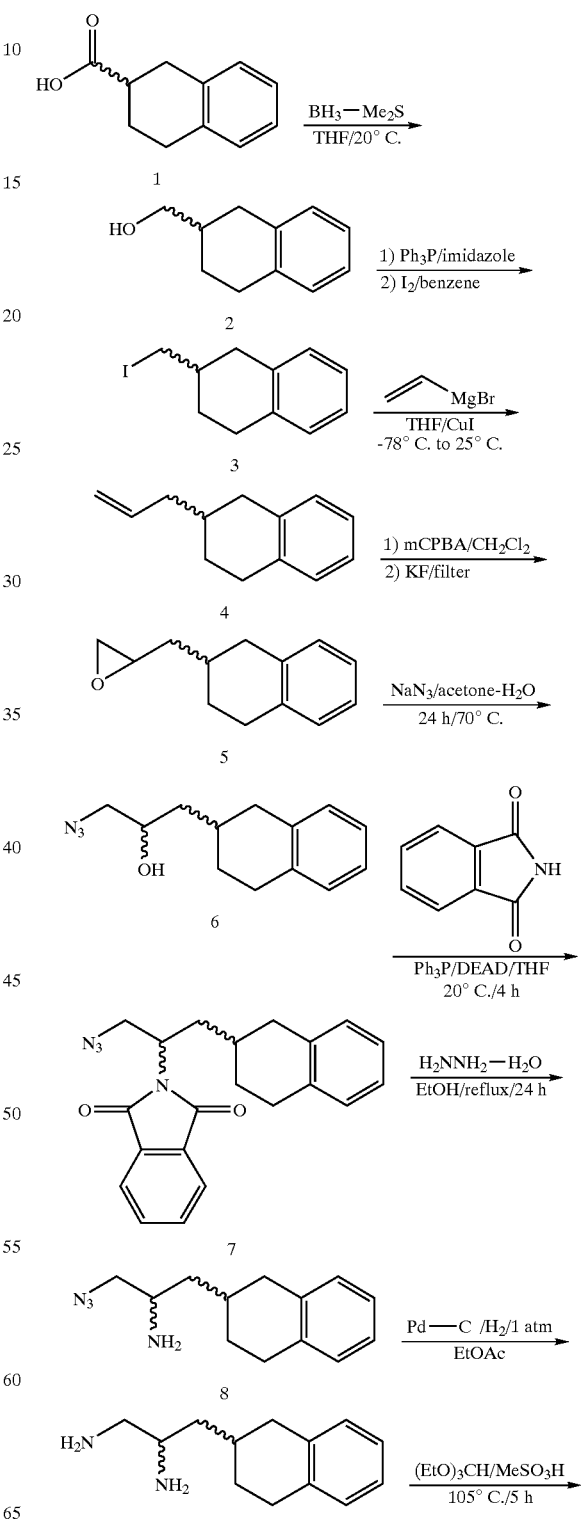

Procedure- 1-(N,N-dimethylsulfamoyl)imidazole (1.5 g, 8.6 mmol) was taken up in 28 mL of THF. The solution was cooled to −78° C. and n-BuLi (5.4 mL, 8.6 mmol) added dropwise via syringe. After stirring at −78° C. for 1 h TBSCl (1.3 g, 8.56 mmol) in 10 mL of THF was added. The bath was removed and the reaction allowed to warm-up to rt. The reaction mixture was stirred overnight. The reaction mixture was cooled to −20° C. and n-BuLi (5.4 mL, 8.6 mmol) added. After 45 min phenyldisulfide (1.9 g, 8.6 mmol) in 8 mL of THF was added. The reaction mixture was stirred at rt for 48 h. The reaction mixture was quenched with saturated ammonium chloride and extracted with ethyl acetate. The organic layer was collected and washed with water and then brine. The solution was dried over sodium sulfate and the solvent removed under reduced pressure. Flash chromatography (2.5% EtOAc/hexane) afforded 2.8 g (7.0 mmol) of 2-(t-butyldimethylsilyl)-5-phenylsulfanylimidazole-1-sulfonic acid dimethylamide (1) as a yellow color oil. The compound (1) (2.8 g, 7.0 mmol) was dissolved in THF and the solution cooled to 0° C. TBAF (7.0 mL, 7.0 mmol) was added dropwise to the solution. The reaction mixture was stirred overnight at rt. The next day the reaction was quenched with water and extracted with ethyl acetate. The organic layer was washed with water followed by brine. The solution was dried over sodium sulfate and the solvent removed under reduced pressure. Flash chromatography (50% EtOAc/hexane) afforded 474 mg of 5-phenylsulfanylimidazole-1-sulfonic acid dimethylamide (2) and 290 mg of 5-phenylsulfanyl-1H-imidazole (3) (H). The 478 mg of (2) was added to 2N HCl and the solution heated at reflux for 2 h. The reaction mixture was made basic with 2N NaOH and extracted with ethyl acetate. The organic layer was washed with water followed by brine. The solution was dried over sodium sulfate and the solvent removed under reduced pressure. Flash chromatography (EtOAc) afforded (3) as a white crystalline solid. A combined total of 360 mg (2.0 mmol) of (3) is recovered.

$^1$H NMR (300 MHz, CD$_3$OD) 7.91 (s, 1H), 7.37 (s, 1H), 7.19–7.23 (m, 2H), 7.07–7.11 (m, 3H).

-continued

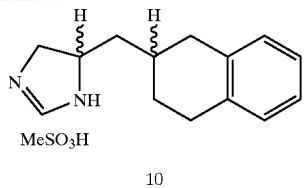

Procedure-

To 1,2,3,4-tetrahydronaphthalene-2-carboxylic acid (1) (4.93 g, 27.42 mmol in anhydrous THF (250 mL) at 20° C. under argon was added 3.26 mL (32.90 mmol) borane-dimethylsulfide ($BH_3$-$Me_2S$) via syringe.

After stirring for 16 h MeOH (4 mL) was added and the mixture was warmed to 55° C. until no more gas was evolved. The mixture was concentrated to an oil, taken up in $Et_2O$ and washed successively with 2M phosphoric acid, saturated sodium bicarbonate, water and brine and then dried over $MgSO_4$ and reconcentrated. The resulting oil was purified by high vacuum Kugelrohr at 150° C. to give pure alcohol (1,2,3,4-tetrahydronaphthalen-2-yl)methanol (2) (4.09 g) in 93% yield. To triphenylphosphine (10.179 g, 38.809 mmol) and imidazole (2.64 g, 38.809 mmol) in anhydrous benzene (175 mL) was added the iodine (8.60 g, 33.865 mmol) in benzene (75 mL) with rapid stirring followed by (2) in benzene (50 mL). After 3 h the solids were filtered off and the filtrate was reduced in vacuo to a volume of 50 mL to which was added hexane (200 mL). The resultant solids were filtered off and the filtrate was washed successively with water and brine, dried over $MgSO_4$ and concentrated in vacuo. The resulting oil was purified by flash chromatography on silica with hexane to give pure 2-iodomethyl-1,2,3,4-tetrahydronaphthalene (3) (6.239 g) in 90% yield. To (3) (10.02 g, 36.85 mmol) and CuI (1.41 g, 7.37 mmol) in anhydrous THF (50 mL) at −78° C. under argon was added vinylmagnesium bromide (1M in THF, 73.70 mL, 73.70 mmol) slowly at a speed at which no color developed. This solution was allowed to warm to 0° C. and stirred for 6 h. The resulting mixture was recooled to −40° C. and quenched by the careful addition of 2M phosphoric acid (35 mL). This solution was diluted with 100 mL water and extracted with hexanes. The organic fractions were washed successively with water and brine, dried over $MgSO_4$ and concentrated in vacuo. The resulting oil was purified by flash chromatography on silica with hexane to give 2-allyl-1,2,3,4-tetrahydronaphthalene (4) (5.618 g) in 88% yield. (4) (5.615 g, 32.645 mmol) and meta-chloroperbenzoic acid (m-CPBA) (14.08 g, 81.613 mmol) were stirred in anhydrous methylene chloride (50 mL) for 16 h. The solids were filtered off and potassium flouride KF (5.11 g, 88.142 mmol) was added and this mixture was stirred an additional hour. The solids were filtered off and the reaction was concentrated in vacuo. The resulting oil was purified by flash chromatography on silica with 5% ethyl acetate in hexane to give 2-(1,2,3,4-tetrahydronaphthalen-2-ylmethyl)oxirane (5) (5.41 g) in 88% yield. To (5) (1.626 g, 8.649 mmol) in a solution of acetone (20 mL) and water (5 mL) was added sodium azide (1.97 g, 30.271 mmol). This solution was warmed to 85° C. and stirred for 48 h. The solution was concentrated in vacuo and the residues were taken up in $CHCl_3$ and washed successively with water and brine, dried over $MgSO_4$ and concentrated in vacuo. The resulting oil was purified by flash chromatography on silica with 30% ethyl acetate in hexane to give pure 1-azido-3-(1,2,3,4-tetrahydronaphthalen-2-yl)propan-2-ol (6) (1.762 g) in 88% yield. A mixture of (6) (1.88 g, 8.140 mmol), triph-enylphosphine (2.67 g, 10.173 mmol), phthalimide (1.50 g, 10.173 mmol), diethyl azodicarboxylate (DEAD) (1.77 g, 10.173 mmol) were stirred in anhydrous THF (50 mL) for 4 h. This solution was concentrated in vacuo, taken up in a solution of hexane (25 mL) and ether (25 mL) and stirred for 16 h. The solids were filtered off and the filtrate was concentrated in vacuo. The resulting oil was purified by flash chromatography on silica with 20% ethyl acetate in hexane to give 2-[1-azidomethyl-2-(1,2,3,4-tetrahydronaphthalen-2-yl)ethyl]isoindole-1,3-dione (7) (2.487 g) contaminated with a small amount of impurity which was carried on without further purification. A mixture of (7) (3.93 g, 10.917 mmol) and hydrazine (0.680 mL, 21.833 mmol) were heated in ethanol (60 mL) at reflux for 16 h. The solids were filtered off and the filtrate was concentrated in vacuo. The residues were purified by flash chromatography on silica with 5% MeOH in $CH_2Cl_2$ to give 1-azidomethyl-2-(1,2,3,4-tetrahydronaphthalen-2-yl)ethylamine (8) (2.057 g) in 88% yield. A mixture of (8) (2.056 g, 8.940 mmol) and 10% palladium on carbon (0.260 g) were stirred in MeOH (30 mL) under 1 atmosphere of hydrogen for 16 h. The solids were filtered off and the filtrate was concentrated in vacuo. The residues were purified by flash chromatography on silica with 10% ammonia saturated MeOH in $CH_2Cl_2$ to give 3-(1,2,3,4-tetrahydro-naphthalen-2-yl)propane-1,2-dione (9) (1.557 g) in 85% yield. A mixture of (9) (0.590 g, 2.892 mmol) and methanesulfonic acid (0.980 mL, 14.460 mmol) were heated in triethylorthoformate (10 mL) at 105° C. 3 h. The reaction was concentrated in vacuo and the solids were filtered off. Subsequent recrystalization of these solids from a mixture of MeOH and ether gave pure 4(5)-(1,2,3,4-tetrahydronaphthalen-2-ylmethyl)-4,5-dihydro-1H-imidazole, methane sulfonic acid salt (I) (0.435 g) in 48% yield.

$^1$H NMR (CDCl$_3$): 1.37 to 1.56 (m, 1H); 1.56 to 1.70 (m, 1H); 1.80 to 2.02 (m, 2H); 2.32 to 2.55 (m, 2H); 2.72 (s, 3H); 2.75 to 2.95 (m, 3H); 3.48 to 3.59 (m, 1H); 3.93 to 4.08 (m, 1H); 4.31 to 4.47 (m, 1H); 7.00 to 7.20 (m, 4H); 8.46 (s, 1H); 10.04 (s, 1H); 10.35 (brs, 1H).

EXAMPLE J-1

Procedure for Preparation of 4(5)-cyclohexylmethyl-1H-imidazole:

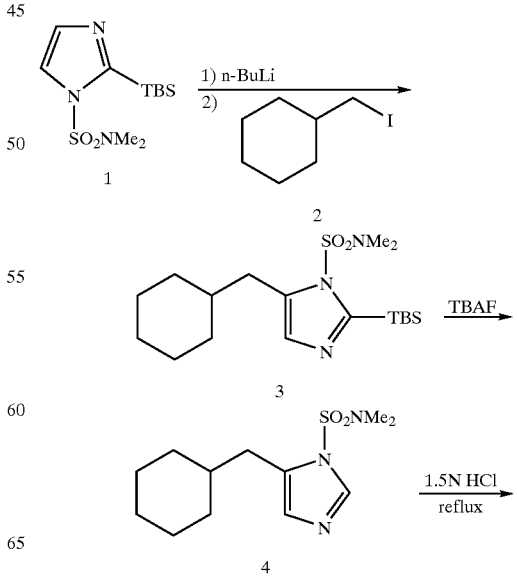

-continued

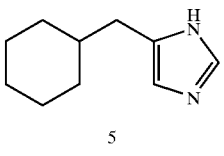

5

Procedure-

2-Tert-butyldimethylsilyl-1-dimethylsulfamoyl imidazole (1) (4.1 g, 14.2 mmol) is taken up in 47 mL of anhydrous THF and cooled to −20° C. n-BuLi (8.9 mL, 14.2 mmol) is added dropwise to the solution of (1). The resultant solution is stirred at −20° C. for 45 min. Cyclohexylmethyl iodide (2) (3.14 g, 14 mmol) is then added dropwise to the reaction mixture. Then reaction is warmed to rt and stirred overnight. The next day the reaction is quenched with saturated ammonium chloride and diluted with water. The mixture is extracted with ethyl acetate (3×100 mL). The organic layers are combined and washed with water followed by brine. The organic phase is dried over sodium sulfate and the solvent removed under reduced pressure. Flash chromatography (4:1 ethyl acetate/hexane) affords 2.26 g (5.6 mmol) of 5-cyclohexylmethyl-2-tert-butyldimethylsilyl-1-dimethylsulfamoyl imidazole (3). (3) (2.26 g, 5.6 mmol) is taken up in 56 mL of THF and cooled to 0° C. A 1M solution of TBAF in THF (5.6 mL, 5.6 mmol) is added dropwise to the solution of (3). The reaction is warmed to rt and stirred overnight. The next day the reaction is quenched with water and then extracted with ethyl acetate. The organic layer is washed with water followed by brine. The organic phase is dried over sodium sulfate and the solvent removed under reduced pressure. Flash chromatography (1:1 ethyl acetate/hexane) affords 1.2 g (4.42 mmol) of 5-cyclohexylmethyl-1-dimethylsulfamoyl imidazole (4). (4) (1.2 g, 4.42 mmol) is taken up in 25 mL of a 1.5N HCl solution and heated at reflux for 2 h. The reaction is cool to rt and diluted with ethyl acetate. The mixture is brought to pH 13 with 2N NaOH and then extracted with chloroform (4×100 mL). The organic layers are combined and washed with water followed by brine. The organic phase is dried over sodium sulfate and the solvent removed under reduced pressure. Flash chromatography (9:1 chloroform/methanol) affords 700 mg (4.27 mmol) of 4(5)-cyclohexylmethyl-1H-imidazole (5) (J-1).

$^1$H NMR (CDCl$_3$): 0.92 to 1.0 (m, 2H); 1.16 to 1.26 (m, 3H); 1.57 to 1.73 (m, 6H); 2.48 (d, J=6.9 Hz, 2H); 6.77 (s, 1H); 7.56 (s, 1H)

EXAMPLE J-2

(S)-2-iodomethyl-1,2,3,4-tetrahydronaphthalene is substituted into the method of Example J-1 to yield (S)-4(5)-(1,2,3,4-tetrahydronaphthalen-2-ylmethyl)-1H-imidazole. (S)-2-iodomethyl-1,2,3,4-tetrahydronaphthalene was prepared from (S)-1,2,3,4-tetrahydro-2-naphthoic acid. (S)-1,2,3,4-tetrahydro-2-naphthoic acid was prepared from the resolution of 1,2,3,4-tetrahydro-2-naphthoic acid (*J. Med. Chem.* 1983, 26, 328–334)

EXAMPLE J-3

(R)-2-iodomethyl-1,2,3,4-tetrahydronaphthalene is substituted into the method of Example J-1 to yield (R)-4(5)-(1,2,3,4-tetrahydronaphthalen-2-ylmethyl)-1H-imidazole. (R)-2-iodomethyl-1,2,3,4-tetrahydronaphthalene was prepared from (R)-1,2,3,4-tetrahydro-2-naphthoic acid. (R)-1,2,3,4-tetrahydro-2-naphthoic acid was prepared from the resolution of 1,2,3,4-tetrahydro-2-naphthoic acid (*J. Med. Chem.* 1983, 26, 328–334)

EXAMPLE K-1
Procedure for Preparation of 4(5)-(4,5,6,7-tetrahydrobenzo[b]thiophen-2-ylmethyl)-1H-imidazole:

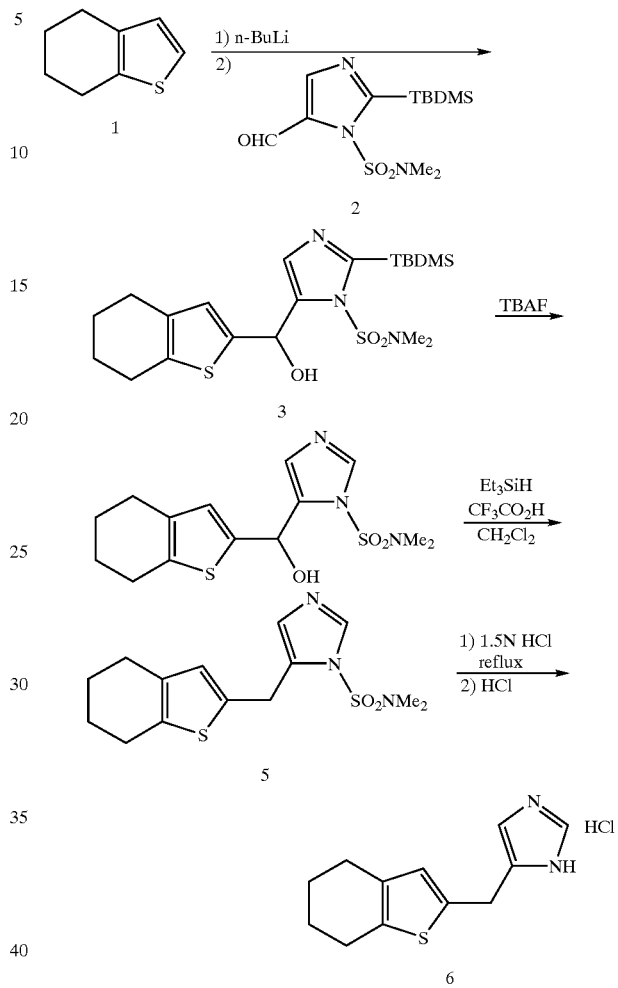

Procedure- 4,5,6,7-tetrahydrobenzo[b]thiophene (1) (2.1 g, 15 mmol) is taken up in 75 mL of anhydrous THF and cooled to −78° C. n-BuLi (6.0 mL, 15 mmol) is added dropwise to the solution of (1). The resultant solution is stirred at −78° C. for 60 min. 1-Dimethylsulfamoyl-2-t-butyldimethylsilyl-5-imidazolecarboxaldehyde (2) (4.8 g, 15 mmol) in 25 mL of THF is added to the reaction. The reaction is warmed to rt and stirred for 2 h before being quenched with water and diluted with ethyl acetate. The organic layer is washed with water followed by brine. The organic phase is dried over sodium sulfate and the solvent removed under reduced pressure. Flash chromatography (1:3 ethyl acetate/hexane) affords 5.2 g (11 mmol) of 2-(tert-butyldimethylsilyl)-5-[hydroxy-(4,5,6,7-tetrahydrobenzo[b]thiophen-2-yl)methyl] imidazole-1-sulfonic acid dimethylamide (3). (3) (5.2 g, 11.3 mmol) is taken up in 57 mL of THF. A 1M solution of tetra-n-butylammonium fluoride (TBAF) in THF (11.3 mL, 11.3 mmol) is added dropwise to the solution of (3). The reaction is stirred for 1 h 15 min reaction before being quenched with water and then extracted with ethyl acetate. The organic layer is washed with water followed by brine. The organic phase is dried over sodium sulfate and the solvent removed under reduced pressure. Recrystallization from hexane/ethyl acetate affords 5-[hydroxy-(4,5,6,7- tetrahydrobenzo[b]thiophen-2-yl)methyl]imidazole-1-sulfonic acid dimethylamide (4) (2.1 g, 6.2 mmol). An additional 2 g of the crude product is also recovered. (4) (2.0 g, 5.9 mmol) is taken up in 78 mL of dichloromethane, to the solution is added 7.5 mL (46.9 mmol) of triethylsilane and 14.4 mL (0.19 mol) of trifluoroacetic acid. The reaction is stirred at rt overnight and then quenched with water and neutralized with 2N NaOH. The organic layer is washed with water followed by brine. The organic phase is dried over sodium sulfate and the solvent removed under reduced pressure. Flash chromatography using a 1:1 mixture of ethyl acetate and hexane affords 0.75 g (2.3 mmol) of 5-(4,5,6,7-tetrahydrobenzo[b]thiophen-2-ylmethyl)imidazole-1-sulfonic acid dimethylamide (5). (5) (0.42 g, 1.55 mmol) is taken up in 15 mL of a 1.5N HCl solution and heated at reflux for 2 h and then stirred at rt overnight. The reaction is diluted with ethyl acetate, neutralized with 2N NaOH. The organic layer is washed with water followed by brine. The organic phase is dried over sodium sulfate and the solvent removed under reduced pressure. The crude product is dissolved in methanol and an excess of HCl in ether is added. Solvent is removed under reduced pressure to afford 0.6 g (2.3 mmol) of 4(5)-(4,5,6,7-tetrahydrobenzo[b]thiophen-2-ylmethyl)-1H-imidazole (6) (K-1).

$^1$H NMR (CD$_3$OD): 8.80 (s, 1H); 7.34 (s, 1H); 6.57 (s, 1H); 4.18 (s, 2H); 2.65 to 2.69 (m, 2H); 2.51 to 2.55 (m, 2H); 1.74 to 1.83 (m, 4H)

EXAMPLE K-2

2-(Tert-butyl) furan is substituted into the method of Example K-1 to yield 4(5)-(5-tert-butylfuran-2-ylmethyl)-1H-imidazole

EXAMPLE K-3

5,6-Dihydro-4H-thieno[2,3-b]thiopyran is substituted into the method of Example K-1 to yield 4(5)-(5,6-dihydro-4H-thieno[2,3-b]thiopyran-2-ylmethyl)-1H-imidazole

EXAMPLE L

Procedure for Preparation of 4(5)-(1-furan-2-ylethyl)-1H-imidazole:

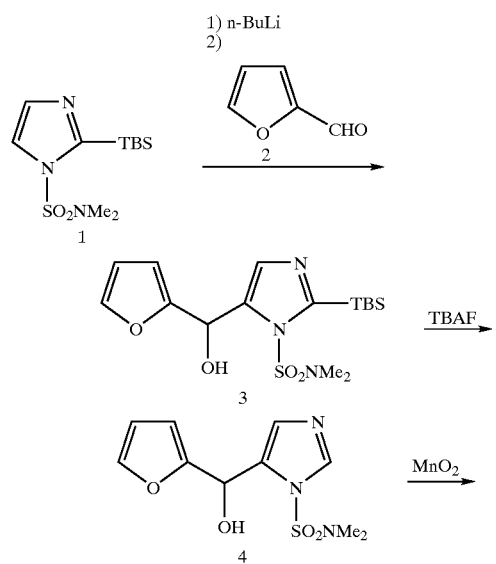

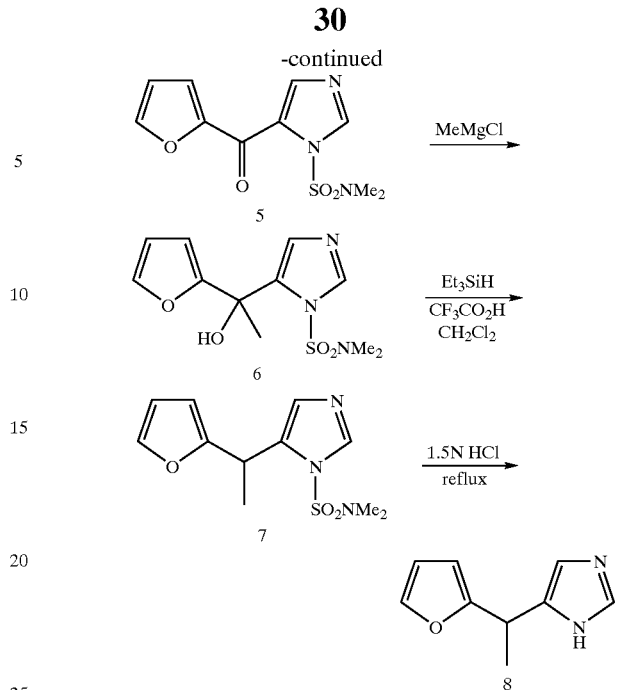

Procedure- 2-(Tert-butyldimethylsilyl)-1-(dimethylsulfamoyl)imidazole (1) (3.3 g, 11.4 mmol) is taken up in 38 mL of anhydrous THF and cooled to −78° C. n-BuLi (7.2 mL, 11.4 mmol) is added dropwise to the solution of (1). The resultant solution is stirred at −78° C. for 30 min. 2-Furfural (2) (0.94 mL, 11.4 mmol) is added to the reaction. The reaction is warmed to rt and stirred overnight. The next day the reaction is quenched with saturated ammonium chloride and diluted with ethyl acetate. The organic layer is washed with water followed by brine. The organic phase is dried over sodium sulfate and the solvent removed under reduced pressure. Flash chromatography (4:1 ethyl acetate/hexane) affords 4.4 g (11.4 mmol) of 2-(t-butyldimethylsilyl)-5-(furan-2-ylhydroxy-methyl)imidazole-1-sulfonic acid dimethylamide (3). (3) (4.4 g, 11.4 mmol) is taken up in 110 mL of THF and cool to 0° C. A 1M solution of tetra-n-butylammonium fluoride (TBAF) in THF (11.4 mL, 11.4 mmol) is added dropwise to the solution of (3). The reaction is stirred overnight at rt. The next day the reaction is quenched with water and then extracted with ethyl acetate. The organic layer is washed with water followed by brine. The organic phase is dried over sodium sulfate and the solvent removed under reduced pressure. 3.9 g of crude 5-(furan-2-ylhydroxymethyl)imidazole-1-sulfonic acid dimethylamide (4) is recovered. (4) (1.0 g, 3.7 mmol) is taken up in 37 mL of dichloromethane, to the solution is added 1.6 g (18.5 mmol) of manganese dioxide. The reaction is stirred at rt overnight and then filtered through celite. The eluent is collected and the solvent removed under reduced pressure. Flash chromatography using a 1:1 mixture of ethyl acetate and hexane affords 0.69 g (2.6 mmol) of 5-(furan-2-ylcarbonyl)imidazole-1-sulfonic acid dimethylamide (5). (5) (0.69 g, 2.6 mmol) is taken up in 26 mL of THF. The solution is cool to −78° C. 1.7 mL (5.1 mmol) of a 3M solution of methylmagnesium chloride is added. After stirring at −78° C. for 1.5 h reaction is warmed to rt and stirred for an additional hour. The reaction is quenched with water and then extracted with ethyl acetate. The organic layer is washed with water followed by brine. The organic phase is dried over sodium sulfate and the solvent removed under reduced pressure. Crystallization from ether/hexane affords 0.39 g (1.4 mmol) of 5-(1-furan-2-yl-1-hydroxyethyl)imidazole-1-sulfonic acid dimethylamide (6). An additional 0.19 g of (6) is recovered. (6) (0.58 g, 2.0 mmol) is taken up in 27 mL of dichloromethane, to the solution is added 2.6 mL (16.3 mmol) of triethylsilane and 5.5 mL (71.4 mmol) of trifluoroacetic acid. The reaction is stirred at rt overnight and then quenched with water and neutralized with solid sodium bicarbonate. The organic layer is washed with water followed by brine. The organic phase is dried over sodium sulfate and the solvent removed under reduced pressure.

Flash chromatography using a 2:1 mixture of ethyl acetate and hexane affords 0.53 g (2.0 mmol) of 5-(1-furan-2-ylethyl)imidazole-1-sulfonic acid dimethylamide (7). (7) (0.34 g, 1.3 mmol) is taken up in 10 mL of a 1.5N HCl solution and heated at reflux for 30 min and then stirred at rt overnight. The reaction is diluted with ethyl acetate and then made basic with 2N NaOH. The organic layer is washed with water followed by brine. The organic phase is dried over sodium sulfate and the solvent removed under reduced pressure. Flash chromatography (10:1 chloroform/methanol) affords 0.1 g (0.62 mmol) of 4(5)-(1-furan-2-ylethyl)-1H-imidazole (8) (L).

$^1$H NMR (300 MHz, CDCl$_3$) 7.56 (m, 1H), 7.33–7.34 (m, 1H), 6.81 (m, 1H), 6.29–6.31 (m,1H), 6.06–6.07 (m,1H), 4.22 (q, J=7.2 Hz, 1H), 1.63 (d, J=7.2 Hz, 3H).

EXAMPLE M

Procedure for Preparation of 4(5)-(2,3-dihydrobenzo[1,4]dioxin-6-ylmethyl)-4-methyl-1H-imidazole:

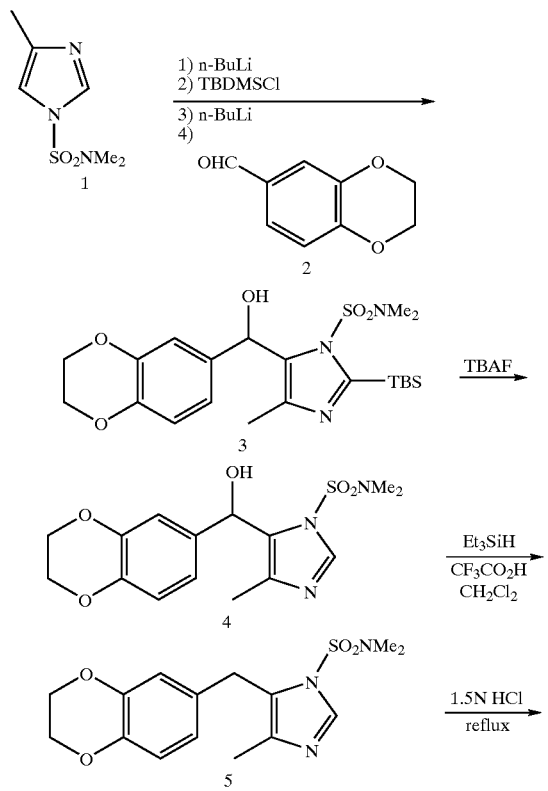

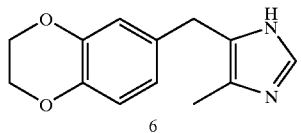

Procedure-

4-Methyl-1-(dimethylsulfamoyl)imidazole (1) (2.0 g, 10.6 mmol) is taken up in 42 mL of anhydrous THF and cooled to −78° C. n-BuLi (6.6 mL, 10.6 mmol) is added dropwise to the solution of (1). The resultant solution is stirred at −78° C. for 30 min. Tert-butyldimethylsilylchloride (TBSCl) (1.6 g, 10.6 mmol) in 10 mL of THF is added to the reaction. The reaction is warmed to rt and stirred overnight. The next day the reaction is cooled to −20° C. and 7.3 mL (11.6 mmol) of n-BuLi added. After stirring at −20° C. for 30 min, 1,4-benzodioxan-6-carboxaldehyde (2) (1.92 g, 11.7 mmol) in 10 mL of THF is added to the reaction mixture. Then reaction is warmed to rt and stirred for 3 h. The reaction is quenched with water and diluted with ethyl acetate. The organic layer is washed with water followed by brine. The organic phase is dried over sodium sulfate and the solvent removed under reduced pressure. Flash chromatography (1:2 ethyl acetate/hexane) affords 3.9 g (8.4 mmol) of 2-(t-butyldimethylsilyl)-5-[(2,3-dihydro benzo[1,4]dioxin-6-yl)hydroxymethyl]-4-methylimidazole-1-sulfonic acid dimethylamide (3). (3) (1.0 g, 2.14 mmol) is taken up in 21 mL of THF. A 1M solution of tetra-n-butylammonium fluoride (TBAF) in THF (2.35 mL, 2.35 mmol) is added dropwise to the solution of (3). The reaction is stirred for 30 min at rt. The reaction is quenched with water and then extracted with ethyl acetate. The organic layer is washed with water followed by brine. The organic phase is dried over sodium sulfate and the solvent removed under reduced pressure. Flash chromatography using ethyl acetate as eluant affords 0.75 g (2.12 mmol) 5-[(2,3-dihydrobenzo[1,4]dioxin-6-yl)hydroxymethyl]-4-methylimidazole-1-sulfonic acid dimethylamide (4). (4) (0.75 g, 2.12 mmol) is taken up in 28 mL of dichloromethane, to the solution is added 2.7 mL (17.0 mmol) of triethylsilane and 5.2 mL (67.8 mmol) of trifluoroacetic acid. The reaction is stirred at rt overnight and then quenched with water and neutralized with solid sodium bicarbonate. The organic layer is washed with water followed by brine. The organic phase is dried over sodium sulfate and the solvent removed under reduced pressure. Flash chromatography using a 3:1 mixture of ethyl acetate and hexane affords 0.63 g (1.87 mmol) of 5-(2,3-dihydrobenzo[1,4]dioxin-6-ylmethyl)-4-methylimidazole-1-sulfonic acid dimethylamide (5). (5) (0.63 g, 1.87 mmol) is taken up in 10 mL of a 1.5N HCl solution and heated at reflux for. The reaction is diluted with ethyl acetate, neutralized with solid sodium bicarbonate. The organic layer is washed with water followed by brine. The organic phase is dried over sodium sulfate and the solvent removed under reduced pressure. Crystallization from ether/hexane affords 0.33 g (1.43 mmol) of 4(5)-(2,3-dihydrobenzo[1,4]dioxin-6-ylmethyl)-4-methyl-1H-imidazole (6) (M).

$^1$HNMR (300 MHz, acetone-d$^6$) 7.37 (s, 1H), 6.66–6.67 (m, 3H), 4.18 (s, 4H), 3.73 (s, 1H), 2.13 (s, 3H)

EXAMPLE N

Procedure for Preparation of 2-(3H-imidazol-4(5)-ylmethyl)-3,4,5,6,7,8-hexahydro-2H-naphthalen-1-one (N-1), 4(5)-(2,3,4,4a,5,6,7,8-octahydronaphthlen-2-ylmethyl)-1H-imidazole (N-2) and 4(5)-(1,2,3,4,5,6,7,8-octahydronaphthalen-2-ylmethyl)-1H-imidazole (N-3):

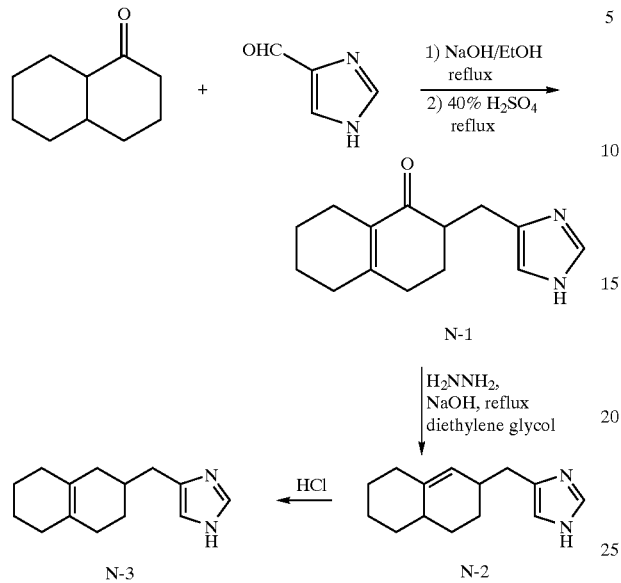

Procedure:

1-Decalone (10.0 g, 66 mmol) and 4(5)-imidazole carboxaldehyde (6.3 g, 66 mmol) were added to 100 mL of ethanol. To the solution was added NaOH (5.2 g, 130 mmol) in 20 mL of water. The reaction was heated at reflux for 5 days. The reaction was cooled to rt and made basic with aqueous HCl. The solution was extracted with THF/ethyl acetate. The organic layers were combined and washed with brine. The organic phase was dried over magnesium sulfate and the solvent removed under reduced pressure to afford the crude product. The crude product was heated at reflux in 40% $H_2SO_4$ for 1 day. The reaction was cooled to rt and made basic with saturated $K_2CO_3$. The solution was extracted with THF/ethyl acetate. The organic layers were combined and washed with brine. The organic phase was dried over magnesium sulfate and the solvent removed under reduced pressure. Purification by flash chromatography (15:1 $CH_3Cl$/MeOH) afforded N-1 (4.9 g, 32% yield).

$^1$H NMR: 7.55 (s, 1H), 6.77 (s, 1H), 3.08–3.14 (m, 2H), 1.52–2.46 (m, 13H).

The free base of the hydrochloride salt of N-1 (3.0 g, 11 mmol) was generated with NaOH and then added to diethylene glycol (100 mL). To the solution was added hydrazine hydrate (3.2 mL, 100 mmol) and the reaction was left to stir overnight at rt. NaOH (3.1 g, 77 mmol) was added and the solution heated at reflux for 5 days. The reaction was cooled to rt and diluted with water. The solution was extracted with THF/ethyl acetate. The organic layers were combined and washed with brine. The organic phase was dried over magnesium sulfate and the solvent removed under reduced pressure. Purification by flash chromatography (8:1 $CH_3Cl$/MeOH) afforded N-2 (0.64 g, 27% yield).

$^1$H NMR: 7.58 (s, 1H), 6.76 (s, 1H), 5.24 (d, J=4.3 Hz, 1H), 0.91–2.58 (m, 16H).

N-2 (1.0 g, 4.6 mmol) was added to 10 mL of concentrated HCl. The solution was stirred at rt for 30 min and then neutralized with $K_2CO_3$. The solution was extracted with THF/ethyl acetate. The organic layers were combined and washed with brine. The organic phase was dried over magnesium sulfate and the solvent removed under reduced pressure. Purification by flash chromatography (15:1 $CH_3Cl$/MeOH) afforded N-3.

$^1$H NMR: 7.54 (s, 1H), 6.74 (s, 1H), 2.45–2.52 (m, 3H), 1.46–1.97 (m, 14H).

EXAMPLE O

Procedure for Preparation of 4(5)-octahydro pentalen-2-ylmethyl)-1H-imidazole, hydrochloride:

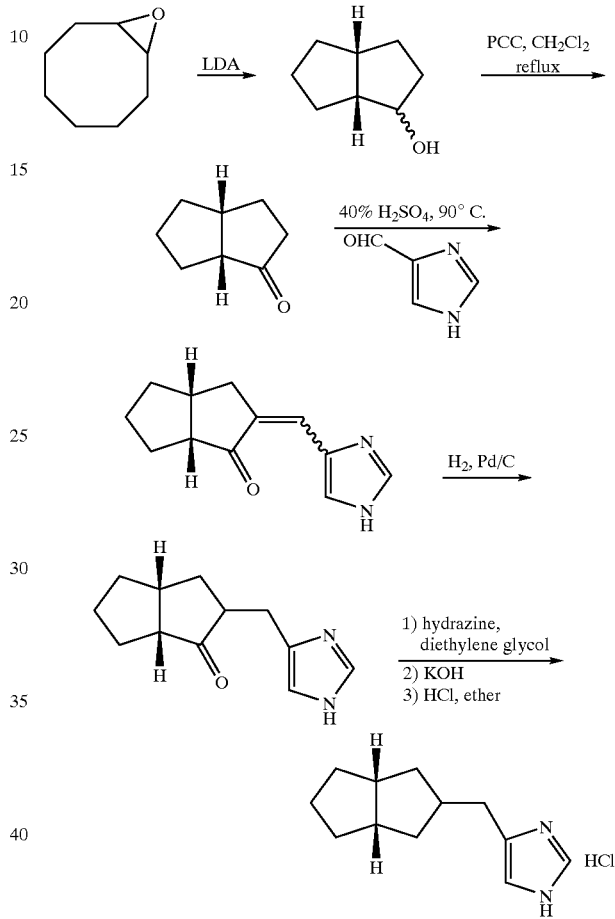

Procedure-

A. Following the synthesis of White and Whitesell, *Synthesis* pp. 602–3 (1975), ether (10 mL) was added to a flame-dried flask cooled to 0° C. and then kept under an argon atmosphere. Then n-butyl lithium (35 mL of 2.5 M solution in hexane, 2.2 equiv.) was added and subsequently diisopropyl amine (14 mL, 2.5 equiv.) was added slowly and the mixture was allowed to stir for 30 min. at 0° C. To this generated solution of lithium diisopropyl amide was added cyclooctene oxide (5.0 g, 1.0 equiv.). The mixture was stirred at rt for one day and then heated to reflux under argon atmosphere for 2 days. The reaction was quenched by addition of $NH_4Cl$. The solution was extracted with THF/EtOAc. The organic extracts were combined, washed with brine, dried over magnesium sulfate and concentrated in vacuo to afford a yellow brown oil which was the 1-hydroxy-octahydropentalene. The compound was used without further purification in the next step.

B. The alcohol thus obtained (5.0 g, 1 equiv.) was dissolved in dichloromethane (200 mL) and to this solution was added pyridinium chlorochromate (13 g, 1.5 equiv.) and the mixture was stirred at rt for one day. The solution was then filtered through a short column of $SiO_2$ using diethyl ether as eluent. The obtained solution was concentrated in vacuo to afford a pale green-yellow oil which was used without further purification in the next step.

C. The octahydro-pentalen-1-one (5.0 g, 1.0 equiv.) of the above step was added to 4(5)-imidazolecarboxaldehyde (3.8 g, 1.0 equiv.) and 40% $H_2SO_4$ (20 ml) and the mixture was maintained at 90° C. for 3 days. The reaction was then quenched by addition of ammonium hydroxide and extracted with tetrahydrofuran/ethyl acetate. The organic extracts were combined, washed with brine, dried over magnesium sulfate. The resulting aqueous layer was neutralized with $HCl/NH_4Cl$. The aqueous layer was re-extracted as above and the combined organic fractions were concentrated in vacuo to afford an orange solid.

D. This orange solid was dissolved in ethanol to which palladium on carbon (0.5 g) was added. The reaction flask was placed under 40 psi of hydrogen for one day. The reaction solution was filtered though celite with more ethanol used as eluent. The solution was concentrated in vacuo to afford a yellow brown oil. Purification by column chromatography using 17:1 chloroform/methanol afforded the ketone product in a somewhat impure state.

E. The ketone functionality was then removed by addition of the product of the step above (8.2 g, 1.0 equiv.) to diethylene glycol (80 mL) and hydrazine hydrate (13.0 g, 1.0 equiv.). This mixture was stirred overnight and then potassium hydroxide (11.0 g, 5.0 equiv.) was added and the solution was heated under reflux for one day. The reaction solution was cooled to rt and washed with water. The solution was extracted with THF/EtOAc and the combined fractions were washed with brine, dried over magnesium sulfate and concentrated in vacuo to afford a yellow oil. The monohydrochloride salt was made by dissolving this oil in anhydrous ethanol saturated with HCl and heating.

EXAMPLE P

Procedure for the Preparation of 7-(3H-imidazol4(5)-ylmethyl)-6,7-dihydro-5H-isoquinolin-8-one (P-1) and 7-(3H-imidazol-4(5)-ylmethyl)-5,6,7,8-tetrahydroisoquinoline (P-2):

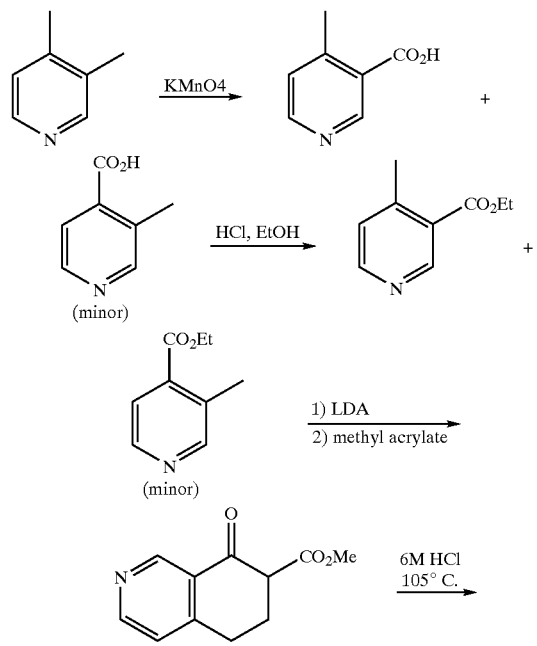

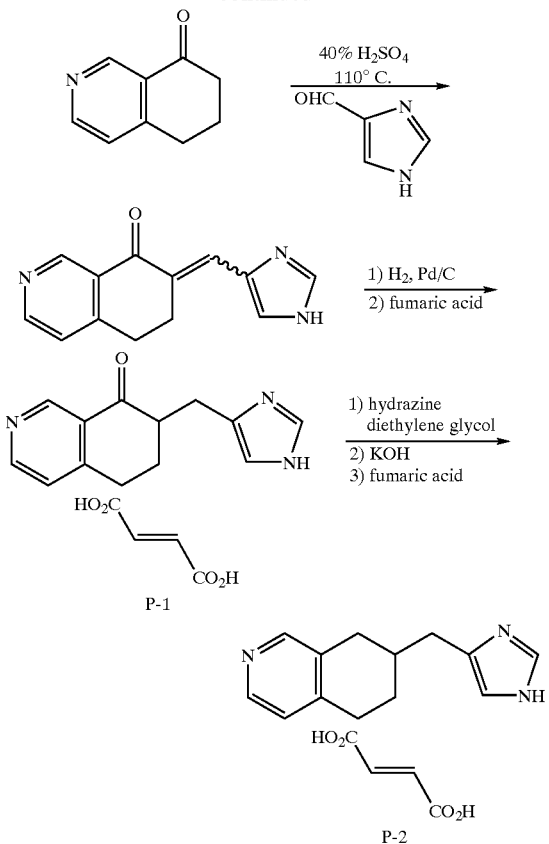

Procedure:

A. 3,4-lutidine (21.4 g, 1 equiv.) was dissolved in 200 mL of water at 20° C. and potassium permanganate was added in 6.32 g portions twice daily for 5 days (total 63.2 g, 2 equiv.). After 5 days the solution was stored in the freezer, then thawed and filtered through celite. The resulting colorless solution was concentrated at 90° C. on a rotary evaporator until a white solid was obtained. This solid was recrystallized from 5N HCl to give 9.56 g of white crystals. NMR indicated a mixture of two regioisomers with the desired isomer being the major product.

B. These crystals were heated in anhydrous ethanol saturated with HCl gas under argon and at reflux for 6 h. Then ethanol was removed from the solution by rotary evaporation and the residue was taken up in 100 mL of water and the pH was adjusted to between 7 and 8 with solid sodium bicarbonate. The aqueous phase was extracted with diethyl ether (3×) and the combined organic fractions were washed with brine, dried over magnesium sulfate and then filtered and concentrated to give a colorless oil (3.56 g, 10.8% yield).

C. Diisopropylamine 2.84 g, 1.3 equiv.) was added to n-BuLi (11.21 mL, 1.3 equiv.) in 100 mL of anhydrous THF under argon at −78° C. via syringe to produce lithium diisopropylamide in situ. To this solution was added the product of B above (3.56 g, 1 equiv.) in 20 mL of tetrahydrofuran, via syringe and the mixture was stirred at −78° C. for 20 min. At this point methyl acrylate (4.85 mL 2.5 equiv.) in 20 mL of tetrahydrofuran was added dropwise through a cannula. The solution was stirred another 2 h before quenching by addition of 40 mL of 10% potassium acetate. The solution was allowed to warm to 20° C. and then was concentrated on a rotary evaporator. The aqueous residue was extracted three times with chloroform. The combined fractions were washed with brine and dried over magnesium sulfate, filtered and concentrated to a black solid, which was stored under high vacuum. Chromatography on silica gel with hexanes/ethyl acetate (7/3→6/4) afforded 2.41 g (58.2%) of the desired product which was used without further purification in the next step.

D. The material from Step C (0.48 g, 1 equiv.) was dissolved in 1 mL of 6M HCl and heated at 105° C. for 16 h after which time the solution was concentrated to a solid by rotary evaporation at 80° C. The residue was taken up in 2 mL of water and neutralized with solid sodium bicarbonate. The neutralized solution was extracted with chloroform (3×) and the combined fractions were washed with brine, dried over magnesium sulfate and concentrated to a colorless oil. (0.456 g 93.4%).

E. The isoquinolone (1.91 g, 1 equiv.) obtained in step D above was heated with 4(5)-imidazolecarboxaldehyde 1.25 g, 1. equiv.) at 110° C. in 15 mL of 40% sulfuric acid for 30 h. The reaction mixture was stored for several days at 0° C. under argon. The solution was then diluted with 20 mL of water and basified to pH 8.9 with NH$_4$OH. Solids were collected by filtration and dried with high vacuum. The product was a yellow solid (2.81 g, 96.1%) comprising a mixture of both positional isomers at the exo double bond.

F. The product of E, above, was dissolved in 150 mL of methanol and to this solution Pd/C (0.412 g, 0.15 wt. equiv.) was added. The methanolic solution was then saturated with H$_2$ by repeated evacuations and H$_2$ back-fill iterations. The solution was stirred under 1 atm. pressure of H$_2$ for 20 h until TLC revealed that no unsaturated starting material remained. The solution was filtered through celite and concentrated to an oil. Chromatography on silica using dichloromethane and methanol (9/1) recovered pure product (1.853 g 6504%) as a white foam. This was taken up in methanol to which fumaric acid (0.4817 g, 1.5 equiv.) was added with warming to dissolve the solids. The solution was cooled slowly and off-white crystals (0.826 g, 74%) were obtained, which are represented as the compound P-1. P-2 was obtained by hydrazine reduction in the same manner as described in Step E of Example O above.

EXAMPLE Q

Procedure for the Preparation of (Z)-6-(3H-imidazol-4(5)-ylmethylene)-7,8-dihydro-6H-quinolin-5-one (Q-1), (E)-6-(3H-imidazol-4(5)-ylmethylene)-7,8-dihydro-6H-quinolin-5-one (Q-2), 6-(3H-imidazol-4(5)-ylmethyl)-7,8-dihydro-6H-quinolin-5-one (Q-3), 6-(3H-imidazol-4(5)-ylmethyl)-5,6,7,8-tetrahydroquinoline, dihydrochloride (Q-4) and 6-(3H-imidazol-4(5)-ylmethyl)-octahydroquinolin-5-one (Q-5)

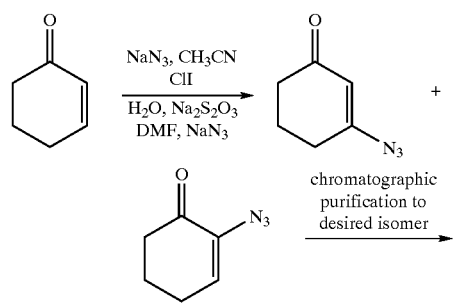

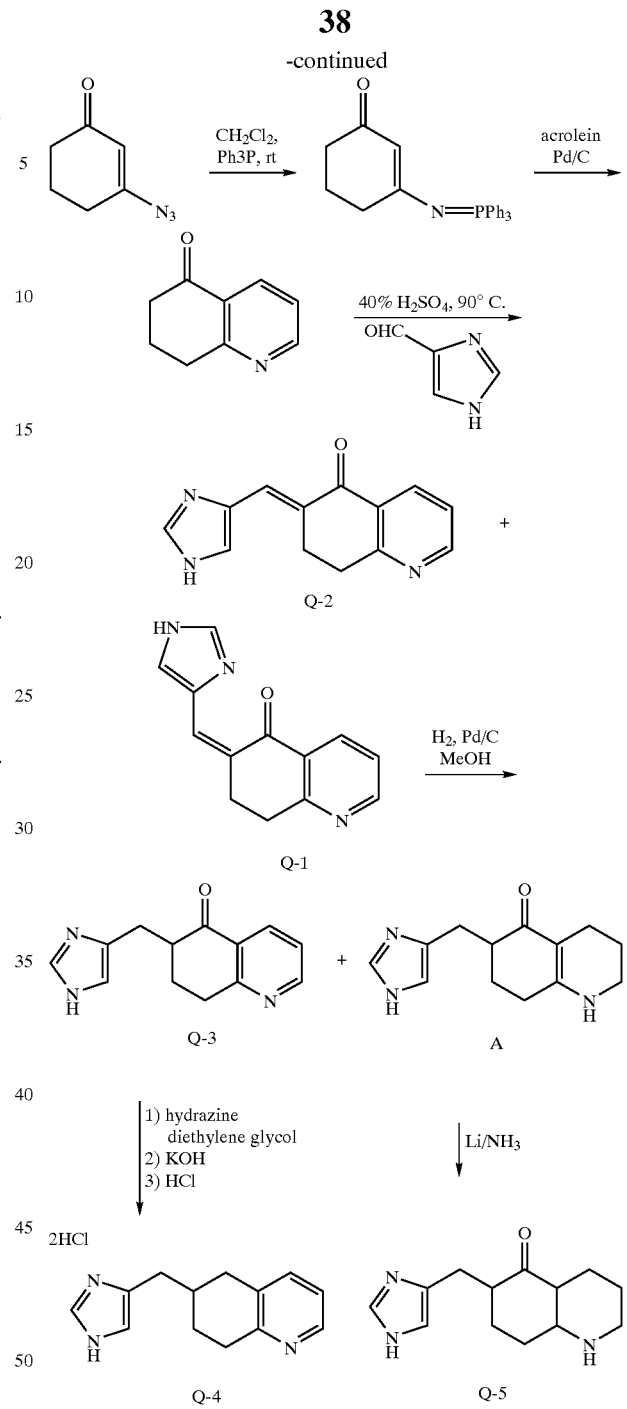

Procedure:

A. The reactive azido reagent of the first step was generated in situ by addition of iodine monochloride (67.6 g, 1.15 equiv.) in 50 mL of acetonitrile dropwise through a dropping funnel to a stirred slurry of sodium azide (58.84 g, 2.5 equiv.) in 350 mL of anhydrous acetonitrile at −10° C. and under argon. Addition was complete in 30 min, the mixture was stirred an additional 30 min and cyclohexenone (34.81 g, 1.0 equiv.) was added via a syringe and then stirred at 20° C. for an additional 20 h. The mixture was then poured into a liter of water and extracted with three 200 mL portions of diethyl ether. The combined fractions were washed with 5% sodium thiosulfate solution and then brine. The organic phase was dried over magnesium sulfate, filtered and concentrated in vacuo at 20° C. The residues were taken up in 1 L of DMSO at 0° C. and a second portion of NaN₃ was added and the mixture stirred while warming to ambient temperature. This mixture was then diluted with 2.5 L of ice water and extracted ten times with dichloro-methane (10× 250 mL). The combined organic fractions were concentrated on a rotovap to a volume of 1 L and this concentrate was extracted three times with 250 mL of water, and then brine, and then dried over magnesium sulfate and concentrated to a dark oil (39.5 g) and stored at −40° C.

The oil was purified by chromatography on silica using 9/1 to 8/2 hexane:ethyl acetate. Two isomers were recovered, the first with the azido group α to the ketone function was obtained in 13.22 g, 26.6%, yield. The β-isomer was obtained in 15.825 g, 32.0%, yield.

B. Triphenyl phosphine was dissolved in 20 mL of dichloromethane and placed under an argon atmosphere at 20° C. The β-isomer obtained as described above was added via cannual to the stirred solution and maintained at 20° C. for 2 h. As the reaction progressed nitrogen was liberated from the solution, and after 2 h TLC demonstrated there was no starting material remaining. The solution was concentrated and passed through a silica gel column with dichloromethane progressing to 95/5 dichloromethane:methanol as eluent. The amidophosphonate intermediate was obtained in 2.139 g, 65.1%, yield.

C. The amidophosphonate was dissolved in 100 mL of anhydrous o-xylene and then 10% Pd/C was added with stirring. Freshly distilled acrolein was then added to the mixture via syringe and heated to reflux for 4 h, after which time the remaining acrolein was added and heating under reflux was continued for 44 h under a finger condenser and under argon. At that time TLC indicated some intermediate remained, so 0.5 g addition Pd/C was added and the mixture again was heated to reflux for another 8 h. The mixture was cooled to rt, filtered and concentrated on a rotovap to eliminate excess acrolein, until about 100 mL of o-xylene solution remained. This solution was cooled by addition of ice, and was extracted three times with 1N HCl. The combined aqueous fractions were extracted 3× with Et₂O. The aqueous phase was then cooled to 0° C. and the pH was adjusted to ~10 using concentrated NaOH. The aqueous was then extracted 5× with 100 mL portions of chloroform. The combined chloroform fractions were washed with water and then brined and dried over magnesium sulfate, filtered, and finally concentrated to give 3.51 g of an oil in 84.4% yield of 7,8-dihydro-6H-quinolin-5-one.

D. The 4(5)-imidazole carboxaldehyde was condensed with the quinolinone as described in Step E of Example P and was obtained both Q-1 and Q-2.

E. The exo double bond was then reduced with palladium on carbon as described in Step F of Example P above to yield two products which were separated by chromatography to give Q-3 and A.

F. The keto group was removed by the same hydrazine reduction procedure as that described in Step E of Example O above to give Q4.

G. The fully-reduced quinoline ring product Q-5 was obtained by a standard reduction of A with lithium/ammonia. (Li, 10 equiv., in NH₃ at −78° C. for 10 min, quenched with NH₄OH, gradual warming with NH3 evaporation).

EXAMPLE R-1

Procedure for the preparation of (E)-6-(3H-imidazol-4(5)-ylmethylene)-7,8-dihydro-6H-quinoxalin-5-one:

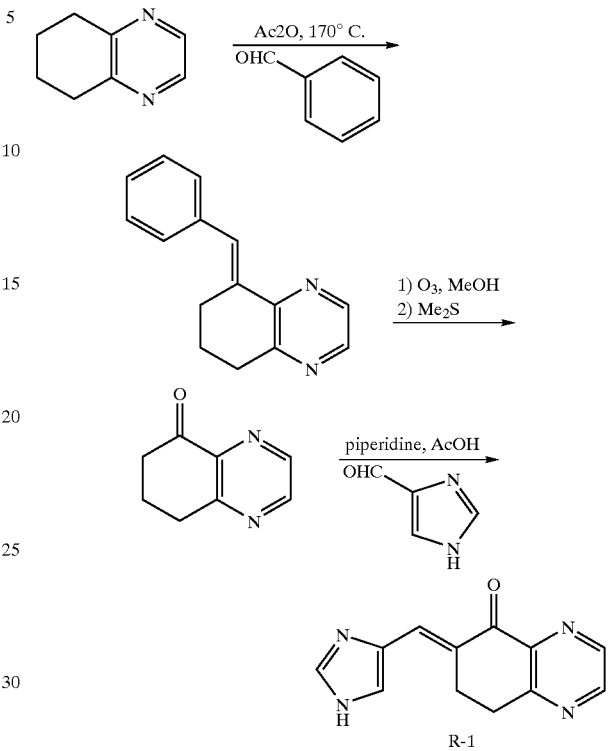

Procedure:

A. A mixture of 5,6,7,8-tetrahydroquinoxaline (23.75 g, 1 equiv.), benzaldehyde (19.81 mL, 1.1 equiv.) and acetic anhydride (33.4 mL, 2.0 equiv.) was stirred at 150° C. under argon for 15 hr, after which time TLC indicated mostly desired product with some starting materials remaining. Starting materials were removed by vacuum distillation using a Vigreux column at 170° C. The pot residue was then subjected to Kugelrohr distillation from 170–220° C. The first fraction was slightly contaminated with starting materials (4.71 g). A second fraction was pure (18.93 g). After applying high vacuum to the first fraction it crystallized. Combined fractions yielded 20.11 g, 51%.

B. The product from A, above, was dissolved in 100 mL of methanol and warmed slightly, then cooled to −35 to −40° C. and ozone was bubbled through the solution. After a few minutes the starting material began to crystallize out of solution and the solution was warmed and another 200 mL of methanol was added and then the reaction was resumed. After about 30 minutes the solution turned pale blue. Nitrogen was then introduced by bubbling through the solution for 30 minutes, then methyl sulfide (3.5 mL) was injected into the solution, whereafter the solution was stirred for another 30 min. at −35° C., then allowed to warm to ambient temperature with stirring. After about 48 hr. at 20° C. the mixture was steam distilled to remove solvents to provide a residue of 8.4 g of a yellow-brown oil. This residue was taken up in diethyl ether and extracted 3× with 25 mL portions of 1N HCl. The combined aqueous fractions were washed with diethyl ether 3×. The aqueous solution was gradually basified to a pH of 8 with concentrated NaOH. The free amine was then extracted from the aqueous phase with chloroform (3×). The combined chloroform extracts were washed twice with brine, dried of MgSO₄ and concentrated to a yellow oil (3.01 g) After keeping under high vacuum for 1 hr., 2.97 g remained. This was recrystallized from diethyl ether to give 2.35 g of a bright yellow solid. Yield 67.5%.

c. The 7,8-dihydroquinoxalin-5-one and 4(5)-imidazolecarboxaldehyde (Aldrich Chemicals) were suspended in 75 mL of anhydrous tetrahydrofuran at 20° C. under argon followed by addition of piperidine followed by acetic acid. The mixture was stirred 16 h at 20° C. After 20 h, no traces of the quinoxalone remained as indicated by TLC. The solids were collected by filtration and washed with a small amount of tetrahydrofuran, followed by chloroform. The solid was dried under high vacuum to give 6.85 g of R-1. Yield 90.3%.

EXAMPLE R-2 AND R-3

In a similar manner as R-1, 5,6,7,8-tetrahydroisoquinoline (5.42 g, 1 equiv., Aldrich) was stirred with benzaldehyde (5.182 g, 1.2 equiv.) and acetic anhydride (6.309 g, 2.0 g) which was vacuum distilled and used without further purification in the next step. Yield (impure): 8.28 g.

The crude product (7.96 g) from the step above was subjected to ozonolysis as described in Step B above. After work-up and chromatography there was obtained 5.18 g of a pale oil. Yield: 97.8% assuming pure starting material.

The resulting 7,8-dihydro-6H-isoquinolin-5-one (1.692 g, 1 equiv.) was condensed with 4(5)-imidazolecarboxaldehyde as described in Step C above to yield 2.23 g of the unsaturated compound analogous to R-1 in the scheme above in 92.8% yield. This product was treated with palladium on carbon as described in Step F of Example P to reduce the exo double bond to produce 6-(3H-imidazol-4(5)-ylmethyl)-7,8-dihydro-6H-isoquinolin-5-one (R-2) in 52%. The ketone above was reduced using hydrazine and converted to the fumarate salt as detailed in Example P, Step F. Yield for the reduction: 62%. Yield of fumarate salt after recrystallization: 30.4% of 6-(3H-imidazol-4(5)-ylmethyl)-5,6,7,8-tetrahydroisoquinoline (R-3).

EXAMPLE S

Procedure for the Preparation 4(5)-(4a-methyl-2,3,4,4a,5,6,7,8-octahydro-naphthalen-2-ylmethyl)-1H-imidazole, but-2-enedioic acid salt:

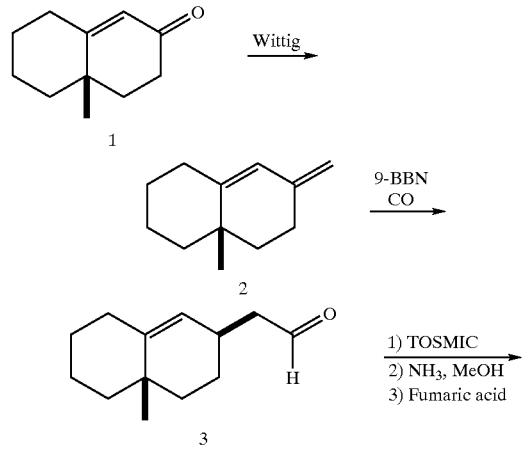

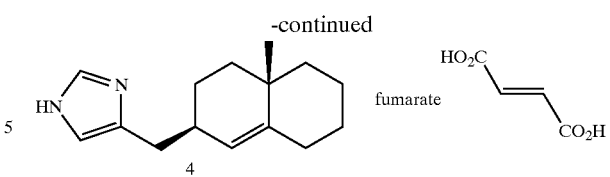

Procedure-

Methyl triphenylphosphonium bromide (2.75 g, 7.70 mmol) was suspended in 50 mL of diethyl ether. At −10° C., nBuLi (3.08 mL, 7.70 mmol, 2.5M soln in hexanes) was added. This mixture was stirred for 35 m before cooling to −70° C. A solution of (R)-(+)-4,4a,5,6,7,8-hexahydro-4a-methyl-2(3H)-naphthalenone (1) (1.0 g, 6.09 mmol) in 15 mL of ether was added via syringe. This mixture was warmed to 0° C. over 30 m and the stirred at rt for another 30 m. The solution was washed with brine (2×20 mL) dried over $MgSO_4$, filtered and the solvent was removed. Chromatography on $SiO_2$ with hexanes gave 0.82 g (83%) of the diene 2 as a clear colorless oil.

This hydroboration procedure follows that by Brown, H. C. et. al. *J. Am. Chem. Soc.* 1969, 91, 2144. To a solution of the diene 2 (750 mg, 4.63 mmol) in 20 mL of THF was added 9-BBN (11.8 mL, 5.9 mmol, of a 0.5 M soln. in THF) at 0° C. This was warmed to rt after 30 m and allowed to react at rt for 1 h. Dry MeOH (3.75 mL, 15.0 mmol as a 4.0 M soln in THF) was added to a stirred solution of $LiAlH_4$ (5.04 mL, 5.04 mmol, 1.0 M in ether) to form $LiAlH(OMe)_3$. The borane was added to this alkoxy aluminum hydride via syringe. After 10 m at rt, carbon monoxide was bubbled through the solution for 20 m. Phosphate buffer (25 mL, pH 7.0 was added followed by $H_2O_2$ (10 mL, 30% soln) and this was stirred for 30 m. After a typical extraction process the oil was purified by chromatography on $SiO_2$ with 5 to 10% EtOAc:Hx to yield the colorless aldehyde 3 as the major product 455 mg, (51%).

This preparation followed the protocol by Home, D. A.; Yakushijin, K.; Buichi, G. *Heterocycles,* 1994, 39, 139. A solution of the above aldehyde 3 (450 mg, 2.34 mmol) in EtOH (8 mL) was treated with tosylmethyl isocyanide (TosMIC) (430 mg, 220 mmol) and NaCN (~15 mg, cat) at rt for 20 m. The solvent was removed in vacuo and the residue dissolved in MeOH saturated with $NH_3$ (10 mL). The solution was heated in a resealable tube at 110° C. for 6–12 h. The material was concentrated and purified by chromatography on $SiO_2$ with 5% MeOH (sat. w/$NH_3$) :$CH_2Cl_2$ to give the imidazole as a thick glass 193 mg (36%).

The imidazole was purified further by stirring in THF or MeOH with an equimolar amount of fumaric acid at rt for 10 m. The solvent was removed and the salt recrystallized by dilution in THF and tituration with ether:hexanes for a 70–80% recovery of pure fumarate 4 (S).

$^1$H NMR (500 MHz, DMSO-$d_6$ w/TMS): δ 7.73 (s, 1 H), 6.83 (s, 1 H), 6.60 (s, 2 H), 5.12 (s, 1 H), 2.45–2.44 (m, 2 H), 2.30 (brs, 1 H), 2.12 (brs, 1 H), 1.91–1.88 (m, 1 H), 1.73–1.71 (m, 1 H), 1.56–1.46 (m, 5 H), 1.30–1.09 (series of m, 4 H), 1.01 (s, 3 H) $^{13}$C (125 MHz, DMSO-$d_6$ w/TMS): δ 167.0, 143.5, 134.8, 134.5, 128.7, 123.7, 118.2, 42.3, 36.7, 35.0, 32.8, 32.5 (2C), 28.4, 25.9, 24.4, 22.3.

EXAMPLE T-1
Procedure for the Preparation 4(5)-(3-methyl-cyclohex-2-enylmethyl)-1H-imidazole, but-2-enedioic acid salt:

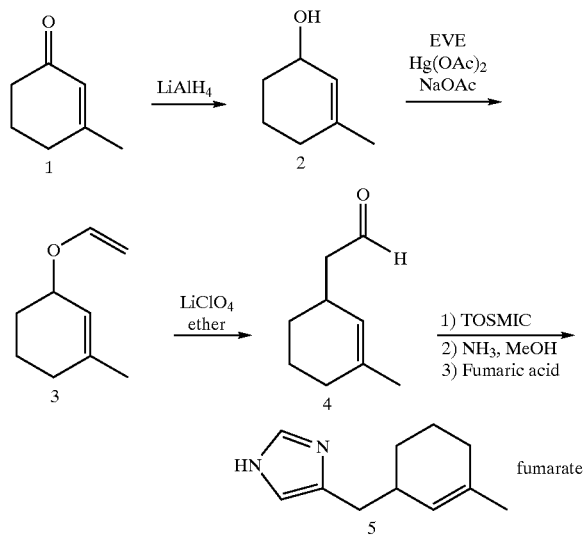

EXAMPLE U-1
Procedure for the Preparation 4(5)-cyclohex-2-enylmethyl-1H-imidazole, but-2-enedioic acid salt:

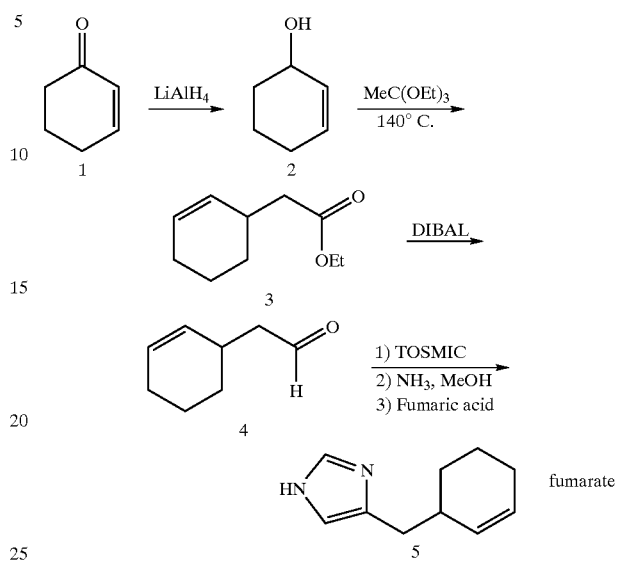

Procedure-

A solution of 3-methyl-2-cyclohexen-1-one (1) (5 g, 45.4 mmol) in 25 mL of ether was added dropwise via an addition funnel to a solution of LiAlH$_4$ (45 mL, 1M in THF) in ether (100 mL) at −10° C. After 1 h the mixture was carefully quenched with NH$_4$Cl (10 mL) and treated with 10% HCl (7 mL). The organic layer was extracted with ether (3×70 mL), dried over MgSO$_4$, filtered and concentrated. The residue was purified by chromatography by elution with 20% EtOAc:Hx to give 2, a clear colorless alcohol, 4.46 g (88%).

A solution of alcohol 2 (1.68 g, 15 mmol) in ethyl vinyl ether (38 mL) was treated with Hg(OAc)$_2$ (3.2 g, 10 mmol) and NaOAc (410 mg, 5 mmol) at 35° C. for 4 h. The mixture was poured onto 5% KOH solution (15 mL), diluted with ether and extracted with hexanes. The organic layer was dried over Na$_2$SO$_4$, filtered and concentrated. The crude residue was used in the next step without further purification.

According to the procedure by Greico, P. A.; et al, *J. Am Chem. Soc.* 1991, 113, 5488, a 3M solution of LiClO$_4$ (16 g, 150 mmol) in 50 mL of ether was treated with the crude vinyl ether 3 at rt for 30 m. The entire mixture was poured onto sodium bicarbonate solution (150 mL). After extraction of the aldehyde 4 with ether, the organic layer was dried over MgSO$_4$, filtered, and concentrated under reduced pressure. The crude residue was purified by chromatography on SiO$_2$ with EtOAc:Hx or submitted to the Büchi protocol as described above for the formation of the imidazole-fumarate 5 (8% from 6 to free base of 5).

$^1$H NMR (500 MHz, d$^6$-DMSO w/TMS): δ 7.71 (s, 1 H), 6.82 (s, 1 H), 6.61 (s, 2 H), 5.27 (s, 1 H), 2.46–2.32 (series of m, 3 H), 1.85 (brs, 2 H), 1.60 (s, 3 H), 1.35–0.86 (series of m, 4 H) $^{13}$C (125 MHz, DMSO-d$_6$ w/TMS): δ 167.3, 134.9,134.5, 125.5, 118.1, 35.5, 32.6, 30.1, 28.5, 24.0, 21.4.

EXAMPLE T-2
4(5)-(3,5,5-trimethyl-cyclohex-2-enylmethyl)-1H-imidazole, but-2-enedioic acid salt is prepared by substituting isophorone in the method of T-1

EXAMPLE T-3
4(5)-(3-methyl cyclopent-2-enylmethyl)-1H-imidazole, but-2-enedioic acid salt is prepared by substituting 3-methyl-2-cylopenten-1-one in the method of T-1

Procedure-

A solution of cyclohexenone (1) (2.88 g, 30 mmol) in hexanes at −78° C. was treated with DIBAL (30 mL, 1.0 M in cyclohexane). After 25 m, MeOH (7 mL) was added and the mixture was warmed to rt. A saturated solution of Rochelle's salt was added followed by dilution with ether (100 mL). The organic layer was separated, dried over MgSO$_4$, filtered and concentrated under vacuum. The product was purified by chromatography on SiO$_2$ with 20% EtOAc:Hx to give a clear colorless alcohol 2, 2.0 g (68%).

A solution of the above alcohol 23 (2.0 g, 20.4 mmol) in triethyl orthoacetate (30 mL) and propionic acid (~0.025 mL, cat) was heated to remove ethanol. After the ethanol was removed heating was continued at 145° C. for 1 h. The triethyl orthoacetate was removed by simple distillation. After the residue cooled to rt the product was purified by chromatography on SiO$_2$ with 5% ether:Hx to give ester 3 as a clear colorless oil 1.08 g (~31%).

A solution of the above ethyl ester 3 (1.0 g, 5.9 mmol) was dissolved in hexanes (50 mL) and cooled to −78° C. A solution of DIBAL (5.8 mL 1.0 M in cyclohexane) was added dropwise. After 15 m, diethyl ether (50 mL) was added and the mixture was stirred with Rochelle's salt solution (25 mL) for 10 m. The organic layer was separated, dried and filtered. Chromatography on SiO$_2$ with 7% Et$_2$O:Hx delivered the aldehyde as a clear colorless oil, 0.52 g (74%). The aldehyde 4 was subjected to the Büchi protocol as described above. The fumarate salt of the imidazole 5 (U-1) was obtained in three steps (25% overall).

$^1$H NMR (500 MHz, DMSO-d$_6$ w/TMS): δ 7.67 (s, 1 H), 6.80 (s, 1 H), 6.60 (s, 2 H), 5.66–5.54 (m, 2 H), 2.52–2.42 (m, 2 H), 2.34 (brs, 1 H), 1.93 (s, 2 H), 1.66 (brs, 2 H), 1.46–1.43 (m, 1 H), 1.22–1.16 (m, 1 H) $^{13}$C (125 MHz, DMSO-d$_6$ w/TMS): δ 166.3, 134.3, 134.2, 131.2, 126.9, 118.1, 96.5, 35.0, 32.5, 28.4, 24.8, 20.7.

EXAMPLE U-2
4(5)-(4-methyl-cyclohex-2-enylmethyl)-1H-imidazole, but-2-enedioic acid salt is prepared by substituting 6-methyl-2-cyclohexen-1-one in the method of U-1

EXAMPLE V
Procedure for the Preparation of 2-(1H-imidazole-4(5)-ylmethyl)-cyclohexanone, but-2-enedioic acid salt:

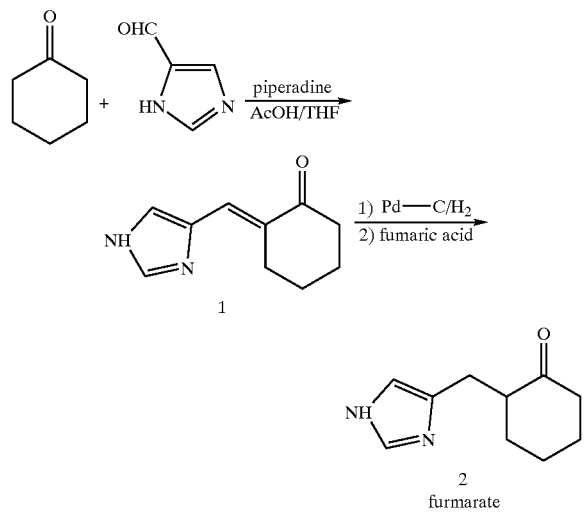

Procedure-

To the 4(5)-imidazolecarboxaldehyde (2.52 g, 26.23 mmol) suspended in cyclohexanone (25.74 g, 262.25 mmol) under argon added the piperadine (0.56 g, 6.56 mmol) and acetic acid (0.52 g, 8.65 mmol). After heating at reflux for 16 h. the cyclohexanone was removed by kugelrohr. Chromatography on $SiO_2$ with 5–10% MeOH (saturated with $NH_3$): $CH_2Cl_2$ gave 4.07 g (88%) of unsaturated imidazole 1 as an oil.

The unsaturated imidazole 1 (1.02 g, 5.81 mmol) in MeOH (40 ml) containing palladium (10 wt. % on activated carbon) (0.15 g) was hydrogenated at 1 atmosphere pressure of $H_2$. After 16 h the palladium was filtered off and the filtrate was concentrated at reduced pressure. The imidazole was recrystallized by stirring in MeOH with an equimolar amount of fumaric acid until all solids had disappeared followed by the addition of a small amount of diethyl ether and cold storage. The title compound 2 (V) 0.80 g (48%) was recovered as white crystals.

$^1$H NMR (300 MHz, $CDCl_3$ w/TMS): δ 9.5–6.5 (vbs, 3H), 7.71(s, 1H), 6.80 (s, 1H), 6.60 (s, 2H), 2.91(dd, J=14.8 Hz, J=5.4 Hz, 1H), 2.75–2.60 (m, 1H), 2.42–2.28 (m, 2H), 2.27–2.17 (m, 1H), 2.02–1.89 (m, 2H), 1.78–1.68 (m, 1H), 1.68–1.45 (m, 2H), 1.32–1.17 (m, 1H) $^{13}$C NMR (75 MHz, DMSO-$d_6$ w/TMS): δ 211.6, 166.6, 134.4, 134.2, 133.8, 117.4, 49.7, 41.4, 33.1, 27.5, 25.8, 24.3.

EXAMPLE W-1
Procedure for the Preparation of 4(5)-(3,4-Dimethyl-cyclohex-3-enylmethyl)-1H-imidazole, but-2-enedioic acid salt:

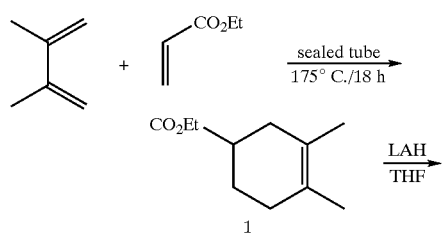

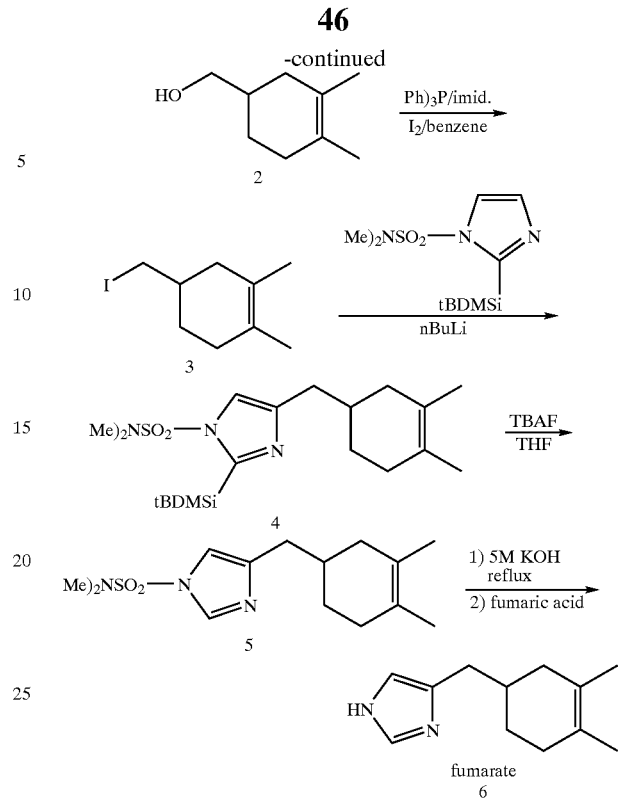

Procedure- 2,3-Dimethyl-1,3-butadiene (10.16 g, 123.72 mmol), ethyl acrylate (11.06 g, 110.47 mmol) and hydroquinone (0.12 g, 1.11 mmol) were heated with stirring at 165° C. in a sealed tube for 16 h and then at 205° C. for an additional 4 h. Kugelrohr distillation of the resulting residue at 150° C. and 0.5 torr gave 14.11 g (70%) of cyclohexene ester 1 as an oil in the 20° C. bulb. To a solution of the ester 1 (13.62 g, 72.32 mmol) in anhydrous THF (200 ml) at –78° C. under argon added the $LiAlH_4$ (54.30 ml, 1 M in diethyl ether). This mixture was stirred for 1 h at 20° C. and then quenched at 0° C. by the careful, consecutive addition of $H_2O$ (2.06 ml), NaOH (2.06 ml of a 15% aqueous solution), and an additional portion of $H_2O$ (6.18 ml). The solids were filtered off and the filtrate was concentrated under reduced pressure. Kugelrohr distillation of the resulting residue at 150–180° C. and 0.5 torr gave 9.98 g (98%) of the alcohol 2 as a colorless volatile oil in the 0° C. bulb. To a solution of triphenyl phosphine (27.13 g, 103.45 mmol), and imidazole (7.04 g, 103.45 mmol) in anhydrous benzene (450 ml) under argon was added the $I_2$ (22.75 g, 89.61 mmol) in benzene (170 ml) over a period of 10 minutes with rapid mechanical stirring. After an additional 10 minutes the alcohol 2 (9.23 g, 65.89 mmol) in benzene (100 ml) was added to this rapidly stirring mixture over a period of 5 minutes. After 2 h the reaction was diluted with hexanes (800 ml) and the solids were filtered off. The organics were washed with 3 portions of $H_2O$ (800 ml), dried ($MgSO_4$), filtered and concentrated under reduced pressure. The residual solids were filtered off and the resulting oil was purified by kugelrohr distillation at 200° C. and 0.5 torr to give 11.99 g (73%) of the iodide 3 as a pale oil in the 0° C. bulb. To a solution of the previously described 1-N-(dimethylsulfamoyl)-2-tert-butyldimethylsilyl imidazole (4.34 g, 15.00 mmol) in anhydrous THF (50 ml) at –78° C. under argon was added n-butyllithium (5.76 ml, 2.5 M in hexanes). This mixture was stirred for 10 minutes at –10° C. and then cooled to –20°

C. before adding the iodide 3 (3.00 g, 12.00 mmol) in THF (25 ml) dropwise via cannula. The resulting solution was stirred for 16 h at 20° C., then quenched with saturated aqueous NaHCO₃ and concentrated under reduced pressure. The residues were taken up in diethyl ether and washed consecutively with H₂ and brine, dried (MgSO4) and concentrated. Subsequent purification by chromatography on SiO₂ with 5–10% EtOAc:hexanes gave 0.89 g (15%) of the imidazole 4 as a pale oil. To a solution of imidazole 4 (0.89 g, 2.17 mmol) in anhydrous THF (25 ml) under argon was added tetrabutylammonium fluoride (2.38 ml, 1 M in THF) and the resultant solution was stirred for 1 h at 20° C. The mixture was concentrated under reduced pressure and the residues were taken up in diethyl ether and washed consecutively with saturated aqueous NaHCO₃ and brine, dried (MgSO₄) and concentrated. The residues were purified by chromatography on SiO₂ with 50% EtOAc:hexanes to give 0.56 g (87%) of the imidazole 5 as a pale oil. To a solution of 5 (0.53 g, 1.77 mmol) in MeOH (5 ml) was added aqueous KOH (15 ml of a 5M solution) and the mixture was heated at reflux for 32 h. The mixture was concentrated under reduced pressure, diluted with H₂O (5 ml) and extracted exhaustively with CHCl₃. The combined organic fractions were washed consecutively with H₂O and brine, dried (MgSO₄) and concentrated under reduced pressure. The imidazole was recrystallized by stirring in MeOH with an equimolar amount of fumaric acid until all solids had disappeared followed by the addition of a small amount of diethyl ether. The title compound 6 (W-1) 0.27 g (57%) was recovered as pale crystals.

$^{1}$H NMR (300 MHz, DMSO-$d_6$ w/TMS) δ 10.3–8.8 (vbs, 3 H), 7.88 (s, 1H), 6.89 (s, 1H), 6.59 (s, 2H), 2.48 (d, J=6.7 Hz, 2 H), 2.00–1.70 (m, 4 H), 1.70–1.57 (m, 2 H), 1.56 (s, 3 H), 1.54 (s, 3 H), 1.21–1.04 (m, 1 H)) $^{13}$C NMR (75 MHz, DMSO-$d_6$ w/TMS) : δ 166.7, 134.4, 134.1, 133.4, 124.8, 124.3, 117.9, 37.6, 34.1, 32.2, 31.1, 28.7, 19.0, 18.7.

EXAMPLE W-2

4(5)-Cyclohex-3-enylmethyl-1H-imidazole, but-2-enedioic acid salt is prepared by substituting 3-cyclohexene-1-methanol in the method of W-1

EXAMPLE X-1

Procedure for the Preparation of 4(5)-(4-Methyl-cyclohex-3-enylmethyl) -1H-imidazole, but-2-enedioic acid salt:

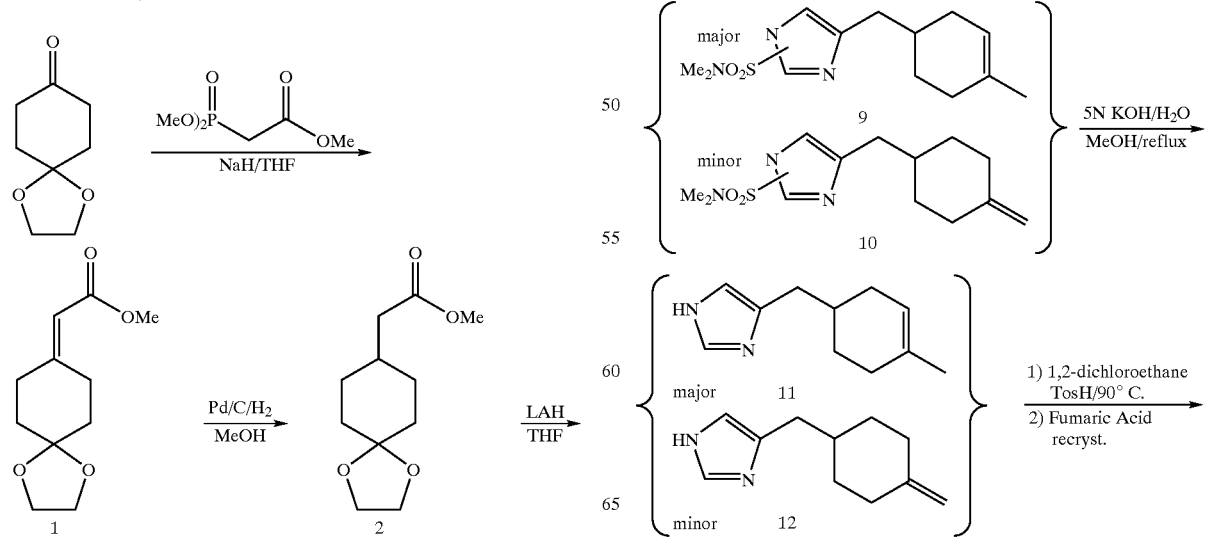

-continued

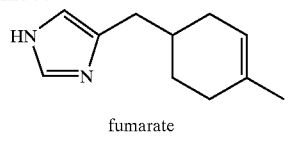

fumarate

13

Procedure-

To a slurry of NaH (60% in oil) (6.92 g, 288.28 mmol) in anhydrous THF (1500 ml) at 0° C. under argon with vigorous mechanical stirring added the trimethyl phosphonoacetate (52.50 g, 288.28 mmol) dropwise. Stirred this mixture an additional 30 minutes before adding the 1,4-cyclohexanedione mono-ethylene ketal (40.93 g, 262.07 mmol) in THF (170 ml) dropwise. The mixture was stirred an additional 18 h at 20° C. and then concentrated under reduced pressure. This residue was taken up in diethyl ether (1000 ml) and washed consecutively with $H_2O$ and brine, dried ($MgSO_4$), filtered and concentrated to give 60.08 g (98%) of the unsaturated ester 1 which was carried on without further purification. To a solution of unsaturated ester 1 in EtOAc (500 ml) added the palladium (10 wt. % on activated carbon) (2.13 g). This slurry was saturated with $H_2$ by repeated evacuations and $H_2$ backfills and then stirred for 16 h under one atmosphere pressure of $H_2$. Celite (5 g) was added to the reaction, the palladium was filtered off and the filtrate was concentrated under reduced pressure to give 59.45 g (98%) of the saturated ester 2 which was carried on without further purification. To a solution of $LiAlH_4$ (200.00 ml, 1 M in diethyl ether) at −78° C. under argon was added the unsaturated ester 2 in anhydrous THF (400 ml) in a slow stream with vigorous mechanical stirring. Upon warming to 20° C. additional THF (600 ml) was added and the reaction was stirred 1 h. The mixture was cooled to 0° C. and quenched by the careful, consecutive addition of $H_2O$ (7.60 ml), NaOH (7.60 ml of a 15% aqueous solution), and an additional portion of $H_2O$ (22.80 ml). The solids were filtered off and the filtrate was concentrated under reduced pressure. Subsequent purification by chromatography on $SiO_2$ with 20–50% EtOAc:hexanes gave 50.93 g (98%) of the alcohol 3 as a pale oil. To a solution of oxalyl chloride (20.65 ml, 41.29 mmol) in anhydrous $CH_2Cl_2$ (100 ml) at −78° C. under argon was added dropwise a solution of DMSO (6.72 g, 86.02 mmol) in $CH_2Cl_2$ (25 ml). After mechanical stirring for 15 minutes a solution of the alcohol 3 (6.40 g, 34.41 mmol) in $CH_2Cl_2$ (80 ml) was added dropwise and the mixture was stirred an additional 15 min at −78° C. before adding triethylamine (27.85 g, 275.30 mmol). The reaction was stirred 2 h at 20° C. and then quenched with saturated aqueous $NaHCO_3$. This mixture was extracted $CH_2Cl_2$ and the combined organic fractions were washed consecutively with $H_2O$ and brine, dried ($MgSO_4$) and concentrated under reduced pressure. The resulting solids were purified by chromatography on $SiO_2$ with 20–30% EtOAc:hexanes to give 5.08 g, (79%) of the aldehyde 4 as a white solid. A solution of aldehyde 4 (5.08 g, 27.59 mmol) in EtOH (40 ml) was treated with tosylmethyl isocyanide (TosMIC) (5.15 g, 26.27 mmol) and NaCN (0.13 g, 2.68 mmol) at 20° C. for 3 h and then refrigerated. After 2 h refrigeration the solids were filtered off, dissolved in anhydrous MeOH saturated with $NH_3$ (30 ml) and heated in a sealed tube at 100° C. for 3.5 h. The reaction was then concentrated under reduced pressure and the residues were taken up in $CHCl_3$, washed consecutively with saturated aqueous $NaHCO_3$ and brine, dried ($MgSO_4$) and concentrated to a red oil. This residue was further purified by chromatography on $SiO_2$ with 5–10% MeOH (saturated with $NH_3$): $CH_2Cl_2$ to give 1.87 g (31%) of the imidazole 5 as a pink oil. A solution of 5 (0.55 g, 2.48 mmol) in acetone (20 ml) containing HCl (5 N, 0.5 ml) was stirred for 5 h. The reaction was concentrated under reduced pressure, the residues were taken up in $H_2O$, neutralized to pH 7 with saturated aqueous $NaHCO_3$ and extracted exhaustively with $CHCl_3$/isopropyl alcohol (3:1). The combined organic portions were washed consecutively with $H_2O$ and brine, dried ($MgSO_4$) and concentrated. Chromatography on $SiO_2$ with 5–10% MeOH (saturated with $NH_3$): $CH_2Cl_2$ gave 0.43 g (97%) of the desired ketone 6. A solution of 6 (0.20 g, 1.11 mmol) in anhydrous DMF (4 ml) under argon was treated with triethylamine (0.14 g, 1.33 mmol) and dimethylsulfamoyl chloride (0.19 g, 1.33 mmol) under argon and stirred 16 h. The solids were filtered off and the filtrate was concentrated at via kugelrohr at 100° C. and 0.5 torr. The residues were taken up in $CHCl_3$ and washed consecutively with $H_2O$ and brine, dried ($MgSO_4$) and concentrated. Chromatography on $SiO_2$ with 1–5% $MeOH:CH_2Cl_2$ gave 0.22 g (69%) of the desired protected imidazole 7 as a mixture of regioisomers which were carried on without separation. A solution of 7 (0.18 g, 0.62 mmol) in anhydrous THF (10 ml) under argon was treated with methylmagnesium chloride (0.32 ml, 3.0 M in THF) and the resulting mixture was stirred 16 h. The reaction was quenched with a small amount of MeOH, concentrated under reduced pressure and the residues were taken up in $H_2O$. The mixture was acidified by the dropwise addition of 1 N HCl until the solution was homogenious and then the pH was adjusted to 7 with saturated aqueous $NaHCO_3$. The organic materials were extracted into $CHCl_3$ and the combined organic portions were washed consecutively with $H_2O$ and brine, dried ($MgSO_4$) and concentrated. Chromatography on $SiO_2$ with 5% $MeOH:CH_2Cl_2$ gave 0.18 g (95%) of the alcohol 8 as a mixture of regioisomers which were carried on without separation. A solution of 8 (0.14 g, 0.46 mmol) in anhydrous benzene (3 ml) at 0° C. under argon was treated with (methoxycarbonylsulfamoyl) triethylammonium hydroxide, inner salt (Burgess reagent) (0.12 g, 0.51 mmol) and stirred 1 h at 20° C. The reaction was concentrated under reduced pressure and subsequent purification by chromatography on $SiO_2$ with 5% $MeOH:CH_2Cl_2$ gave 0.12 g (92%) of the alkenes 9 and 10 as a mixture of isomers which were carried on without separation. The mixture of isomers 9 and 10 (0.12 g, 0.42 mmol) were refluxed in a solution composed of MeOH (2 ml) and KOH (2 ml of a 5 N solution) for 30 h. The reaction was concentrated under reduced pressure and the residues were taken up in $H_2O$ and extracted exhaustively with $CHCl_3$. The combined organic portions were washed consecutively with $H_2O$ and brine, dried ($MgSO_4$) and concentrated. Chromatography on $SiO_2$ with 5–10% MeOH (saturated with $NH_3$):$CH_2Cl_2$ gave 0.05 g (67%) of alkenes 11 and 12 as a mixture of isomers which were carried on without separation.

The mixture of alkenes 11 and 12 (0.045 g, 0.26 mmol) and p-toluenesulfonic acid hydrate (0.063 g, 0.32 mmol) were heated at reflux in 1,2-dichloroethane (2 ml) under argon for 20 h. The reaction was concentrated under reduced pressure and the residues were purified by chromatography on $SiO_2$ with 10% MeOH (saturated with $NH_3$):$CH_2Cl_2$ to give the free base of imidazole 13 (X-1) as one isomer. The imidazole was recrystallized by stirring in MeOH or THF with an equimolar amount of fumaric acid until all solids had disappeared followed by the addition of a small amount of diethyl ether and cold storage. The title compound 13 (X-1) 0.040 g (54%) was recovered as white crystals.

$^1$H NMR (300 MHz, DMSO w/TMS): δ 7.65 (s, 1 H), 6.78 (s, 1 H), 6.60 (s, 2 H), 5.31 (s, 1 H), 2.44 (d, J=6.7 Hz, 2 H), 2.02–1.82 (m, 3 H), 1.82–1.60 (m, 3 H), 1.59 (s, 3 H), 1.26–1.11 (m, 1 H) $^{13}$C NMR (75MHz, DMSO-d$_6$ w/TMS): δ 175.0, 165.2, 134.3, 134.1, 133.2, 120.3, 118.3, 33.2, 32.4, 31.2, 29.3, 28.3, 23.4.

EXAMPLE X-2

4(5)-(4-Ethyl-cyclohex-3-enylmethyl)-1H-imidazole, but-2-enedioic acid salt is prepared by substituting ethyl magnesium chloride in the method of X-1

EXAMPLE X-3

4(5)-(4-Pentyl-cyclohex-3-enylmethyl)-1H-imidazole, but-2-enedioic acid salt is prepared by substituting pentyl magnesium chloride in the method of X-1

Of course, in light of the detailed synthetic schemes disclosed within the present specification methods of making other compounds falling within the claims of the present specification will be clear to the skilled chemist.

EXAMPLE Y

A method for measuring α-agonist selectivity comprises the RSAT (Receptor Selection and Amplification Technology) assay as reported in Messier et al. (1995) "High throughput assays of cloned adrenergic, muscarinic, neurokinin and neurotrophin receptors in living mammalian cells", *Pharmacol. Toxicol.* 76:308–11 and adapted for use with alpha$_2$ receptors. The assay measures a receptor-mediated loss of contact inhibition that results in selective proliferation of receptor-containing cells in a mixed population of confluent cells. The increase in cell number is assessed with an appropriate transfected marker gene such as b-galactosidase, the activity of which can be easily measured in a 96-well format. Receptors that activate the G protein, G$_q$, elicit this response. Alpha$_2$ receptors, which normally couple to G$_i$, activate the RSAT response when coexpressed with a hybrid G$_q$ protein that has a G$_i$ receptor recognition domain, called G$_{q/i5}{}^2$. See Conklin et al. (1993) "Substitution of three amino acids switches receptor specificity of G$_q$a to that of G$_{ia}$," *Nature* 363:274–6.

NIH-3T3 cells are plated at a density of 2×10$^6$ cells in 15 cm dishes and maintained in Dulbecco's modified Eagle's medium supplemented with 10% calf serum. One day later, cells are cotransfected by calcium phosphate precipitation with mammalian expression plasmids encoding p-SV-b-galactosidase (5–10 mg), receptor (1–2 mg) and G protein (1–2 mg). 40 mg salmon sperm DNA may also be included in the transfection mixture. Fresh media is added on the following day and 1–2 days later, cells are harvested and frozen in 50 assay aliquots. Cells are thawed and 100 ml added to 100 ml aliquots of various concentrations of drugs in triplicate in 96-well dishes. Incubations continue 72–96 hr at 37°. After washing with phosphate-buffered saline, b-galactosidase enzyme activity is determined by adding 200 ml of the chromogenic substrate (consisting of 3.5 mM o-nitrophenyl-b-D-galactopyranoside and 0.5% nonidet P-40 in phosphate buffered saline), incubating overnight at 30° and measuring optical density at 420 nm. The absorbence is a measure of enzyme activity, which depends on cell number and reflects a receptor-mediated cell proliferation. The EC$_{50}$ and maximal effect of each drug at each alpha$_2$ receptor is determined. The efficacy or intrinsic activity is calculated as a ratio of the maximal effect of the drug to the maximal effect of a standard full agonist for each receptor subtype. Brimonidine, also called UK14,304-18, is used as the standard agonist for the alpha$_{2A}$ and alpha$_{2C}$ receptors. Oxymetazoline is the standard agonist used for the alpha$_{2B}$ receptor.

Table 1, below, provides the intrinsic activity values at subtypes of the α2-adrenoreceptor as determined in the RSAT assay for the compounds of above Examples B through X and certain adrenergic compounds not having selective agonist activity at the α2B or α2B /α2C subtype(s). At the α2A subtype, the compounds of the Examples are inactive or exhibit low efficacy (≦0.4). They have greater efficacy at the α2B and the α2C-subtypes than the α2A-subtype. Therefore, unlike ophthalmic α2-adrenoreceptor compounds such as clonidine and brimonidine, the compounds of Examples B through X can selectively activate α2-adrenoreceptor subtypes other than the α2A-subtype.

TABLE 1

Intrinsic Activity Relative to Brimonidine/Oxymetazoline

| Example | Structure/Compound | Brimonidine Alpha 2A | Oxymetazoline Alpha 2B | Brimonidine Alpha 2C |
|---|---|---|---|---|
| | oxymetazoline | 0.63 | 1.0 | 0.58 |
| | clonidine | 0.78 | 0.75 | 0.55 |
| | brimonidine | 1.0 | 0.93 | 1.0 |
| | 4(5)-(3-methyl-thiophen-2-ylmethyl)-1H-imidazole | 0.43 | 1.4 | 0.5 |
| D-3 | 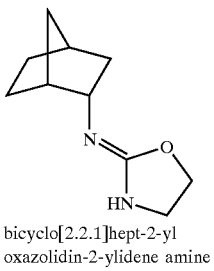 bicyclo[2.2.1]hept-2-yl oxazolidin-2-ylidene amine | 0 | 0.4 | 0 |

TABLE 1-continued

Intrinsic Activity Relative to Brimonidine/Oxymetazoline

| Example | Structure/Compound | Brimonidine Alpha 2A | Oxymetazoline Alpha 2B | Brimonidine Alpha 2C |
|---|---|---|---|---|
| D-1 | 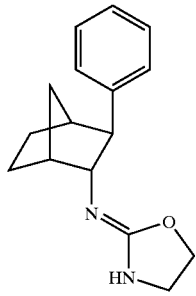 oxazolidin-2-ylidene-(3-phenyl bicyclo[2.2.1]hept-2-yl) amine | 0 | 0.47 | 0 |
| F | 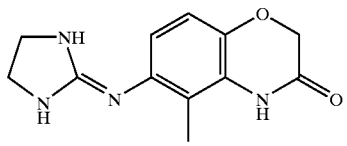 6-(imidazolidin-2-ylidene amino)-5-methyl-4H-benzo[1,4]oxazin-3-one | 0.3 | 0.9 | 0.2 |
| G | 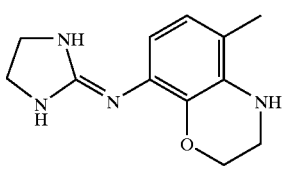 imidazolin-2-ylidene-(5-methyl-3,4-dihydro-2H-benzo[1,4]oxazin-8-yl) amine, hydrogen chloride salt | 0.1 | 0.87 | 0.33 |
| J-1 | 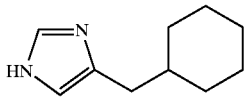 4(5)-cyclohexylmethyl-1H-imidazole | 0.1 | 0.83 | 0 |
| E-1 | 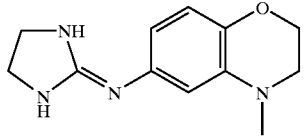 imidazolidin-2-ylidene-(4-methyl-3,4-dihydro-2H-benzo[1,4]oxazin-6-yl) amine | 0.33 | 0.83 | 0.35 |
| M | 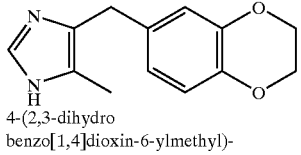 4-(2,3-dihydro benzo[1,4]dioxin-6-ylmethyl)-5-methyl-1H-imidazole | 0.2 | 0.97 | 0.27 |
| C-2 | 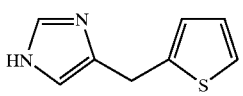 | 0.23 | 1.3 | 0.5 |

TABLE 1-continued

Intrinsic Activity Relative to Brimonidine/Oxymetazoline

| Example | Structure/Compound | Brimonidine Alpha 2A | Oxymetazoline Alpha 2B | Brimonidine Alpha 2C |
|---|---|---|---|---|
| | 4(5)-thiophen-2-ylmethyl-1H-imidazole | | | |
| C-1 | 4(5)-thiophen-3-ylmethyl-1H-imidazole | 0 | 0.83 | 0 |
| C-9 | 4(5)-benzo[b]thiophen-2-ylmethyl-1H-imidazole | 0.06 | 0.88 | 0.43 |
| C-3 | 4(5)-(5-methylthiophen-2-ylmethyl)-1H-imidazole | 0.1 | 0.88 | 0.43 |
| C-8 | 4(5)-benzyl-1H-imidazole | 0.3 | 0.9 | 0.4 |
| H | 4(5)-phenylsulfanyl-1H-imidazole | 0.2 | 0.93 | 0.15 |
| C-5 | 4(5)-furan-2-ylmethyl-1H-imidazole | 0 | 1.1 | 0.4 |
| B-3b | 4(5)-(1,2,3,4-tetrahydronaphthalen-2-ylmethyl)-1H-imidazole | 0 | 0.7 | 0 |
| J-2 | (S)-4(5)-(1,2,3,4-tetrahydronaphthalen-2-ylmethyl)-1H-imidazole | 0 | 0.8 | 0 |
| J-3 | (R)-4(5)-(1,2,3,4-tetrahydronaphthalen-2-ylmethyl)-1H-imidazole | 0.1 | 1 | 0.15 |

TABLE 1-continued

Intrinsic Activity Relative to Brimonidine/Oxymetazoline

| Example | Structure/Compound | Brimonidine Alpha 2A | Oxymetazoline Alpha 2B | Brimonidine Alpha 2C |
|---|---|---|---|---|
| L | 4(5)-(1-furan-2-ylethyl)-1H-imidazole | 0.23 | 0.9 | 0.57 |
| C-6 | 4(5)-furan-3-ylmethyl-1H-imidazole | 0.2 | 0.67 | 0.1 |
| C-4 | 4(5)-(5-chlorothiophen-2-ylmethyl)-1H-imidazole | 0.05 | 0.82 | 0.5 |
| D-2 | oxazolidin-2-ylidene-(3-o-tolyl bicyclo[2.2.1]hept-2-yl) amine | 0.25 | 0.75 | 0 |
| C-10 | 4(5)-benzofuran-2-ylmethyl-1H-imidazole | 0.05 | 0.48 | 0.1 |
| C-7 | 4(5)-(5-methylfuran-2-ylmethyl)-1H-imidazole | 0.08 | 0.73 | 0.2 |
| B-3a | 2-(1H-imidazol-4(5)-ylmethyl)-3,4-dihydro-2H-naphthalen-1-one) | 0.1 | 0.8 | 0.07 |
| I | CH$_3$SO$_3$H<br>4(5)-(1,2,3,4- | 0 | 0.5 | 0.2 |

TABLE 1-continued

Intrinsic Activity Relative to Brimonidine/Oxymetazoline

| Example | Structure/Compound | Brimonidine Alpha 2A | Oxymetazoline Alpha 2B | Brimonidine Alpha 2C |
|---|---|---|---|---|
| | tetrahydronaphthalen-2-ylmethyl)-4,5-dihydro-1H-imidazole, methane sulfonic acid salt | | | |
| B-2a | 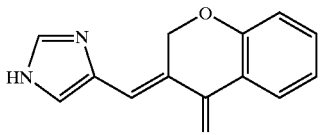<br>3-(1H-imidazol-4(5)-ylmethylene)chroman-4-one | 0 | 0.63 | 0.15 |
| B-2b | 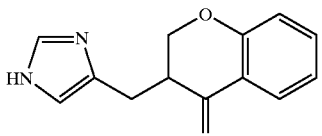<br>3-(1H-imidazol-4(5)-ylmethyl)chroman-4-one | 0 | 0.77 | 0 |
| B-2d | 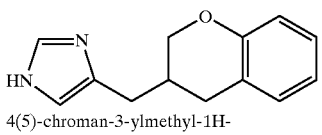<br>4(5)-chroman-3-ylmethyl-1H-imidazole | 0 | 0.6 | 0 |
| B-2c | 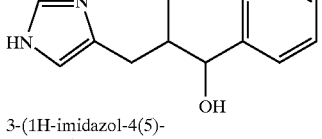<br>3-(1H-imidazol-4(5)-ylmethyl)chroman-4-ol | 0 | 0.65 | 0 |
| B-9a | 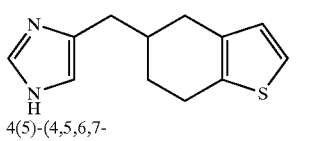<br>4(5)-(4,5,6,7-tetrahydrobenzo[b]thiophen-5-ylmethyl)-1H-imidazole | 0.08 | 0.46 | 0 |
| B-4a | 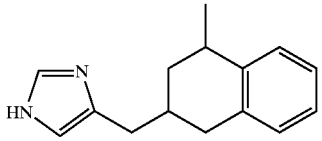<br>4(5)-(4-methyl-1,2,3,4-tetrahydronaphthalen-2-ylmethyl)-1H-imidazole | 0 | 0.75 | 0.1 |
| B-4b | 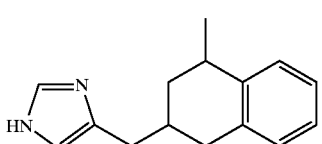<br>2-(1H-imidazol-4(5)-ylmethyl)-4-methyl-3,4- | 0.3 | 0.7 | 0.6 |

TABLE 1-continued

Intrinsic Activity Relative to Brimonidine/Oxymetazoline

| Example | Structure/Compound | Brimonidine Alpha 2A | Oxymetazoline Alpha 2B | Brimonidine Alpha 2C |
|---|---|---|---|---|
| | dihydro-2H-naphthalen-1-one | | | |
| B-11b | 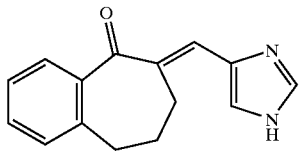<br>6-(1H-imidazol-4(5)-ylmethylene)-6,7,8,9-tetrahydrobenzocyclohepten-5-one | 0 | 0.3 | 0 |
| B-6 | 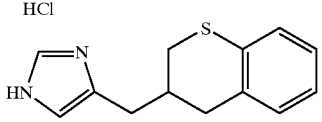<br>4(5)-thiochrom-3-ylmethyl-1H-imidazole, hydrogen chloride salt | 0 | 0.35 | 0 |
| B-5b | 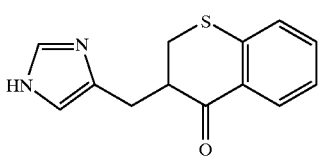<br>3-(1H-imidazol-4(5)-ylmethyl)thiochroman-4-one | 0 | 0.5 | 0.2 |
| B-5a | 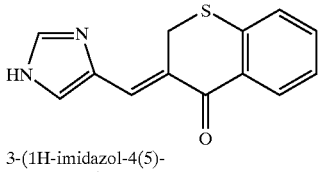<br>3-(1H-imidazol-4(5)-ylmethylene)thiochroman-4-one | 0 | 0.5 | 0.37 |
| B-7a | 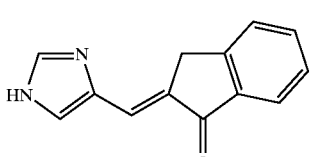<br>2-(1-H-imidazol-4(5)-ylmethylene)indan-1-one | 0 | 0.3 | 0 |
| B-11a | 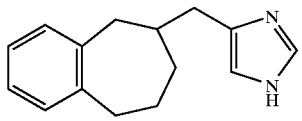<br>4(5)-(6,7,8,9-tetrahydro-5H-benzocyclohepten-6-ylmethyl)-1H-imidazole | 0.4 | 0.9 | 0 |
| B-7b | 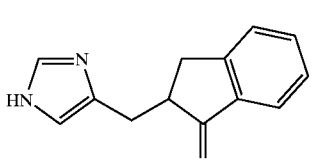<br>2-(1H-imidazol-4(5)- | 0 | 0.3 | 0 |

TABLE 1-continued

Intrinsic Activity Relative to Brimonidine/Oxymetazoline

| Example | Structure/Compound | Brimonidine Alpha 2A | Oxymetazoline Alpha 2B | Brimonidine Alpha 2C |
|---------|-------------------|----------------------|-----------------------|----------------------|
| | ylmethyl)indan-1-one | | | |
| B-1 | 4(5)-(7-methoxy-1,2,3,4-tetrahydronaphthalen-2-ylmethyl)-1H-imidazole, hydrogen chloride salt | 0.15 | 0.45 | 0.3 |
| B-1a | 2-(1H-imidazol-4(5)-ylmethyl)-7-methoxy-3,4-dihydro-2H-naphthalen-1-one | 0.15 | 0.6 | 0 |
| B-9b | 5-(1H-imidazol-4(5)-ylmethyl)-6,7-dihydro-5H-benzo[b]thiophen-4-one, hydrogen chloride salt | 0 | 0.68 | 0.15 |
| B-7c | 4(5)-indan-2-ylmethyl-1H-imidazole | 0 | 0.9 | 0 |
| B-10 | 4(5)-(4,4-dimethyl-1,2,3,4-tetrahydronaphthalen-2-ylmethyl)-1H-imidazole | 0 | 0.3 | 0 |
| B-8b | 4(5)-(7-methyl-1,2,3,4-tetrahydronaphthalen-2-ylmethyl)-1H-imidazole, hydrogen chloride salt | 0 | 0.6 | 0.2 |
| B-8a | 2-(1-H-imidazol-4(5)- | 0 | 0.4 | 0 |

TABLE 1-continued

Intrinsic Activity Relative to Brimonidine/Oxymetazoline

| Example | Structure/Compound | Brimonidine Alpha 2A | Oxymetazoline Alpha 2B | Brimonidine Alpha 2C |
|---|---|---|---|---|
| | ylmethyl)-7-methyl-3,4-dihydro-2H-naphthalen-1-one | | | |
| K-1 | 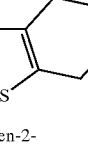 4(5)-(4,5,6,7-tetrahydrobenzo[b]thiophen-2-ylmethyl)-1H-imidazole | 0 | 0.53 | 0 |
| C-12 | 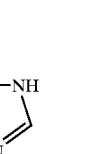 4(5)-(4-bromothiophen-2-ylmethyl)-1H-imidazole | 0.2 | 1.3 | 0.3 |
| C-13 | 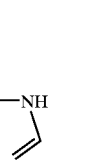 4(5)-(4-phenylthiophen-2-ylmethyl)-1H-imidazole | 0 | 0.5 | 0 |
| K-3 | 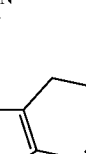 4(5)-(5,6-dihydro-4H-thieno[2,3-b]thiopyran-2-ylmethyl)-1H-imidazole | 0 | 0.37 | 0 |
| K-2 | 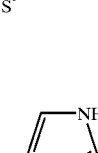 4(5)-(5-tert-butylfuran-2-ylmethyl)-1H-imidazole | 0 | 0.7 | 0 |
| C-11 |  4(5)-(5-ethylfuran-2-ylmethyl)-1H-imidazole | 0.2 | 0.5 | 0 |
| C-14 | 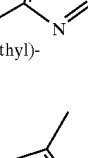 4(5)-(4-methylthiophen-2-ylmethyl)-1H-imidazole, hydrochloride salt | 0.27 | 0.7 | 0.3 |
| N-1 | 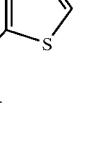 | 0.24 | 0.75 | 0.26 |

TABLE 1-continued

Intrinsic Activity Relative to Brimonidine/Oxymetazoline

| Example | Structure/Compound | Brimonidine Alpha 2A | Oxymetazoline Alpha 2B | Brimonidine Alpha 2C |
|---------|---|---|---|---|
|  | 2-(1H-imidazol-4(5)-ylmethyl)-3,4,5,6,7,8-hexahydro-2H-naphthalen-1-one, hydrochloride salt |  |  |  |
| Q-3 | 6-(1H-imidazol-4(5)-ylmethyl)-7,8-dihydro-6H-quinolin-5-one | 0.1 | 0.9 | 0.23 |
| Q-2 | (E)-6-(1H-imidazol-4(5)-ylmethylene)-7,8-dihydro-6H-quinolin-5-one | 0.1 | 0.87 | 0.13 |
| Q-1 | (Z)-6-(1H-imidazol-4(5)-ylmethylene)-7,8-dihydro-6H-quinolin-5-one | 0 | 0.75 | 0.2 |
| N-2 | 4(5)-(2,3,4,4a,5,6,7,8-octahydronaphthalen-2-ylmethyl)-1H-imidazole | 0 | 0.5 | 0.05 |
| Q-4 | 6-(1H-imidazol-4(5)-ylmethyl)-5,6,7,8-tetrahydro-quinoline, dihydrochloride | 0.1 | 0.8 | 0.1 |
| O | 4(5)-octahydro pentalen-2-ylmethyl-1H-imidazole, hydrochloride | 0 | 0.67 | 0.1 |

TABLE 1-continued

Intrinsic Activity Relative to Brimonidine/Oxymetazoline

| Example | Structure/Compound | Brimonidine Alpha 2A | Oxymetazoline Alpha 2B | Brimonidine Alpha 2C |
|---------|--------------------|----------------------|------------------------|----------------------|
| B-9c | 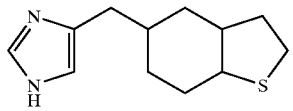<br>HCl<br>5-(octahydro benzo[b]thiophen-5-ylmethyl)-1H-imidazole, hydrochloride | 0 | 0.3 | 0 |
| R-3 | 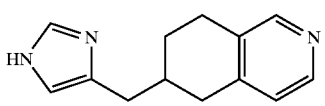<br>(C₄H₄O₄)₁.₅<br>6-(1H-imidazol-4(5)-ylmethyl)-5,6,7,8-tetrahydro-isoquinoline, fumarate | 0 | 0.6 | 0.4 |
| R-2 | 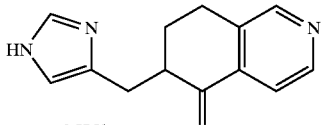<br>2 HCl<br>6-(1H-imidazol-4(5)-ylmethyl)-7,8-dihydro-6H-isoquinolin-5-one, dihydrochloride | 0 | 0.6 | 0.4 |
| R-1 | 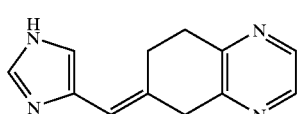<br>(E)-6-(1H-imidazol-4(5)-ylmethylene)-7,8-dihydro-6H-quinoxalin-5-one | 0.3 | 0.8 | 0.4 |
| P-1 | 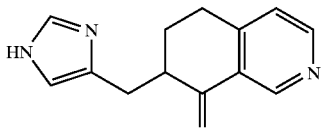<br>(C₄H₄O₄)₁.₅<br>7-(1H-imidazol-4(5)-ylmethyl)-6,7-dihydro-5H-isoquinoline-8-one, fumarate | 0 | 0.4 | 0 |
| P-2 | 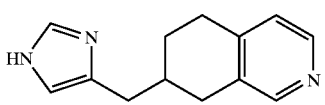<br>(C₄H₄O₄)₁.₅<br>7-(1H-imidazol-4(5)-ylmethyl)-5,6,7,8-tetrahydro-isoquinoline, fumarate | 0 | 0.4 | 0 |
| N-3 | 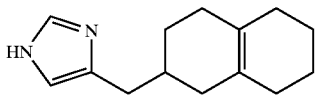<br>C₄H₄O₄<br>4(5)-(1,2,3,4,5,6,7,8- | 0 | 0.75 | 0 |

TABLE 1-continued

Intrinsic Activity Relative to Brimonidine/Oxymetazoline

| Example | Structure/Compound | Brimonidine Alpha 2A | Oxymetazoline Alpha 2B | Brimonidine Alpha 2C |
|---------|--------------------|----------------------|------------------------|----------------------|
| | octahydronaphthalen-2-ylmethyl)-1H-imidazole, fumarate | | | |
| Q-5 | 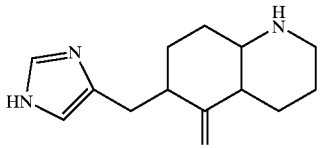<br>6-(1H-imidazol-4(5)-yl-methyl)-octahydroquinolin-5-one | 0 | 1.0 | 0 |
| S | $C_4H_4O_4$<br>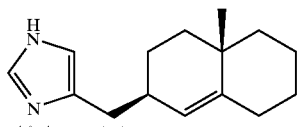<br>4(5)-(4a-methyl-2,3,4,4a,5,6,7,8-octahydro-naphthalen-2-ylmethyl)-1H-imidazole, but-2-enedioic acid salt | 0 | .6 | 0 |
| T-1 | $C_4H_4O_4$<br>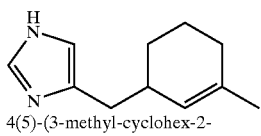<br>4(5)-(3-methyl-cyclohex-2-enylmethyl)-1H-imidazole, but-2-enedioic acid salt | 0.25 | 0.8 | 0.35 |
| T-2 | 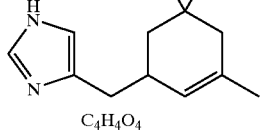<br>$C_4H_4O_4$<br>4(5)-(3,5,5-trimethyl-cyclohex-2-enylmethyl)-1H-imidazole, but-2-endioic acid salt | 0 | 0.7 | 0 |
| T-3 | 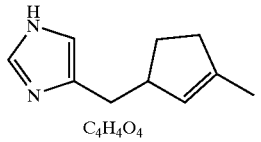<br>$C_4H_4O_4$<br>4(5)-(3-methyl cyclopent-2-enylmethyl)-1H-imidazole, but-2-enedioic acid salt | 0 | 1.08 | 0.36 |
| U-1 | 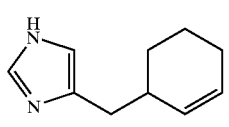<br>$C_4H_4O_4$<br>4(5)-cyclohex-2-enylmethyl-1H-imidazole, but-2-enedioic acid salt | 0.17 | 0.6 | 0.43 |

TABLE 1-continued

Intrinsic Activity Relative to Brimonidine/Oxymetazoline

| Example | Structure/Compound | Brimonidine Alpha 2A | Oxymetazoline Alpha 2B | Brimonidine Alpha 2C |
|---------|-------------------|---------------------|------------------------|----------------------|
| U-2 | 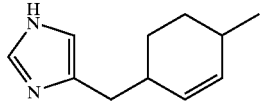<br>C₄H₄O₄<br>4(5)-(4-methyl-cyclohex-2-enylmethyl)-1H-imidazole, but-2-enedioic acid salt | 0.2 | 0.6 | 0.3 |
| V | 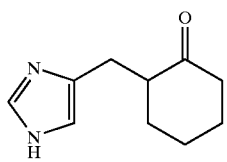<br>C₄H₄O₄<br>2-(1H-Imidazole-4(5)-ylmethyl)-cyclohexanone, but-2-enedioic acid salt | 0 | 0.4 | 0.5 |
| W-1 | 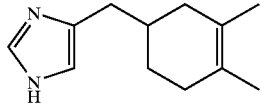<br>C₄H₄O₄<br>4(5)-(3,4-Dimethyl-cyclohex-3-enylmethyl)-1H-imidazole, but-2-enedioic acid salt | 0.07 | 0.55 | 0.07 |
| W-2 | 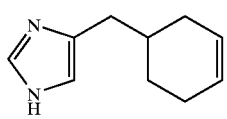<br>C₄H₄O₄<br>4(5)-Cyclohex-3-enylmethyl-1H-imidazole, but-2-enedioic acid salt | 0 | 0.6 | 0.7 |
| X-1 | 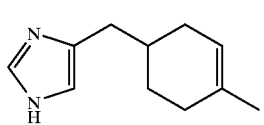<br>C₄H₄O₄<br>4(5)-(4-Methyl-cyclohex-3-enylmethyl)-1H-imidazole, but-2-enedioic acid salt | 0.15 | 0.8 | 0.11 |
| X-2 | 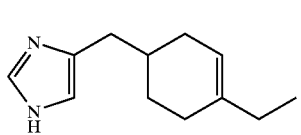<br>C₄H₄O₄<br>4(5)-(4-Ethyl-cyclohex-3-enylmethyl)-1H-imidazole, but-2-enedioic acid salt | 0 | 0.56 | 0 |

TABLE 1-continued

Intrinsic Activity Relative to Brimonidine/Oxymetazoline

| Example | Structure/Compound | Brimonidine Alpha 2A | Oxymetazoline Alpha 2B | Brimonidine Alpha 2C |
|---|---|---|---|---|
| X-3 | 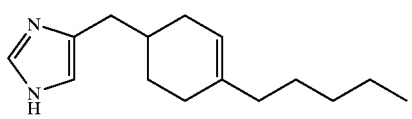<br>$C_4H_4O_4$<br>4(5)-(4-Pentyl-cyclohex-3-enylmethyl)-1H-imidazole, but-2-enedioic acid salt | 0.19 | 0.87 | 0 |
|  | oxymetazoline | 0.63 | 1.0 | 0.58 |
|  | clonidine | 0.78 | 0.75 | 0.55 |
|  | brimonidine | 1.0 | 0.93 | 1.0 |
|  | 4(5)-(3-methyl-thiophen-2-ylmethyl)-1H-imidazole | 0.43 | 1.4 | 0.5 |
| 1-A | 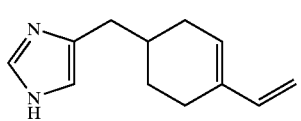<br>$C_4H_4O_4$ | 0 | 0.7 | 0 |
| 1-B | 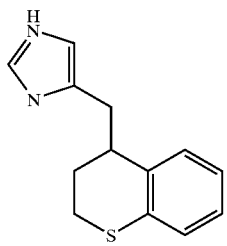<br>$C_4H_4O_4$ | 0 | 0.7 | 0 |
| 1C | 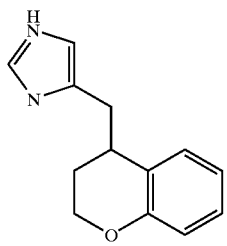<br>$C_4H_4O_4$ | 0 | 0.8 | 0 |
| 1D | 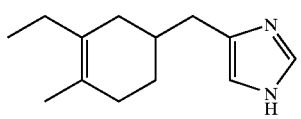 | 0 | 0.6 | 0 |
| 1E | 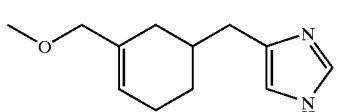 | 0 | 1 | 0 |
| 1F | 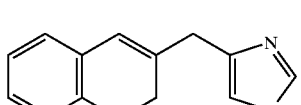 | 0 | 0.8 | 0 |

TABLE 1-continued

Intrinsic Activity Relative to Brimonidine/Oxymetazoline

| Example | Structure/Compound | Brimonidine Alpha 2A | Oxymetazoline Alpha 2B | Brimonidine Alpha 2C |
|---------|-------------------|----------------------|------------------------|----------------------|
| 1G | | 0 | 0.6 | 0 |
| 1H | | 0 | 0.6 | 0 |
| 1I | | 0 | 0.8 | 0.2 |
| 1J | | 0 | 0.5 | 0 |
| 1K | | 0 | 0.6 | 0 |
| 1L | | 0 | 0.7 | ND |
| 1M | | 0 | 0.6 | ND |
| 1N | | 0 | 0.7 | ND |
| 1O | | 0 | 0.8 | |

TABLE 1-continued

Intrinsic Activity Relative to Brimonidine/Oxymetazoline

| Example | Structure/Compound | Brimonidine Alpha 2A | Oxymetazoline Alpha 2B | Brimonidine Alpha 2C |
|---|---|---|---|---|
| 1P | (structure) | 0 | 0.7 | 0.3 |
| 1Q | (structure) | 0 | 0.75 | 0 |

EXAMPLE Z

IOP-Lowering and Sedative Side Effects

Measurements of IOP were made in fully conscious female cynomolgus monkeys weighing 3–4 kg with sustained elevated IOP that was produced in the right eye by argon laser photocoagulation of the trabecular meshwork. Animals were usable for experiments 2 months following surgery. During the experiments, monkeys sat in specially designed chairs (Primate Products, San Francisco), and were fed orange juice and fruit as needed. A 30R model Digilab pneumatonometer (Alcon, Tex.) was used to measure IOP.

Twenty five μl of an anesthetic (proparacaine) was topically applied to each monkey before IOP measurements to minimize ocular discomfort due to tonometry. Two baseline measurements were made prior to instillation of the drugs, followed by periodic measurements up to 6 hours post-instillation. The test compounds were administered unilaterally as a single 50 μl eye drop; the contralateral eyes received an equal volume of saline.

Many of the α2B or α2B/2C selective compounds of the examples were tested in the monkeys. Surprisingly, as Table 2 shows, these structurally diverse compounds all lowered IOP in the treated eye.

At the same time, sedation was measured and assessed according to the following score: 0=alert, typical vocalization, movement, etc.; 1=calm, less movement; 2=slightly sedated, some vocalization, responsive to stimulation; 3=sedated, no vocalization, some response to stimulation; 4=asleep.

The compounds of the present invention also did not cause sedation. This contrasts with the action of clonidine and brimonidine, which caused sedation.

TABLE 2

The effects of $\alpha_2$-adrenoceptor agonists on IOP and sedation in conscious cynomolgus monkeys following ocular administration in eyes made unilaterally hypertensive by argon laser photocoagulation. Measurements were made periodically up to 6 hours. Sedation was assessed subjectively during the IOP experiments using the following scoring: 0 = alert, typical vocalization, movement, etc.; 1 = calm, less movement; 2 = slightly sedated, some vocalization, responsive to stimulation; 3 = sedated, no vocalization, some response to stimulation; 4 = asleep. Number of animals per group = (6–9).

| Compounds | Dose (%) | Maximum % Decrease From Pretreatment Levels Hypertensive Eye | Sedation (0–4) |
|---|---|---|---|
| Saline | — | 7 ± 2 | 0–1 |
| Clonidine | 0.1 | 25 ± 4 | 1 |
|  | 0.3 | 41 ± 5 | 2 |
| Brimonidine | 0.1 | 25 ± 3 | 1 |
|  | 0.3 | 40 ± 4 | 2 |
| J-1 | 1 | 26 ± 5 | 0 |
|  | 3 | 33 ± 3 | 0 |
| E-1 | 0.3 | 25 ± 4 | 0 |
|  | 1 | 27 ± 3 | 0 |
| C-1 | 1 | 25 ± 4 | 0 |
|  | 3 | 29 ± 4 | 0 |
| D-1 | 1 | 25.6 ± 3.9 | 0 |
| M | 1 | 22.5 ± 5.4 | 0 |
| C-2 | 1 | 29.6 ± 5.5 | 0 |
| C-9 | 0.3 | 13.7 ± 4.5 | 0 |
|  | 1 | 25.1 ± 4.9 | 0 |
| C-3 | 0.3 | 20.6 ± 4.8 | 0 |
|  | 1 | 25.0 ± 6.4 | 0 |
| C-8 | 1 | 31.2 ± 3.3 | 0 |
| B-3b | 0.1 | 25.9 ± 3.5 | 0 |
|  | 0.3 | 31.2 ± 4.3 | 0 |
| C-4 | 0.3 | 17.7 ± 4.0 | 0 |
|  | 1 | 29.3 ± 4.9 | 0 |
| C-7 | 1 | 32.3 ± 5.7 | 0 |
| J-2 | 0.03 | 12.4 ± 3.7 | 0 |
|  | 0.3 | 27.3 ± 3.1 | 0 |
| J-3 | 0.03 | 16.4 ± 4.7 | 0 |
|  | 0.3 | 26.5 ± 3.8 | 0 |
| B-2d | 0.1 | 22.0 ± 4.6 | 0 |
|  | 0.3 | 17.0 ± 4.2 | 0 |
|  | 1 | 18.1 ± 5.2 | 0 |
| B-9a | 0.03 | 17.6 ± 1.7 | 0 |
|  | 0.1 | 26.7 ± 6.1 | 0 |
|  | 0.3 | 24.8 ± 3.3 | 0 |
|  | 1 | 26.8 ± 5.4 | 0 |

TABLE 2-continued

The effects of $\alpha_2$-adrenoceptor agonists on IOP and sedation in conscious cynomolgus monkeys following ocular administration in eyes made unilaterally hypertensive by argon laser photocoagulation. Measurements were made periodically up to 6 hours. Sedation was assessed subjectively during the IOP experiments using the following scoring: 0 = alert, typical vocalization, movement, etc.; 1 = calm, less movement; 2 = slightly sedated, some vocalization, responsive to stimulation; 3 = sedated, no vocalization, some response to stimulation; 4 = asleep. Number of animals per group = (6–9).

| Compounds | Dose (%) | Maximum % Decrease From Pretreatment Levels Hypertensive Eye | Sedation (0–4) |
|---|---|---|---|
| B-6 | 0.3 | 13.8 ± 2.4 | 0 |
|  | 1 | 22.1 ± 6.3 | 0 |
| B-9b | 0.1 | 18.7 ± 5.5 | 0 |
|  | 0.3 | 26.9 ± 6.1 | 0 |

EXAMPLE AA
Measurement of Cardiovascular Side Effects

Cardiovascular measurements were made in a different group of monkeys using a BP 100S automated sphygmomanometer (Nippon Colin,. Japan). Intravenous (IV) administration of certain of the compounds of the present invention at doses ten to thirty times higher than the doses for clonidine and brimonidine did not reduce heart rate or lower blood pressure. Interestingly, the compound 4(5)-3-methylthiophen-2-ylmethyl)-1H-imidazole, which has intrinsic activity of 0.43 at the α2A-subtype, exhibited a weak effect on heart rate. Clonidine and brimonidine had even greater effects on heart rate. See Table 3 below.

TABLE 3

The effects of $\alpha_2$-adrenoceptor agonists on cardiovascular variables in conscious cynomolgus monkeys following i.v. administration. Measurements were made periodically up to 6 hours. Number of animals per group = (6–10).

| Compounds | Dose (µg/kg) | Maximum % Decrease From Pretreatment Levels | |
|---|---|---|---|
| | | Mean Arterial Blood Pressure | Heart Rate |
| Saline | — | 7 ± 4 | 8 ± 3 |
| Clonidine | 17 | 29 ± 7 | 32 ± 4 |
|  | 50 | 35 ± 5 | 50 ± 5 |
| Brimonidine | 17 | 36 ± 3 | 52 ± 3 |
|  | 50 | 37 ± 5 | 54 ± 3 |
| J-1 | 17 | 7 ± 5.3 | 13 ± 4 |
|  | 50 | 4 ± 2 | 6 ± 2 |
|  | 167 | 7 ± 5 | 3 ± 3 |
|  | 500 | 13 ± 3 | 7 ± 4 |
| E-1 | 17 | 7 ± 4 | 11 ± 4 |
|  | 50 | 7 ± 2 | 14 ± 5 |
|  | 167 | 9 ± 4 | 11 ± 5 |
| C-1 | 50 | 12.8 ± 12 | 12 ± 4 |
|  | 500 | +5 ± 8* | +11 ± 9* |
| M | 500 | 0.8 ± 2.3 | 5.5 ± 1.9 |
| C-2 | 500 | 6.6 ± 1.7 | 6.5 ± 2.9 |
| C-9 | 3.0 | 5.0 ± 2.3 | 9.4 ± 3.0 |
|  | 17 | 1.0 ± 4.1 | +9.4 ± 1.8* |
|  | 50 | 0.1 ± 3.8 | 16 ± 3.2 |
|  | 500 | 6.0 ± 2.2 | 5.9 ± 3.3 |
| C-3 | 500 | 2.3 ± 2.7 | 10.6 ± 3.4 |
| C-8 | 500 | 5.5 ± 2.7 | 16.6 ± 1.9 |
| C-5 | 500 | 3.9 ± 2.8 | 7.1 ± 3.9 |
| B-3b | 50 | 2.4 ± 4.3 | 10.0 ± 2.8 |
| C-4 | 500 | 5.3 ± 2.9 | 10.9 ± 3.6 |
| C-7 | 500 | 3.0 ± 3.9 | 6.1 ± 3.7 |
| J-2 | 500 | +0.6 ± 3.1* | 6.4 ± 3.3 |

TABLE 3-continued

The effects of $\alpha_2$-adrenoceptor agonists on cardiovascular variables in conscious cynomolgus monkeys following i.v. administration. Measurements were made periodically up to 6 hours. Number of animals per group = (6–10).

| Compounds | Dose (µg/kg) | Maximum % Decrease From Pretreatment Levels | |
|---|---|---|---|
| | | Mean Arterial Blood Pressure | Heart Rate |
| J-3 | 500 | +1.0 ± 2.1* | +10.6 ± 6.0* |
| B-2b | 500 | 5.7 ± 1.4 | 6.4 ± 3.6 |
| B-2d | 500 | +8.9 ± 3.4* | +15.5 ± 3.4* |
| B-9a | 500 | +10.8 ± 3.2* | +23.8 ± 4.4* |
| B-9b | 500 | 2.8 ± 1.8 | +20.2 ± 3.4* |
| 4(5)-(3-methylthiophen-2-ylmethyl)-1H-imidazole | 50 | 9 ± 3 | 23 ± 4 |
|  | 167 | 8 ± 6 | 32 ± 8 |

*showed increase from base levels

EXAMPLE BB

The studies in the above Examples Z and AA demonstrate that a therapeutic effect of alpha2 agonists can be separated from sedative and cardiovascular side effects. This separation is accomplished with compounds that share the property of being preferentially active at the alpha2B and alpha2B/alpha2C subtypes relative to the alpha2A subtype.

The prior art alpha2 adrenergic agonists, which activate all three alpha2 receptors, cause sedation, hypotension and bradycardia, preventing or severely limiting their use for treating diseases and disorders that are known to be ameliorated by them. Such diseases and disorders include muscle spasticity including hyperactive micturition, diarrhea, diuresis, withdrawal syndromes, pain including neuropathic pain, neurodegenerative diseases including optic neuropathy, spinal ischemia and stroke, memory and cognition deficits, attention deficit disorder, psychoses including manic disorders, anxiety, depression, hypertension, congestive heart failure, cardiac ischemia and nasal congestion. See, for example, Hieble et al., "Therapeutic applications of agents interacting with alpha-adrenoceptors, in Alpha-adrenoceptors: molecular biology, biochemistry and pharmacology". *Prog. Basic Clin. Pharmacol.* (Basel, Karger) 8, pp. 180–220(1991). For example, clonidine has been shown to be clinically effective in providing pain relief for postoperative, cancer-associated and neurogenic pain. But, as stated in Maze and Tranquilli, Maze MB and Tranquilli, W. "Alpha-2 adrenoceptor agonists: defining the role in clinical anesthesia". *Anesthesiology* 74, 581–605 (1991), the "full clinical promiser" of this and other alpha2 agonists requires the development of compounds that do not cause sedation, hypotension and bradycardia.

The above-listed diseases and disorders are treatable by activation of α2B or α2B/2C receptor subtype(s). Therefore, the alpha2 compounds described above that have been shown above not to elicit sedation and cardiovascular effects, are useful and advantageous in the treatment of these conditions.

Amelioration of neuronal degeneration in glaucomatous neuropathy is another example of the novel utility of the compounds of the invention. Recent studies have demonstrated that clonidine and other alpha2 agonists are neuroprotective of retinal cells in several rat models of neuronal degeneration. These models include light-induced photoreceptor degeneration in albino rat, as described in Wen et al, "Alpha2-adrenergic agonists induce basic fibroblast growth factor expression in photoreceptors in vivo and ameliorate light damage." *J. Neurosci.* 16, 5986–5992 and calibrated rat optic nerve injury resulting in secondary loss of retinal ganglion cells, as described in Yoles et al, "Injury-induced secondary degeneration of rat optic nerve can be attenuated by alpha2-adrenoceptor agonists AGN 191103 and brimonidine". *Invest. Ophthalmol. Vis. Sci.* 37, 540,S114. However, unlike the compounds of the present invention, the doses used in these studies—0.1 to >1 mg/kg by intraperitoneal or intramuscular injection—also cause sedation and cardiovascular effects. Induction of the expression of basic fibroblast growth factor (bFGF) is considered a sensitive indicator of alpha2 receptor activation in the retina (Wen et al above) and measurement of bFGF induction following topical administration of alpha2 agonists to rat eyes indicates that approximately a 1% dose is necessary to induce a 2–3 fold increase in bFGF levels that correspond with alpha2 agonist mediated neuroprotection (See Wen et al, above, and Lai et al, "Neuroprotective effect of ocular hypotensive agent brimonidine", in *Proceedings of XIth Congress of the European Society of Ophthalmology* (Bologna, Monduzzi Editore), 439–444.) These topical doses of current alpha2 agonists such as clonidine are known to result in systemic side effects such as sedation and hypotension that would prevent their use as ocular neuroprotective agents. Additionally commonly assigned and co-pending application, 08/496,292 filed on 28 Jun. 1995, discloses and claims the use of certain non-selective α2-adrenergic agents in treating neural injury, the contents of which are hereby incorporated by reference in their entirety.

The compounds of the present invention do not cause sedation and cardiovascular effects following topical administration of doses of at least 3% in monkeys. Thus, neuroprotective concentrations of these compounds can be reached in humans without causing side effects. In fact, as reported below, the compound of Example B-9(b) has been shown to be neuroprotective in the calibrated rat optic nerve injury model of Yoles et al, above. See Table 4, below.

TABLE 4

Retinal Ganglion Cell Numbers at 2 Weeks Post-Injury (cells/microscopic field)

| Control (vehicle i.p.) | Example B-9(b) (0.5 mg/kg i.p.) |
|---|---|
| 33 ± 8 | 73 ± 12 |
| n = 8 | n = 5 |

This level of neuroprotection is comparable to the effect seen in previous studies with the standard alpha 2-adrenoceptor agonist, brimonidine, and the neuroprotective agent, MK801.

EXAMPLE CC

Alleviation of pain including neuropathic pain is another example of a disorder in which the compounds of the invention are useful and advantageous since pain is alleviated without undesirable side effects. Clonidine, an agonist that activates all three alpha2 receptors, has been used clinically for treating chronic pain, but its utility for this indication is limited because it causes sedation and cardiovascular side effects. Compounds of the present invention were compared to clonidine and brimonidine in a rodent model of neuropathic pain that is known to be predictive of clinical activity. (See, for example, Kim, S. and Chung, J. "An experimental model for peripheral neuropathy produced by segmental spinal nerve ligation in the rat." *Pain* 50 pp. 355–363 (1992).) Following ligation of two spinal nerves, the animals develop a sensitivity to normally non-painful stimuli such as touch. The ability of alpha2 compounds to reverse this sensitivity, called allodynia, was tested 30 minutes after dosing by either intrathecal or intraperitoneal administration. The sedative activity of each compound was also measured using an activity chamber.

The compounds of the invention, exemplified by N-1, are able to alleviate the allodynia without causing sedation, even at very high doses. This is in contrast to clonidine and brimonidine, which cause sedation at doses only slightly higher than their anti-allodynic doses. See tables 5 and 6, below.

TABLE 5

The anti-allodynic and sedative effects of alpha2-adrenoceptor agonists in rats 30 minutes following intrathecal administration (N = 6).

| Compound | Dose (µg) | Reversal of Tactile Allodynia (%) | Sedation (%) |
|---|---|---|---|
| Clonidine | 0.1 | 20* | ND |
| | 1 | 96* | 15 |
| | 10 | ND | 60* |
| N-1 | 3 | 13 | ND |
| | 30 | 64* | 0 |
| | 300 | ND | 0 |

*p < 0.05 compared to saline control
ND signifies no data

TABLE 6

The anti-allodynic and sedative effects of alpha2-adrenoceptor agonists in rats 30 minutes following intraperitoneal administration (N = 6).

| Compound | Dose (mg/kg) | Reversal of Tactile Allodynia (%) | Sedation (%) |
|---|---|---|---|
| Brimondine | 3 | 0 | ND |
| | 30 | 37* | 24 |
| | 300 | ND | 67* |
| N-1 | 3 | 3 | ND |
| | 30 | 41* | ND |
| | 10,000 | ND | 0 |

*p < 0.05 compared to saline control
ND signifies no data

The results of these Examples demonstrate that the common side effects of α2-adrenoceptor drugs are mediated by the α2A-subtype and that their ocular antihypertensive and other therapeutic actions can be mediated by a subtype other than the α2A-subtype. Thus, α2-adrenoceptor compounds of unrelated structural classes, that have in common low functional activity at the α2A-subtype, lower IOP and elicit other therapeutic actions without dose-limiting side effects.

While particular embodiments of the invention have been described, it will be understood, of course, that the invention is not limited thereto since many obvious modifications can be made, and it is intended to include within this invention any such modification as will fall within the scope of the appended claims.

Having now described the invention.
We claim:
1. A compound selected from the group consisting of:

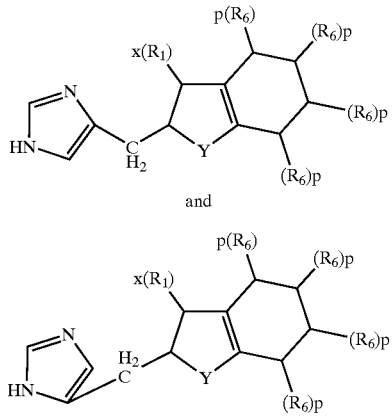

and wherein $R_1$ is independently selected from the group consisting of H; halogen; $C_{1-4}$ alkyl; $C_{1-4}$ alkenyl; $C_{1-4}$ alkynyl; —$COR_4$ where $R_4$ is H, $C_{1-4}$ alkyl or $C_{1-4}$ alkoxy; $C_{3-6}$ cycloalkyl; aryl; cyano; nitro; trihalomethyl; oxo; or —$(CH_2)_n$—X—$(CH_2)_m$—$(R_5)_o$— where X is O, S or N, n is 0–3, m is 0–3, o is 0–1, and $R_5$ is methyl or $H_{1-2}$, each $R_6$ is independent selected from the group consisting of H; halogen; $C_{1-4}$ alkyl; $C_{1-4}$ alkenyl; $C_{1-4}$ alkynyl; —$COR_4$ where $R_4$ is H, $C_{1-4}$ alkyl or $C_{1-4}$ alkoxy; $C_{3-6}$ cycloalkyl; aryl; cyano; nitro; trihalomethyl and oxo wherein each p is independently 1 or 2 and Y is —$(C(R_7)_z)_2$—, wherein $R_7$ is independently defined identically to $R_1$ and z is independently 1 or 2, said compound further having selective agonist activity at the α2B or α2B/α2C adrenergic receptor subtype(s) over the α2A adrenergic receptor subtype, and all pharmacologically acceptable salts, esters, stereoisomers and racemic mixtures thereof.

2. The compound of claim 1 wherein Y is $CH_2$—$CH_2$.
3. The compound of claim 1 wherein $R_1$, $R_6$ and $R_7$ are independently H; halogen; $C_{1-4}$ alkyl; $C_{1-4}$ alkenyl; or $C_{1-4}$ alkynyl.
4. The compound of claim 1 wherein Y is $CH_2$—$CH_2$ and $R_1$, $R_6$ and $R_7$ are independently H; halogen; $C_{1-4}$ alkyl; $C_{1-4}$ alkenyl; or $C_{1-4}$ alkynyl.
5. The compound of claim 4 wherein $R_1$ is H and x is 2.
6. The compound of claim 4 wherein at least one $R_6$ is H.
7. The compound of claim 6 wherein at least two $R_6$ are H.
8. The compound of claim 7 wherein at least three $R_6$ are H.
9. The compound of claim 8 wherein at least six $R_6$ are H.
10. The compound of claim 8 wherein eight $R_6$ are H.
11. The compound of claim 3 wherein $R_1$ is H and x is 2.
12. The compound of claim 11 wherein at least one $R_6$ is H.
13. The compound of claim 12 wherein at least two $R_6$ are H.
14. The compound of claim 13 wherein at least three $R_6$ are H.
15. The compound of claim 14 wherein at least six $R_6$ are H.
16. The compound of claim 15 wherein eight $R_6$ are H.
17. The compound of claim 16 in which $R_1$ is H and x is 2.
18. The compound of claim 17 in which Y is —$CH_2$—$CH_2$—.

* * * * *